(12) United States Patent
Fu et al.

(10) Patent No.: US 12,325,695 B2
(45) Date of Patent: Jun. 10, 2025

(54) 5-(4-PYRIDYLOXY)PYRAZOLE COMPOUNDS SERVING AS TGF-βR1 KINASE INHIBITOR

(71) Applicant: JIANGSU AOSAIKANG PHARMACEUTICAL CO., LTD., Jiangsu (CN)

(72) Inventors: Xiangyu Fu, Shanghai (CN); Charles Z. Ding, Shanghai (CN); Lihong Hu, Shanghai (CN); Shuhui Chen, Shanghai (CN)

(73) Assignee: JIANGSU AOSAIKANG PHARMACEUTICAL CO., LTD., Jiangsu (CN)

( * ) Notice: Subject to any disclaimer, the term of this patent is extended or adjusted under 35 U.S.C. 154(b) by 929 days.

(21) Appl. No.: 17/425,426

(22) PCT Filed: Jan. 22, 2020

(86) PCT No.: PCT/CN2020/073832
§ 371 (c)(1),
(2) Date: Jul. 23, 2021

(87) PCT Pub. No.: WO2020/151749
PCT Pub. Date: Jul. 30, 2020

(65) Prior Publication Data
US 2022/0098171 A1    Mar. 31, 2022

(30) Foreign Application Priority Data

Jan. 24, 2019 (CN) .......................... 201910069936.2

(51) Int. Cl.
| | | |
|---|---|---|
| *C07D 401/12* | (2006.01) | |
| *A61K 31/4439* | (2006.01) | |
| *A61K 31/444* | (2006.01) | |
| *A61K 31/497* | (2006.01) | |
| *A61P 35/00* | (2006.01) | |
| *C07D 401/14* | (2006.01) | |
| *C07D 405/14* | (2006.01) | |

(52) U.S. Cl.
CPC ............ *C07D 401/12* (2013.01); *A61P 35/00* (2018.01); *C07D 401/14* (2013.01); *C07D 405/14* (2013.01)

(58) Field of Classification Search
CPC .. C07D 401/12; C07D 401/14; C07D 405/14; A61P 35/00; A61K 31/4439; A61K 31/444; A61K 31/497
See application file for complete search history.

(56) References Cited

FOREIGN PATENT DOCUMENTS

| | | |
|---|---|---|
| CN | 1951939 A | 4/2007 |
| CN | 106795139 A | 5/2017 |
| CN | 201910069936.2 | 1/2019 |
| TW | 201329067 A | 7/2013 |
| WO | WO-02094833 A1 | 11/2002 |
| WO | WO-2013086397 A1 | 6/2013 |
| WO | WO-2016057278 A1 | 4/2016 |
| WO | WO-2020258006 A1 | 12/2020 |

OTHER PUBLICATIONS

Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*
Cecil Textbook of Medicine, 20th Ed, vol. 1, 1997 (Year: 1997).*
Apr. 22, 2020 International Search Report issued in International Patent Application No. PCT/CN2020/073832.
Jan. 22, 2020 Written Opinion of the International Searching Authority issued in Internatioanl Patent Application No. PCT/CN2020/073832.
Korean Office Action regarding Patent Application No. 1020217026698, dated Mar. 15, 2024.
Extended European Search Report regarding EP Application No. 20744402, mailing date: Sep. 27, 2022.
First Japanese Office Action regarding JP Application No. 2021543265, mailing date: Aug. 23, 2022.
Feb. 7, 2023 Second Office Action issued in Japanese Patent Application No. 2021543265.

* cited by examiner

*Primary Examiner* — Jeffrey H Murray
*Assistant Examiner* — Kevin S Martin
(74) *Attorney, Agent, or Firm* — Harness, Dickey & Pierce, P.L.C.

(57) ABSTRACT

Disclosed are a group of 5-(4-pyridyloxy)pyrazole compounds serving as a TGF-βR1 kinase inhibitor, and applications of same in preparing a TGF-βR1 kinase inhibitor medicament. Specifically disclosed are the compounds as represented by formula (I), a pharmaceutically acceptable salt or an isomer thereof.

19 Claims, No Drawings

5-(4-PYRIDYLOXY)PYRAZOLE COMPOUNDS SERVING AS TGF-βR1 KINASE INHIBITOR

CROSS-REFERENCE TO RELATED APPLICATIONS

This application is a U.S. National Phase Application under 35 U.S.C. 371 of International Application No. PCT/CN2020/073832, filed on Jan. 22, 2020, which claims the benefit of Chinese Patent Application No. 201910069936.2, filed on Jan. 24, 2019. The entire disclosures of the above applications are incorporated herein by reference.

TECHNICAL FIELD

The present disclosure relates to a class of 5-(4-pyridyloxy)pyrazole compounds as a TGF-βR1 inhibitor, and their applications in the preparation of TGF-βR1 inhibitor medicament. Specifically the present disclosure provides a compound represented by formula (I), a pharmaceutically acceptable salt thereof or an isomer thereof.

BACKGROUND

Transforming growth factor-β (TGF-β) is a superfamily of multifunctional growth factors with a wide range of biological activities, which participates in early embryonic development, formation of cartilage and bone, synthesis of outer matrix, inflammation, interstitial fibrosis, regulation of immune and endocrine functions, formation and development of tumors.

The TGF-β superfamily consists of a class of structurally and functionally related polypeptide growth factors, and TGF-β is one of the important members of this family. In mammals, TGF-β mainly exists in three forms, TGF-β1, TGF-β2 and TGF-β3, which are located on different chromosomes, wherein, TGF-β1 accounts for the highest proportion (>90%) in somatic cells, which has the strongest activity, the most functions, and the most extensive distribution.

TGF-β signal molecules conduct signal transduction through a transmembrane receptor complex. TGF-β receptors are transmembrane proteins that exist on the cell surface, and divided into Type I receptor (TGF-βR1), Type II receptor (TGF-βR2) and Type III receptor (TGF-βR3), wherein, TGF-βR1 is also called activin receptor-like kinase 5 (ALK5). TGF-βR3 lacks intrinsic activity, which is mainly related to the storage of TGF-β. TGF-βR1 and TGF-βR2 belong to the serine/threonine kinase family. Type II receptor can bind to TGF-β ligands with high affinity, form heterologous receptor complexes with Type I receptor and phosphorylate a region (GS domain), which is rich in glycine and serine residues near the membrane of Type I receptor to initiate a cascade reaction of intracellular signals.

Smads are important intracellular TGF-β signal transduction and regulatory molecules, which can directly transduce TGF-β signal from the cell membrane, such as, into the nucleus. The TGF-β/Smads signaling pathway plays an important role in the occurrence and development of tumors. In TGF-β/Smads signal transduction, activated TGF-β firstly binds to TGF-βR2 on the cell membrane surface to form a heterodimeric complex, and TGF-βR1 recognizes and binds to the heterodimeric complex.

TGF-βR2 phosphorylates the serine/threonine of the GS domain in the cytoplasmic region of TGF-βR1 to activate TGF-βR1. Activated TGF-βR1 further phosphorylates R-Smads (Smad2/Smad3) protein, which then binds to Co-Smad (Smad4) to form a heterotrimeric complex. This complex enters the nucleus and cooperates with other co-activator and co-inhibitor to regulate the transcription of target genes. Any changes in the TGF-β/Smads signaling pathway will cause abnormalities in the signal transduction pathway.

Current studies have shown that in tumor cells, TGF-β can directly affect tumor growth (non-intrinsic effect of TGF-β signaling), or indirectly affect tumor growth by inducing epithelial-mesenchymal transition, blocking anti-tumor immune responses, increasing tumor-related fibrosis and strengthening vascular regeneration (intrinsic effect of TGF-β). At the same time, TGF-β has a strong fibrosis-inducing effect, and it is an activator of fibroblasts associated with tumors. These fibroblasts are the main resources of collagen type I and other fibrotic factors. The induced products of fibroblasts and other fibrotic factors may continue to cultivate a microenvironment that reduces immune response, increases drug resistance, and strengthens tumor angiogenesis. In addition, TGF-β affects vascular regeneration during ontogeny and tumor growth. For example, mouse embryos deficient in TGF-β R1 shows severe vascular development defects, which proves that the TGF-β signaling pathway is a key regulator in the development of vascular endothelial and smooth muscle cells.

Recent researches also have pointed out that TGF-β is obviously related to immune escape and has a greater impact on the anti-tumor immune response mediated by CD8+ T cells. In clinical trials for metastatic urinary epithelial cancer, patients with high TGF-β gene expression respond to PD-L1 monoclonal antibody and have a low simulated survival rate. The basic research of TGF-β monoclonal antibody also proves that when it is used in conjunction with PD-L1 monoclonal antibody, more CD8+ T cells infiltrate and play a role, which reveals the blocking effect of TGF-β on immune activation and mechanism thereof. Due to the immunomodulatory effect of TGF-β, small molecule TGF-βR1 inhibitors alone or in combination with PD-(L)1 monoclonal antibody have great application prospects in the treatment of a variety of solid tumors.

Patent application WO2002094833A1 of Eli Lilly and company reports that compound A (i.e., LY2157299 or Galunisertib) has TGF-β inhibitory activity. The compound can inhibit invasion and metastasis of tumor cells, and inhibit tumor cell infiltrating into blood vessels at the same time. There are currently many clinical trials in progress, which are the most advanced compounds in the field. Another patent application WO2016057278A1 of Eli Lilly and Company reports that compound B (i.e., LY3200882) is a small molecule inhibitor of TGF-β newly developed by the company. Phase I clinical trials of the compound in combination with PD-L1 to treat solid tumors are in process.

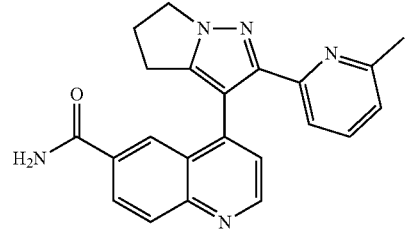

Compound A

-continued

Compound B

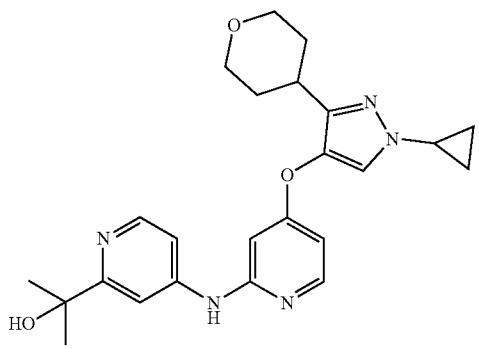

Content of the Present Invention

In one aspect, the present disclosure provides a compound represented by formula (I), a pharmaceutically acceptable salt thereof or an isomer thereof, (I)

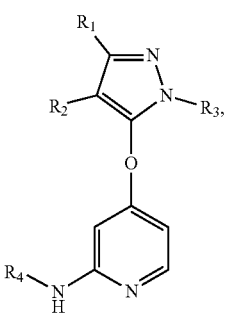

wherein, $R_1$ and $R_2$ are each independently H, F, Cl, Br, —CN,

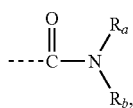

$C_{1-3}$ alkoxy, $C_{1-3}$ alkyl or $C_{3-6}$ cycloalkyl, wherein the $C_{1-3}$ alkoxy, $C_{1-3}$ alkyl and $C_{3-6}$ cycloalkyl are optionally substituted by 1, 2 or 3 substituents independently selected from F or Cl;

Or $R_1$ and $R_2$ together with the carbon atom to which they are attached to, so that

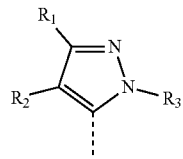

is selected from

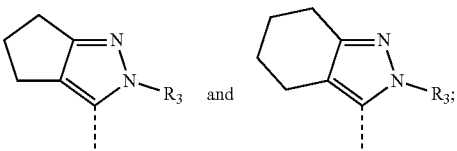

$R_3$ is $C_{1-6}$ alkyl, 5-6 membered heteroaryl, phenyl or 5-6 membered heterocycloalkyl, wherein the $C_{1-6}$ alkyl, 5-6 membered heteroaryl, phenyl and 5-6 membered heterocycloalkyl are optionally substituted by 1, 2 or 3 $R_c$;

Each $R_c$ is independently H, F, Cl, Br, I, —CN, —OH, $C_{1-3}$ alkoxy or $C_{1-3}$ alkyl;

$R_4$ is 5-6 membered heteroaryl or phenyl, wherein the 5-6 membered heteroaryl and phenyl are optionally substituted by 1, 2 or 3 $R_d$;

Each $R_d$ is independently H, —CN,

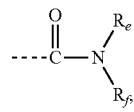

$C_{1-6}$ alkoxy or $C_{1-6}$ alkyl optionally substituted by 1, 2 or 3 substitutes independently selected from F, Cl, Br, I, —OH, —OCH$_3$, —CN and NH$_2$;

$R_a$, $R_b$, $R_e$ and $R_f$ are each independently H, —CH$_3$, —CH$_2$CH$_3$, —CH$_2$CH$_2$CH$_3$ or —CH(CH$_3$)$_2$;

The 5-6 membered heteroaryl and 5-6 membered heterocycloalkyl respectively contain 1, 2, 3 or 4 heteroatoms independently selected from N, —O— and —S—.

In some embodiments of the present disclosure, the $R_1$ and $R_2$ are each independently H, F, Cl, Br, —CN,

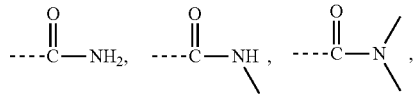

—OCH$_3$, —OCH$_2$CH$_3$, —CH$_3$, —CH$_2$CH$_3$, —CH(CH$_3$)$_2$,

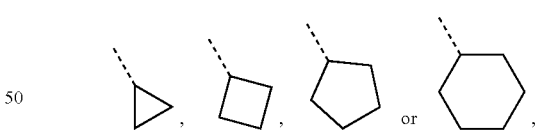

wherein the —OCH$_3$, —OCH$_2$CH$_3$, —CH$_3$, —CH$_2$CH$_3$, —CH(CH$_3$)$_2$, are optionally substituted by 1, 2 or 3 substitutes independently selected from F or Cl, other variables are as defined in the present disclosure.

In some embodiments of the present disclosure, the $R_1$ and $R_2$ are each independently H, F, Cl, Br, —CN,

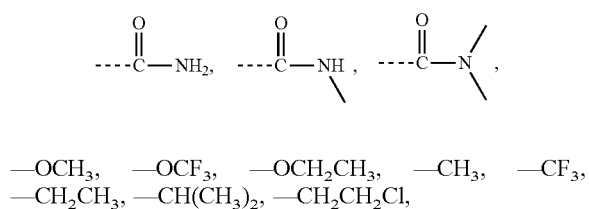

—OCH$_3$, —OCF$_3$, —OCH$_2$CH$_3$, —CH$_3$, —CF$_3$, —CH$_2$CH$_3$, —CH(CH$_3$)$_2$, —CH$_2$CH$_2$Cl,

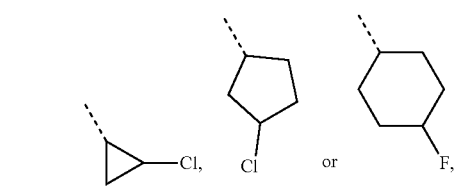

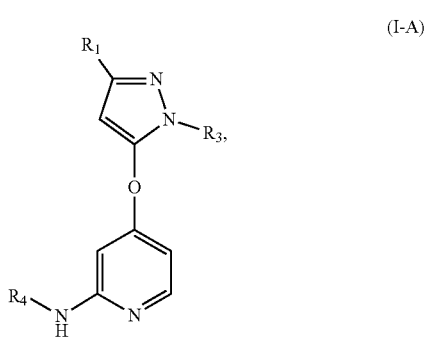

other variables are as defined in the present disclosure.

In some embodiments of the present disclosure, the compound has the structure represented by formula (I-A):

(I-A)

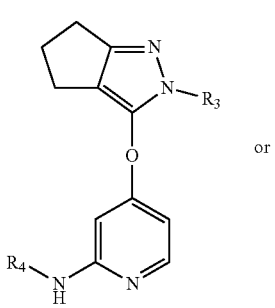

Wherein, the $R_1$, $R_3$ and $R_4$ are as defined in the present disclosure.

In some embodiments of the present disclosure, the compound has the structure represented by formula (I-B) or (I-C):

(I-B)

(I-C)

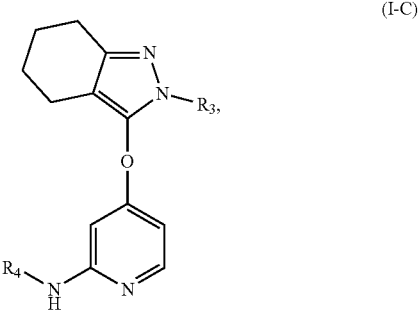

wherein, the $R_3$ and $R_4$ are as defined in the present disclosure.

In some embodiments of the present disclosure, each $R_c$ is independently H, F, Cl, Br, I, —CN, —OH, —OCH$_3$, —CH$_3$ or —CH$_2$CH$_3$, other variables are as defined in the present disclosure.

In some embodiments of the present disclosure, the $R_3$ is $C_{1-3}$ alkyl, pyridyl, phenyl or tetrahydro-2H-pyranyl, wherein the $C_{1-3}$ alkyl, pyridyl, phenyl and tetrahydro-2H-pyranyl are optionally substituted by 1, 2 or 3 $R_c$, $R_c$, and other variables are as defined in the present disclosure.

In some embodiments of the present disclosure, the $R_3$ is —C($R_c$)$_3$, —CH$_2$CH$_2$R$_e$,

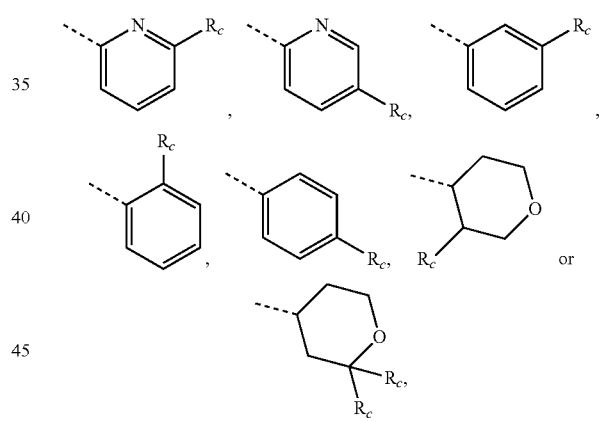

$R_c$ and other variables are as defined in the present disclosure.

In some embodiments of the present disclosure, the $R_3$ is —CH$_3$, —CF$_3$, —CH$_2$CH$_3$, —CH$_2$CH$_2$F,

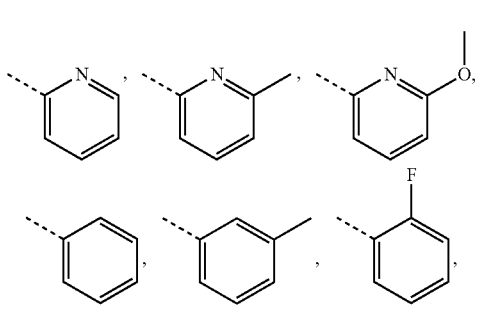

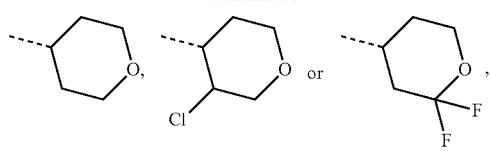

other variables are as defined in the present disclosure.

In some embodiments of the present disclosure, the compound has the structure represented by formula (I-A1)-(I-A3):

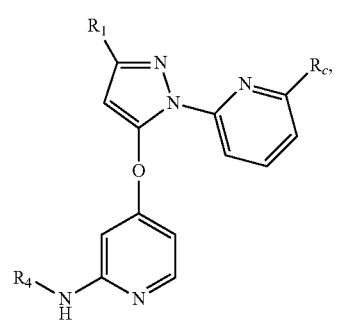

(I-A1)

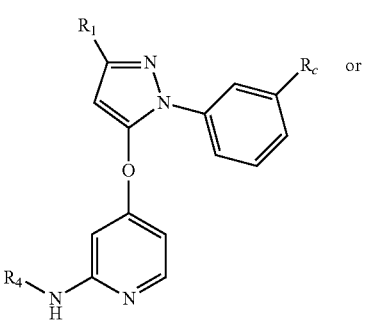

(I-A2)

or

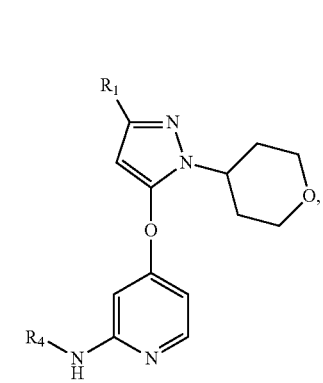

(I-A3)

wherein, the each $R_c$, $R_1$ and $R_4$ are as defined in the present disclosure.

In some embodiments of the present disclosure, the compound has the structure represented by formula (I-B1)-(I-B3) or (I-C1)-(I-C3):

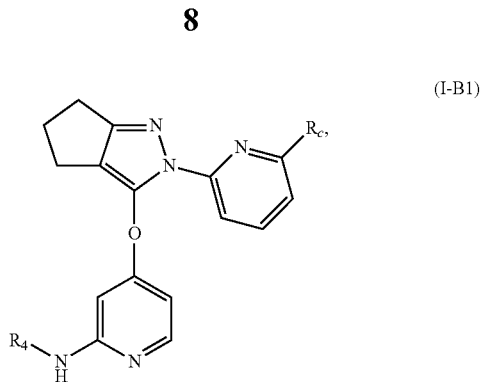

(I-B1)

(I-B2)

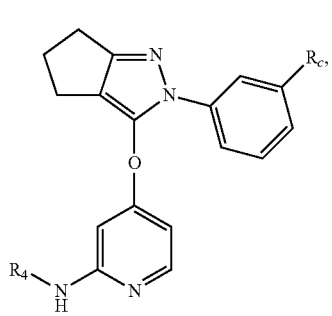

(I-B3)

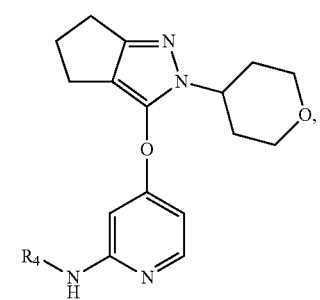

(I-C1)

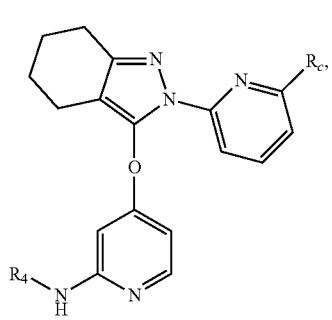

(I-C2)

or

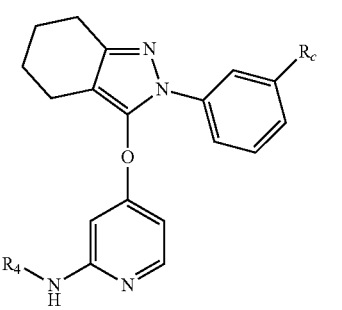

-continued (I-C3)

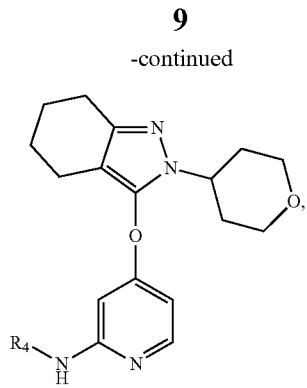

wherein, the each $R_c$ and $R_4$ are as defined in the present disclosure.

In some embodiments of the present disclosure, the each $R_d$ is independently H, —CN,

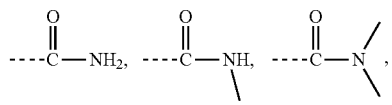

$C_{1-3}$ alkoxy or $C_{1-4}$ alkyl optionally substituted by 1, 2 or 3 substituents independently selected from F, Cl, Br, I, —OH, —OCH$_3$, —CN and NH$_2$, others variables are as defined in the present disclosure.

In some embodiments of the present disclosure, each $R_d$ is independently H, —CN,

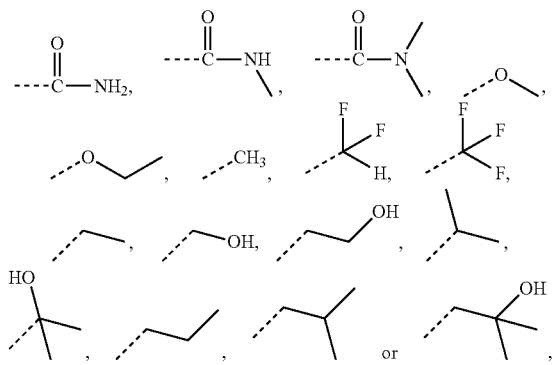

other variables are as defined in the present disclosure.

In some embodiments of the present disclosure, the $R_4$ is pyrrolyl, pyrazolyl, pyridyl, pyrazinyl, pyrimidinyl or phenyl, wherein the pyrrolyl, pyrazolyl, pyridyl, pyrazinyl, pyrimidinyl and phenyl are optionally substituted by 1, 2 or 3 $R_d$, $R_d$ and other variables are as defined in the present disclosure.

In some embodiments of the present disclosure, the $R_4$ is

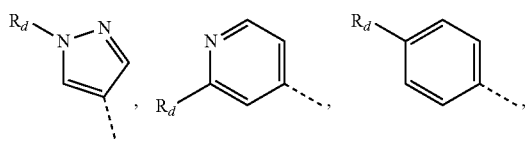

-continued

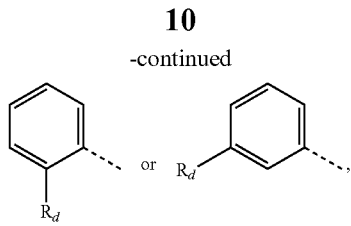

$R_d$ and other variables are as defined in the present disclosure.

In some embodiments of the present disclosure, the $R_4$ is

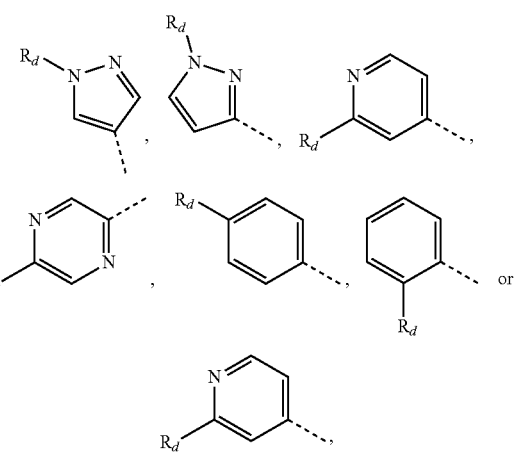

$R_d$ and other variables are as defined in the present disclosure.

In some embodiments of the present disclosure, the $R_4$ is

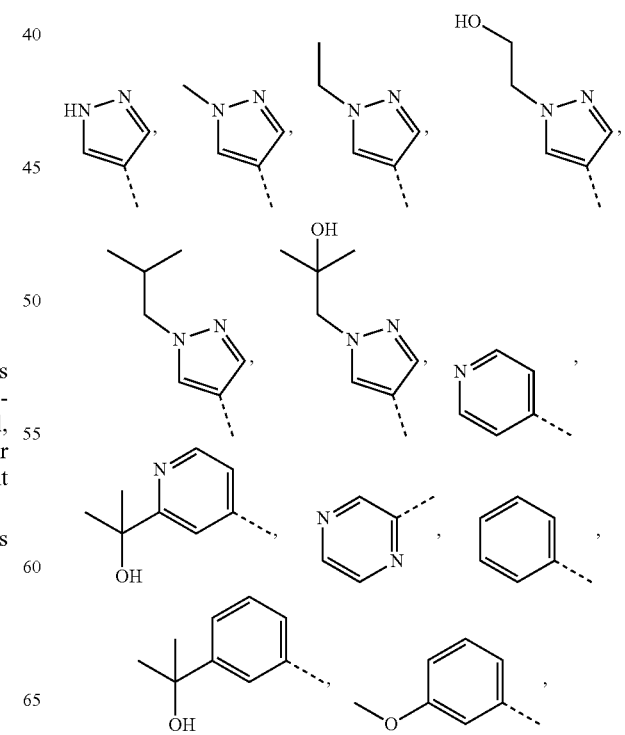

-continued
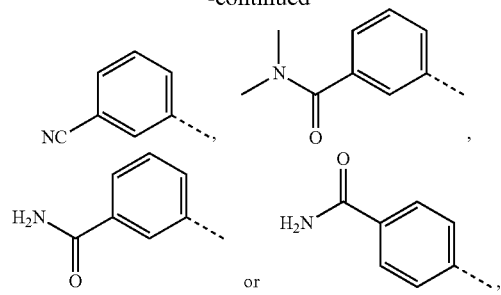
other variables are as defined in the present disclosure.
In some embodiments of the present disclosure, the $R_4$ is
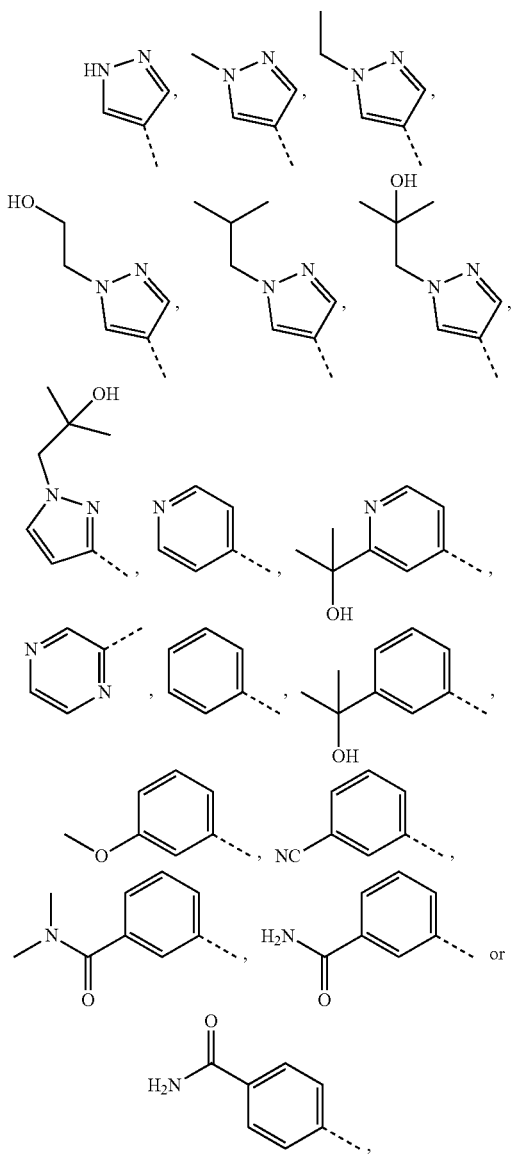
other variables are as defined in the present disclosure.
In some embodiments of the present disclosure, the compound has the structure represented by formula (I-A4)-(I-A15).
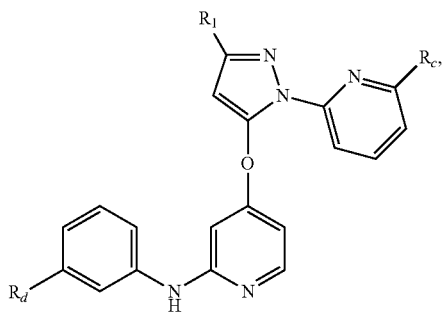
(I-A4)
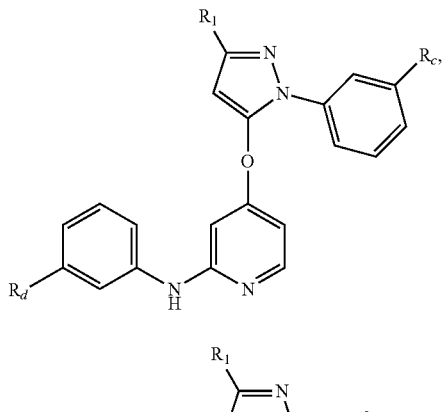
(I-A5)
(I-A6)
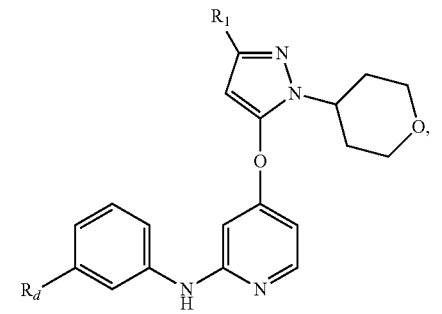
(I-A7)
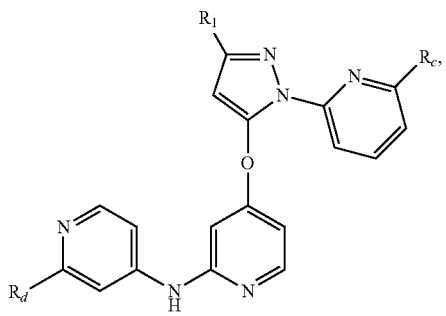
(I-A8)
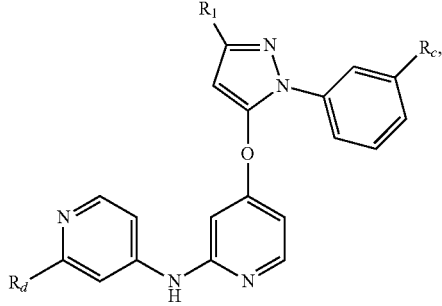

(I-A9)
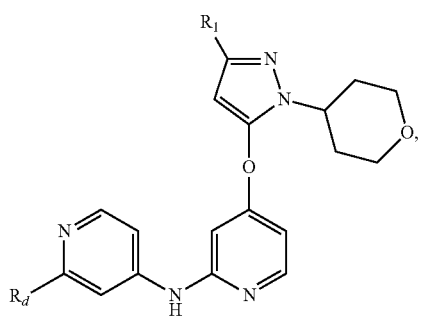
(I-A10)
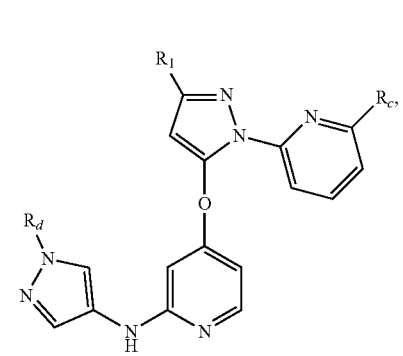
(I-A11)
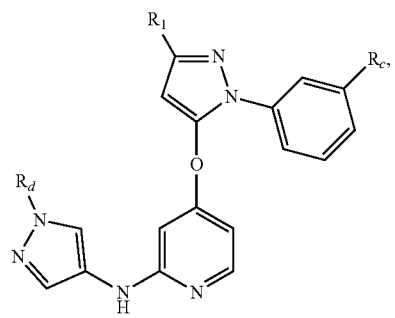
(I-A12)
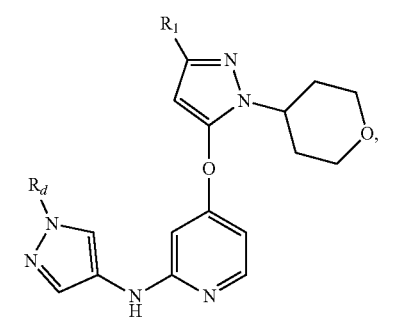
(I-A13)
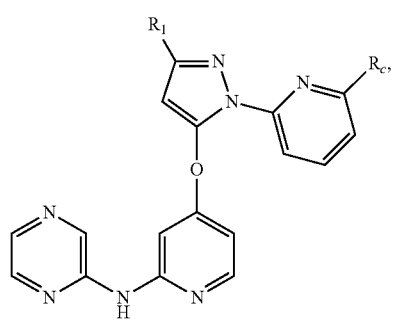
(I-A14)
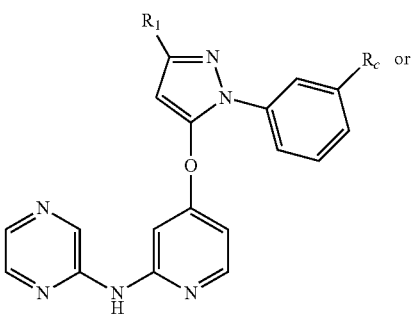
or
(I-A15)
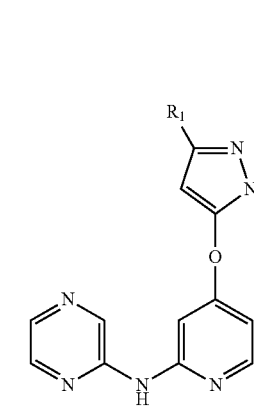
wherein, the each $R_c$, $R_1$ and $R_d$ are as defined in the present disclosure.
In some embodiments of the present disclosure, the compound has the structure represented by formula (I-B4)-(I-B6) or (I-C4)-(I-C6):
(I-B4)
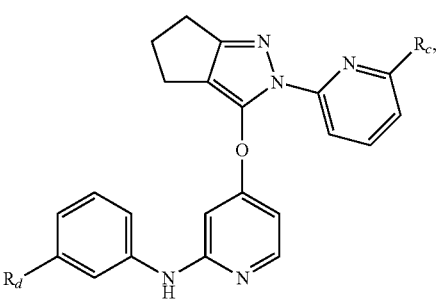
(I-B5)
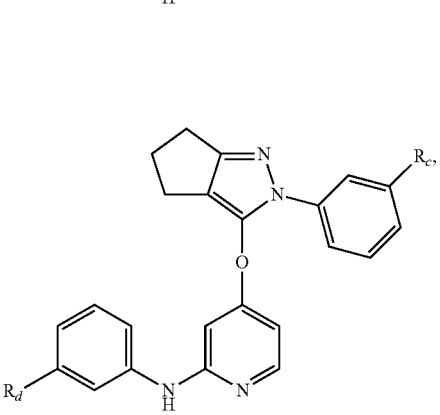

-continued

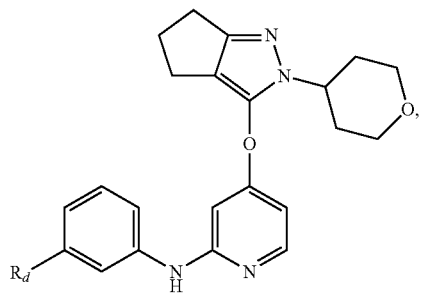 (I-B6)

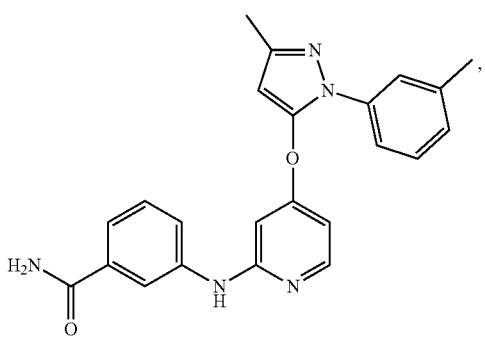

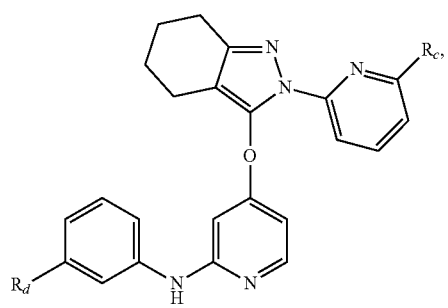 (I-C4)

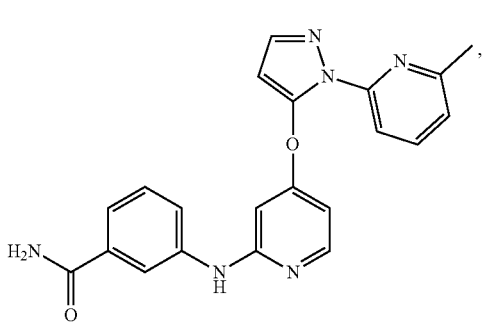

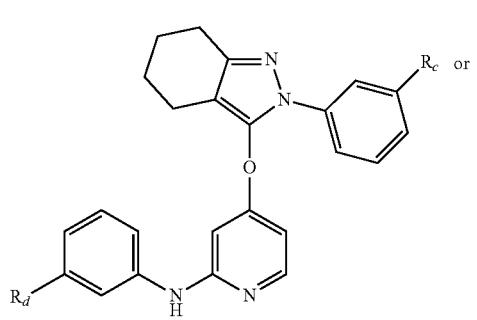 (I-C5) or

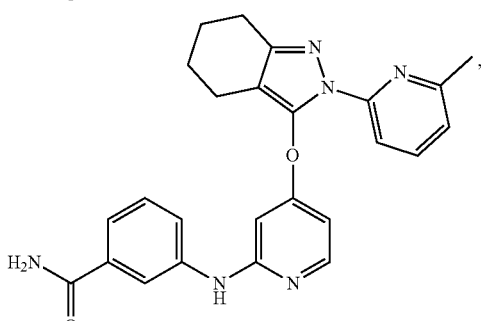

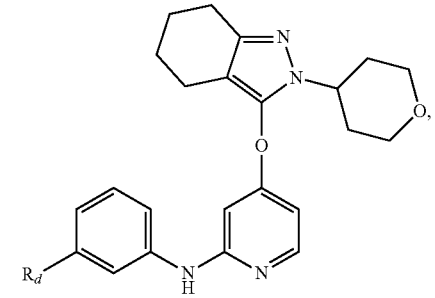 (I-C6)

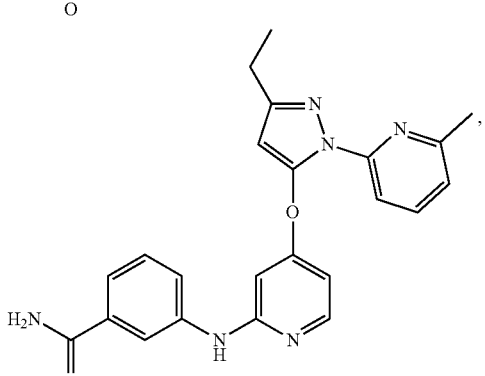

wherein, the each $R_c$ and $R_d$ are as defined in the present disclosure.

There are also some embodiments of the present disclosure which are derived from any combination of the above variables.

The present disclosure also provides compounds represented by the following formulas, pharmaceutically acceptable salts thereof or isomers thereof:

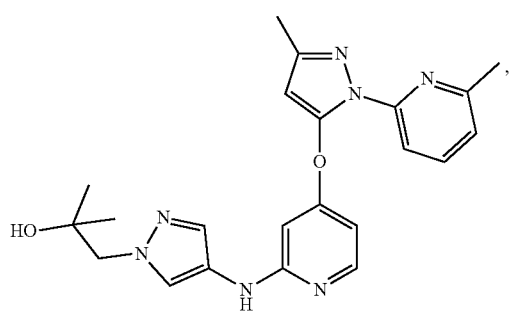

17
-continued
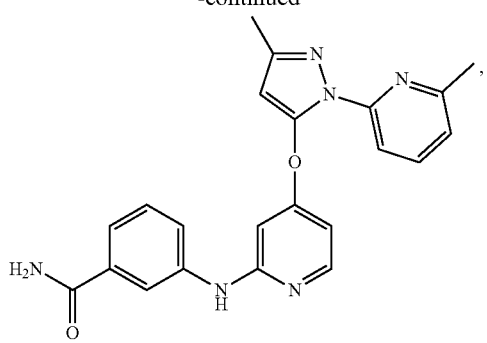
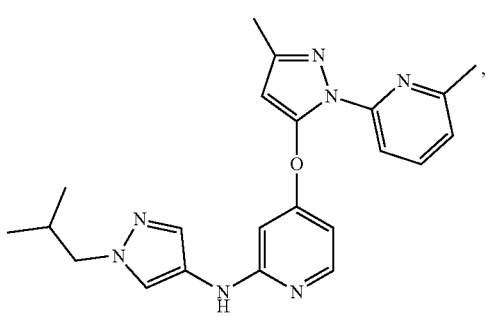
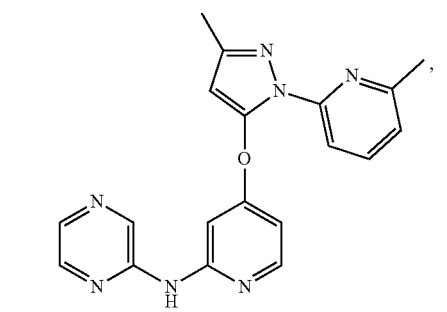
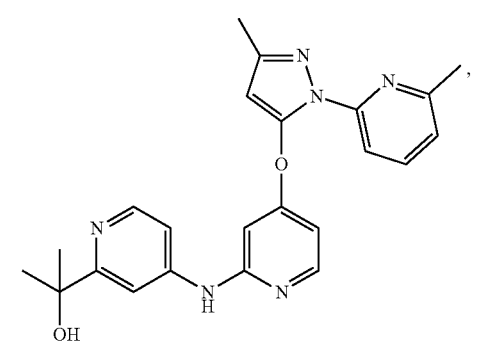
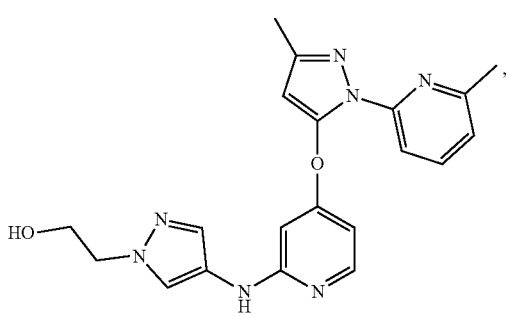
18
-continued
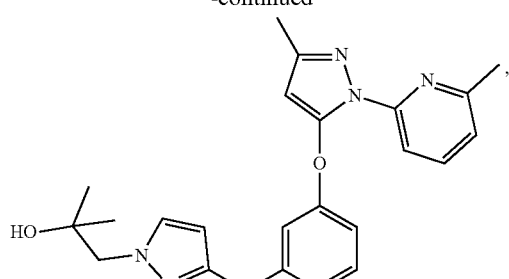
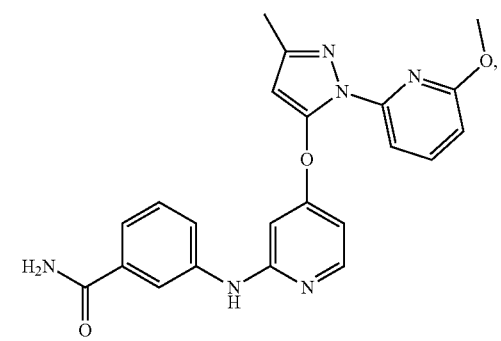
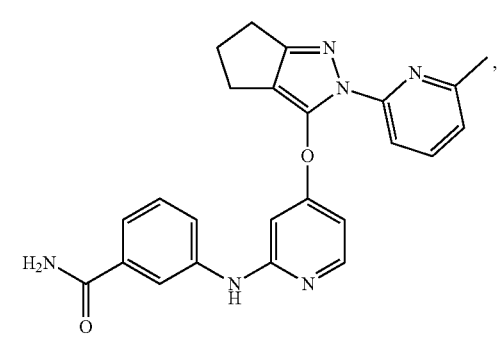
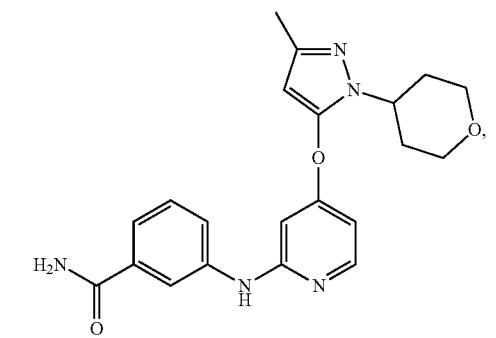
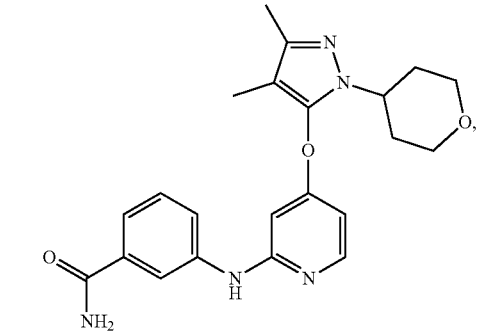

In the other aspect, the present disclosure provides a use of the compound, the pharmaceutically acceptable salt thereof or the isomer thereof in the preparation of TGF-βR1 inhibitor medicament. The present disclosure also provides a use of the compound, the pharmaceutically acceptable salt thereof or the isomer thereof in the preparation of solid tumor medicament.

In another aspect, the present disclosure provides a pharmaceutical composition containing a therapeutically effective amount of the compound, the pharmaceutically acceptable salt thereof or the isomer thereof, and a pharmaceutically acceptable carrier.

Technical Effect

The compounds of the present disclosure exhibit significant inhibition of the downstream signal of TGF-β in cells, and excellent pharmacokinetics, pharmacodynamic properties and in vivo drug efficacy at the same time.

The compounds of the present disclosure have excellent pSmad inhibitory activity in vitro. At the same time, the compounds of the present disclosure exhibit excellent pharmacokinetic properties. Both in pharmacokinetic experiments in mice in vivo and drug efficacy trials of continuous administration in vivo, the compounds exhibit excellent system exposure, suggesting that the compounds of the present disclosure can be well absorbed clinically and reach a higher exposure, further increasing the target occupancy rate and inhibition rate, and further ensuring the efficacy of the drug. The compounds of the present disclosure unexpectedly exhibit excellent tumor growth inhibition rate in the mouse CT26 model, suggesting that the compounds of the present disclosure have excellent drug efficacy clinically. Moreover, the compounds of the present disclosure exhibit extremely high drug concentration in tumor tissue, suggesting that the compounds of the present disclosure have a better tissue distribution and are more advantageous in the treatment of solid tumors.

Definition and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and "(±)" refers to racemic.

Unless otherwise specified, the absolute configuration of a stereogenic center is represented by a wedged solid bond ( ◢ ) and a wedged dashed bond ( ⋰ ), and a wave line ( ⌒ ) is used to represent a wedged solid bond ( ◢ ) or a wedged dashed bond ( ⋰ ).

Unless otherwise specified, when double bond structure, such as carbon-carbon double bond, carbon-nitrogen double bond, and nitrogen-nitrogen double bond, exists in the compound, and each of the atoms on the double bond is connected to two different substituents (including the condition where a double bond contains a nitrogen atom, the lone pair of electrons attached on the nitrogen atom is regarded as a substituent connected), if the atom on the double bond in the compound is connected to its substituent by a wave line ( ⌒ ), this refers to the (Z) isomer, (E) isomer or a mixture of two isomers of the compound. For example, the following formula (A) means that the compound exists as a single isomer of formula (A-1) or formula (A-2) or as a mixture of two isomers of formula (A-1) and formula (A-2); the following formula (B) means that the compound exists in the form of a single isomer of formula (B-1) or formula (B-2) or in the form of a mixture of two isomers of formula (B-1) and formula (B-2). The following formula (C) means that the compound exists as a single isomer of formula (C-1) or formula (C-2) or as two a mixture of two isomers of formula (C-1) and formula (C-2).

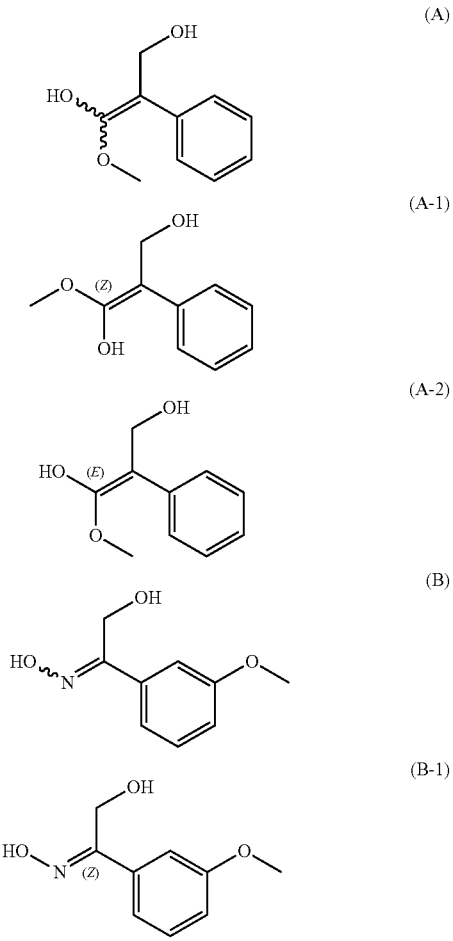

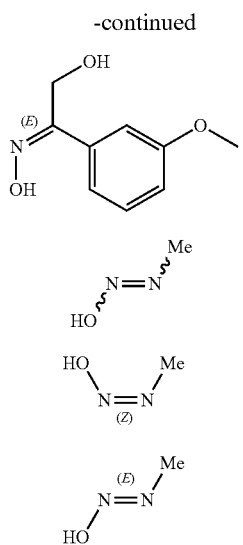

Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

For a medicament or a pharmacologically active agent, the term "effective amount" or "therapeutically effective amount" refers to a nontoxic but sufficient amount to achieve a desired effect of the medicament or the agent. For the oral dosage form of the present disclosure, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled person in the art based on routine experiment.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to more than one atom on a ring, such substituent can be bonded to any atom of the ring. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

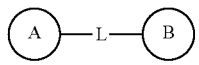

is -M-W—, then -M-W— can link ring A and ring B to form

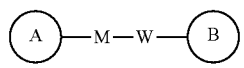

in the direction same as left-to-right reading order, and form

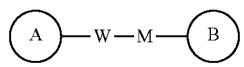

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. The chemical bond between the site and other groups can be represented by a straight solid bond ( ╱ ), a straight dashed bond ( ╱ ) or a wavy line ( ╲ ). For example, the straight solid bond in —OCH$_3$ means that it is linked to other groups through the oxygen atom in the group; the straight dashed bonds in

mean that it is linked to other groups through the two ends of nitrogen atom in the group; the wave lines in

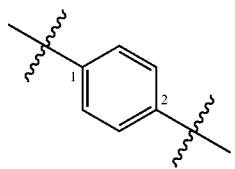 [SMILES: *c1ccc(*)cc1]

mean that the phenyl group is linked to other groups through carbon atoms at position 1 and position 2.

Unless otherwise specified, the number of atoms in a ring is generally defined as the number of ring members. For example, "5-7 membered ring" refers to a "ring" in which 5 to 7 atoms are arranged around.

Unless otherwise specified, the term "5-6 membered ring" refers to a cycloalkyl, heterocycloalkyl, cycloalkenyl, heterocycloalkenyl, cycloalkynyl, heterocycloalkynyl, aryl or heteroaryl having 5 to 6 ring atoms. The ring includes single ring, and also includes spiro ring, fused ring, and bridged ring. Unless otherwise specified, the ring optionally includes 1, 2 or 3 heteroatoms independently selected from O, S and N. The 5-6 membered ring includes 5 membered, 6 membered rings, etc. "5-6 membered ring" includes, for example, phenyl, pyridyl and piperidinyl, etc.; on the other hand, the term "5-6 membered heterocycloalkyl" includes piperidyl, but excluding phenyl. The term "ring" also includes a ring system containing at least one ring, wherein each "ring" independently meets the above definition.

Unless otherwise specified, the term "$C_{1-6}$ alkyl" refers to a linear or branched saturated hydrocarbon group containing 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl groups and the like. It can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, and t-butyl), pentyl (including n-pentyl, isopentyl and neopentyl), hexyl, etc.

Unless otherwise specified, the term "$C_{1-4}$ alkyl" refers to a linear or branched saturated hydrocarbon group containing 1 to 4 carbon atoms. The $C_{1-4}$ alkyl includes $C_{1-2}$, $C_{1-3}$ and $C_{2-3}$ alkyl groups and the like. It can be monovalent (such as methyl), divalent (such as methylene) or multivalent (such as methine). Examples of $C_{1-4}$ alkyl include but are not limited to methyl (Me), ethyl (Et), propyl (including n-propyl and isopropyl), butyl (including n-butyl, isobutyl, s-butyl, and t-butyl), etc.

Unless otherwise specified, the term "$C_{1-3}$ alkyl" refers to a linear or branched saturated hydrocarbon group having 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "$C_{1-6}$ alkoxy" refers to an alkyl group containing 1 to 6 carbon atoms that are connected to the rest of the molecule through an oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$ and $C_3$ alkoxy, etc. Examples of $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentoxy (including n-pentoxy, isopentoxy and neopentoxy), hexoxy, etc.

Unless otherwise specified, the term "$C_{1-4}$ alkoxy" refers to an alkyl group containing 1 to 4 carbon atoms that are connected to the rest of the molecule through an oxygen atom. The $C_{1-4}$ alkoxy includes $C_{1-3}$, $C_{1-2}$, $C_{2-4}$, $C_4$ and $C_3$ alkoxy, etc. Examples of $C_{1-6}$ alkoxy include, but are not limited to, methoxy, ethoxy, propoxy (including n-propoxy and isopropoxy), butoxy (including n-butoxy, isobutoxy, s-butoxy and t-butoxy), pentoxy (including n-pentoxy, isopentoxy and neopentoxy), hexoxy, etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and isopropoxy), etc.

Unless otherwise specified, the term "halo" or "halogen" by itself or as part of another substituent refers to fluorine, chlorine, bromine or iodine atom.

Unless otherwise specified, "$C_{3-6}$ cycloalkyl" refers a saturated cyclic hydrocarbon group containing 3 to 6 carbon atoms, which includes monocyclic and bicyclic systems. $C_{3-6}$ cycloalkyl includes $C_{3-5}$, $C_{4-5}$ and $C_{5-6}$ cycloalkyl, etc. And it may be monovalent, divalent, or multivalent. Examples of $C_{3-6}$ cycloalkyl include, but are not limited to, cyclopropyl, cyclobutyl, cyclopentyl, cyclohexyl and the like.

Unless otherwise specified, "$C_{5-6}$ cycloalkyl" refers a saturated cyclic hydrocarbon group containing 5 to 6 carbon atoms, which includes monocyclic and bicyclic systems. $C_{5-6}$ cycloalkyl includes $C_5$ and $C_6$ cycloalkyl, etc. And it may be monovalent, divalent, or multivalent. Examples of $C_{5-6}$ cycloalkyl include, but are not limited to, cyclopentyl, cyclohexyl and the like.

Unless otherwise specified, the term "5-6 membered heterocycloalkyl" by itself or in combination with other terms respectively refers to a saturated cyclic group having 5 to 6 ring atoms, with 1, 2, 3 or 4 ring atoms being heteroatoms independently selected from O, S and N, and the rest are carbon atoms, wherein the N atom is optionally quaternized, and the N and S heteroatoms may optionally be oxidized (i.e., NO and $S(O)_p$, p is 1 or 2). It includes monocyclic and bicyclic systems, wherein bicyclic system includes spiro ring, fused ring, and bridged ring. In addition, with regard to the "5-6 membered heterocycloalkyl", a heteroatom may occupy the linking position of the heterocycloalkyl with the rest of the molecule. The 5-6 membered heterocycloalkyl includes 5 membered and 6 membered heterocycloalkyl. Examples of 5-6 membered heterocycloalkyl include, but are not limited to, pyrrolidinyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidyl (including 1-piperidyl, 2-piperidyl and 3-piperidyl, etc.), piperazinyl (including 1-piperazinyl and 2-piperazinyl, etc.), morpholinyl (including 3-morpholinyl and 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl or homopiperidinyl.

Unless otherwise specified, the terms "$C_{6-12}$ aromatic ring" and "$C_{6-12}$ aryl" can be used interchangeably in the present disclosure, and the term "$C_{6-12}$ aromatic ring" or "$C_{6-12}$ aryl" refers to a cyclic hydrocarbon group containing 6 to 12 carbon atoms, having a conjugated π-electron system, it can be a single ring, a fused bicyclic ring or a fused tricyclic ring system, wherein each ring is aromatic. It can be monovalent, divalent or multivalent, $C_{6-12}$ aryl groups include $C_{6-10}$, $C_{6-9}$, $C_{6-8}$, $C_{12}$, $C_{10}$ and $C_6$ aryl groups, etc. Examples of $C_{6-12}$ aryl groups include, but are not limited to, phenyl, naphthyl (including 1-naphthyl and 2-naphthyl).

Unless otherwise specified, the terms "$C_{6-10}$ aromatic ring" and "$C_{6-10}$ aryl" can be used interchangeably in the present disclosure, and the term "$C_{6-10}$ aromatic ring" or "$C_{6-10}$ aryl" refers a cyclic hydrocarbon group containing 6 to 10 carbon atoms, having a conjugated π-electron system, it can be a single ring, a fused bicyclic ring or a fused tricyclic ring system, wherein each ring is aromatic. It can be monovalent, divalent or multivalent, $C_{6-10}$ aryl groups include $C_{6-9}$, $C_9$, $C_{10}$ and $C_6$ aryl groups, etc. Examples of $C_{6-10}$ aryl groups include, but are not limited to, phenyl, naphthyl (including 1-naphthyl and 2-naphthyl).

Unless otherwise specified, the terms "5-6 membered heteroaromatic ring" and "5-6 membered heteroaryl" can be used interchangeably in the present disclosure. The term "5-6 membered heteroaryl" refers to a monocyclic group having 5 or 6 ring atoms, having a conjugated π-electron system, with 1, 2, 3 or 4 ring atoms being heteroatoms independently selected from O, S and N, and the rest are carbon atoms, wherein the N atom is optionally quaternized, and the N and S heteroatoms may optionally be oxidized (i.e., NO and $S(O)_p$, p is 1 or 2). The 5-6 membered heteroaryl can be connected to the rest of the molecule through a heteroatom or a carbon atom. The 5-6 membered heteroaryl includes 5 membered and 6 membered heteroaryl groups. Examples of the 5-6 membered heteroaryl group include, but are not limited to, pyrrolyl (including N-pyrrolyl, 2-pyrrolyl and 3-pyrrolyl, etc.), pyrazolyl (including 2-pyrazolyl and 3-pyrazolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furanyl (including 2-furyl and 3-furyl, etc.), thienyl (including 2-thienyl and 3-thienyl, etc.), pyridyl (including 2-pyridyl, 3-pyridyl and 4-pyridyl, etc.), pyrazinyl or pyrimidinyl (including 2-pyrimidinyl and 4-pyrimidinyl, etc.).

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n membered to n+m membered means that the number of atoms on the ring is from n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, and any range from n to n+m is also included, for example, 3-12 membered ring includes 3-6 membered ring, 3-9 membered ring, 5-6 membered ring, 5-7 membered ring, 6-7 membered ring, 6-8 membered ring, and 6-10 membered ring, etc.

The term "leaving group" refers to a functional group or atom which can be replaced by another functional group or atom through a substitution reaction (such as affinity substitution reaction). For example, representative leaving groups include triflate; chlorine, bromine, and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl)methyl; silyl, such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS) and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The solvents used in the present disclosure are commercially available.

The present disclosure uses the following abbreviations: CDCl$_3$ refers to deuterated chloroform; DMSO refers to dimethyl sulfoxide; Boc refers to tert-butoxycarbonyl.

The compounds of the present disclosure are named according to the conventional naming principles in the art or by ChemDraw® software, and the commercially available compounds use the supplier catalog names.

DETAILED DESCRIPTION OF THE PREFERRED EMBODIMENT

The following embodiments further illustrate the present disclosure, but the present disclosure is not limited thereto. The present disclosure has been described in detail herein, and its specific embodiments have also been disclosed, for those skilled in the art, it is obvious to make various modifications and improvements to the embodiments of the present disclosure without departing from the spirit and scope of the present disclosure.

Embodiment 1: Compound 1

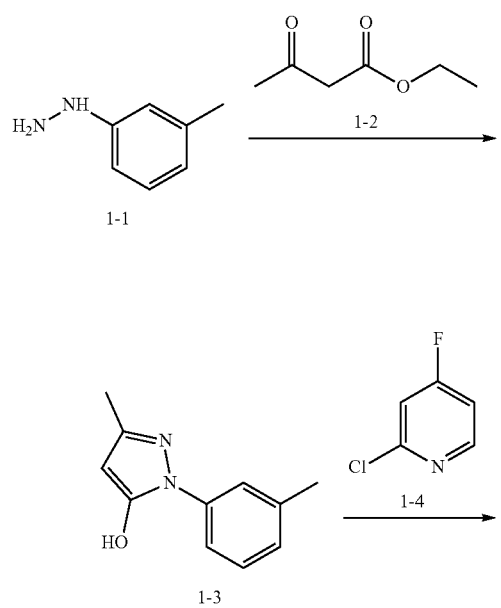

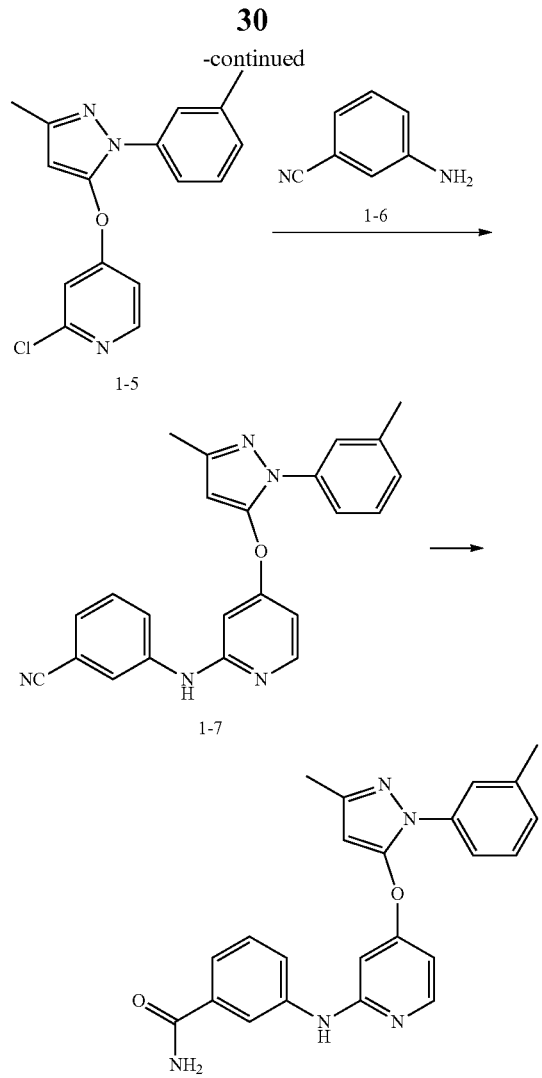

Step A: Compound 1-1 (4.7 g, 38.47 mmol, 1 eq) and 1-2 (5.26 g, 40.40 mmol, 5.10 mL, 1.05 eq) were dissolved in acetic acid (40 mL) and reacted at 80° C. for 12 hours. After the reaction was completed, the mixed solution was concentrated in vacuum to remove the solvent, diluted with water (100 mL) and pH value was adjusted to 7 with saturated sodium bicarbonate aqueous solution, then the mixture was extracted with ethyl acetate (100 mL×2). The organic phases were combined, washed with saturated brine (100 mL), dried over anhydrous sodium sulfate, filtered, concentrated, and purified by column separation to obtain compound 1-3. MS (ESI) m/z: 189.1 [M+H$^+$].

Step B: Compound 1-3 (1 g, 5.31 mmol, 1 eq) and 1-4 (768.70 mg, 5.84 mmol, 1.1 eq) were dissolved in N,N-dimethylformamide (10 mL), and potassium carbonate (2.20 g, 15.94 mmol, 3 eq) was added, reacted at 120° C. for 6 hours. The reaction mixture was diluted with water (60 mL), extracted with ethyl acetate (70 mL×2). The organic phases were combined and washed with saturated brine (60 mL), dried over anhydrous sodium sulfate, filtered, concentrated, and purified by column separation to obtain compound 1-5. MS (ESI) m/z: 300.1 [M+H$^+$].

Step C: 1-5 (0.77 g, 2.57 mmol, 1 eq), 1-6 (333.81 mg, 2.83 mmol, 96.31 μL, 1.1 eq), 4,5-bis(diphenylphosphino)-

9,9-dimethylxanthene (148.63 mg, 256.88 μmol, 0.1 eq), cesium carbonate (2.51 g, 7.71 mmol, 3 eq) and palladium acetate (57.67 mg, 256.88 μmol, 0.1 eq) were dissolved in dioxane (10 mL) and reacted at 100° C. for 3 hours under nitrogen atmosphere. The reaction mixture was diluted with water (40 mL) and extracted with ethyl acetate (70 mL×2). The organic phases were combined, washed with saturated brine (60 mL), dried over anhydrous sodium sulfate, filtered, and concentrated to obtain compound 1-7. MS (ESI) m/z: 382.3 [M+H$^+$].

Step D: Sodium hydroxide (140.52 mg, 3.51 mmol, 1 eq) was dissolved in water (2 mL), methanol (20 mL) was added and then compound 1-7 (1.34 g, 3.51 mmol, 1 eq) and dimethyl sulfoxide (411.72 mg, 5.27 mmol, 411.72 μL, 1.5 eq) were added. Hydrogen peroxide (597.40 mg, 5.27 mmol, 506.27 μL, concentration 30%, 1.5 eq) was dissolved in water (0.5 mL), then added dropwise into the previous reaction solution and the reaction was carried out at 25° C. for 2 hours. The reaction mixture was diluted with water (100 mL) and extracted with dichloromethane (100 mL×2). The organic phases were combined, washed with water (100 mL), dried over anhydrous sodium sulfate, filtered, concentrated, and purified by preparative high performance liquid chromatography (formic acid condition) to obtain compound 1. MS (ESI) m/z: 400.2 [M+H$^+$].

$^1$H NMR (400 MHz, DMSO-d$_6$) δ=9.23 (s, 1H), 8.10 (d, J=6.0 Hz, 1H), 8.02 (t, J=1.6 Hz, 1H), 7.88-7.77 (m, 2H), 7.41 (s, 1H), 7.39-7.29 (m, 4H), 7.27 (br d, J=4.0 Hz, 1H), 7.15-7.10 (m, 1H), 6.57 (dd, J=2.4, 6.0 Hz, 1H), 6.43 (d, J=2.4 Hz, 1H), 6.13 (s, 1H), 2.32 (s, 3H), 2.28-2.24 (m, 3H).

Embodiment 2: Compound 2

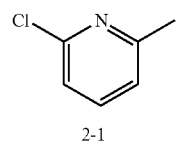

2-1

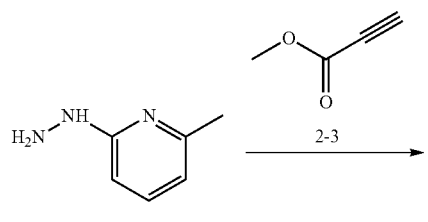

2-2

2-3

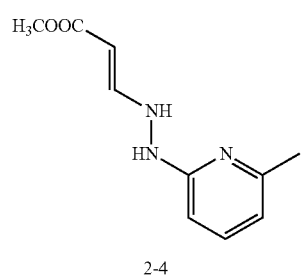

2-4

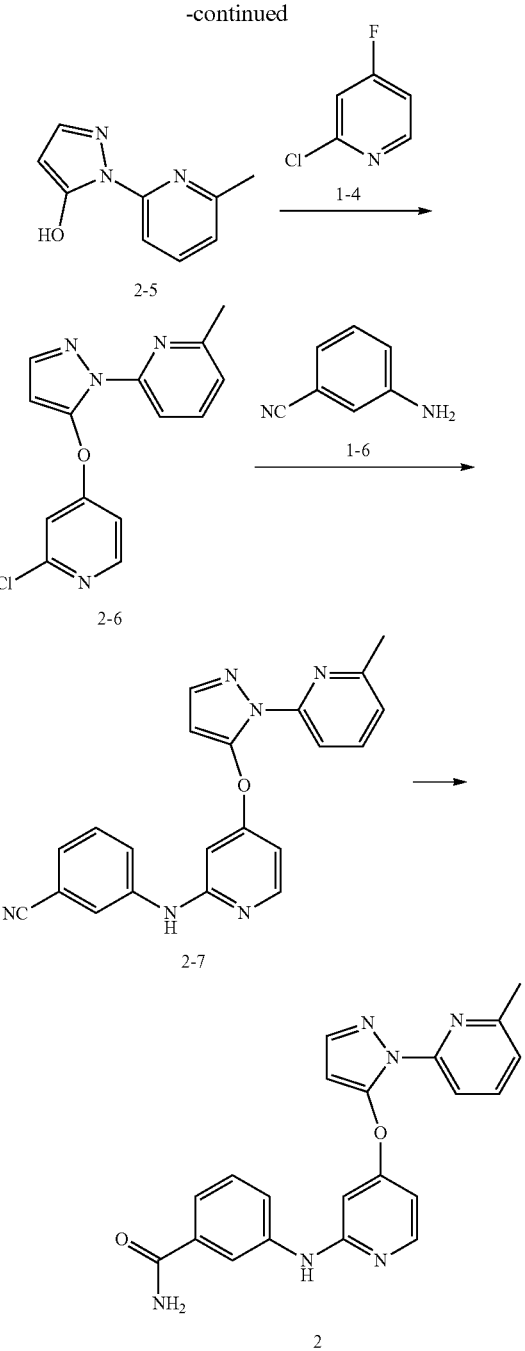

Step A: Compound 2-1 (19 g, 148.94 mmol, 16.24 mL, 1 eq) was dissolved in hydrazine hydrate (59.26 g, 1.16 mol, 57.53 mL, 98% purity, 7.79 eq) and reacted at 120° C. for 30 hours under nitrogen atmosphere. The reaction solution was cooled to −10° C., and a large amount of white solid was precipitated out, filtered, and the filter cake was collected and dried in vacuum to obtain compound 2-2. MS (ESI) m/z: 124.1 [M+H$^+$].

Step B: 2-3 (15.26 g, 181.48 mmol, 15.11 mL, 1.5 eq) was dissolved in methanol (100 mL), a solution of 2-2 (14.9 g, 120.99 mmol, 1 eq) in methanol (60 mL) was added dropwise at 0° C., the reaction was carried out at 25° C. for 4 hours. Cooled to 25° C., the reaction solution was diluted with water (100 mL), and extracted with dichloromethane (200 mL×2). The organic phases were combined, washed with saturated brine (100 mL), dried over anhydrous sodium sulfate, filtered, and concentrated to obtain compound 2-4. MS (ESI) m/z: 208.0 [M+H$^+$].

Step C: Compound 2-4 (13.6 g, 65.63 mmol, 1 eq) was dissolved in methanol (136 mL), triethylamine (3.32 g, 32.81 mmol, 4.57 mL, 0.5 eq) was added, and reacted at 70° C. for 8 hours. The reaction solution was concentrated in vacuum to remove the solvent, diluted with water (100 mL), and extracted with dichloromethane (150 mL×2). The organic phases were combined, washed with saturated brine (80 mL), dried over anhydrous sodium sulfate, filtered, concentrated, and purified by column separation to obtain compound 2-5. MS (ESI) m/z: 176.0 [M+H$^+$].

Step D: 2-5 (1 g, 5.71 mmol, 1 eq) and 1-4 (825.91 mg, 6.28 mmol, 1.1 eq) were dissolved in N,N-dimethylformamide (10 mL), and then potassium carbonate (2.37 g, 17.12 mmol, 3 eq) was added to the reaction solution and reacted at 120° C. for 12 hours. The reaction mixture was diluted with water (60 mL) and extracted with ethyl acetate (70 mL×2). The organic phases were combined, washed with saturated brine (60 mL), dried over anhydrous sodium sulfate, filtered, concentrated, and purified by column separation to obtain compound 2-6. MS (ESI) m/z: 287.0 [M+H$^+$].

Step E: 2-6 (414 mg, 1.44 mmol, 1 eq), 1-6 (187.64 mg, 1.59 mmol, 96.31 μL, 1.1 eq), 4,5-bis(diphenylphosphino)-9,9-dimethylxanthene (83.55 mg, 144.39 μmol, 0.1 eq), cesium carbonate (1.41 g, 4.33 mmol, 3 eq) and palladium acetate (32.42 mg, 144.39 μmol, 0.1 eq) were dissolved in 1,4-dioxane (5 mL), and reacted at 100° C. for 3 hours under nitrogen atmosphere. The reaction mixture was diluted with water (40 mL) and extracted with ethyl acetate (70 mL×2). The organic phases were combined, washed with saturated brine (60 mL), dried over anhydrous sodium sulfate, filtered, and concentrated. Ethyl acetate (70 mL) was added to dissolve the crude product, mercapto silica gel (1 g) was added, and stirred for 1 hour at 25° C. After filtration, the filtrate was concentrated in vacuum to obtain compound 2-7. MS (ESI) m/z: 369.1 [M+H$^+$].

Step F: Sodium hydroxide (77.31 mg, 1.93 mmol, 1 eq) was dissolved in water (0.9 mL), ethanol (8 mL) was added, and compound 2-7 (712 mg, 1.93 mmol, 1 eq) and dimethyl sulfoxide (226.51 mg, 2.90 mmol, 226.51 μL, 1.5 eq) were added. Hydrogen peroxide (328.66 mg, 2.90 mmol, 78.53 μL, concentration 30%, 1.5 eq) was dissolved in water (0.3 mL), and added dropwise to the above reaction solution, reacted at 25° C. for 2 hours. The reaction mixture was diluted with water (100 mL) and extracted with ethyl acetate (100 mL×2). The organic phases were combined, washed with saturated brine (100 mL), dried over anhydrous sodium sulfate, filtered, concentrated, and purified by preparative high performance liquid chromatography (formic acid condition) to obtain compound 2. MS (ESI) m/z: 387.0 [M+H$^+$].

$^1$H NMR (400 MHz, DMSO-d$_6$) δ=10.09 (br s, 1H), 8.08 (br d, J=6.0 Hz, 1H), 7.98 (br s, 1H), 7.94-7.87 (m, 1H), 7.87-7.79 (m, 2H), 7.70-7.52 (m, 3H), 7.50-7.32 (m, 2H), 7.18 (br d, J=7.2 Hz, 1H), 6.71 (br d, J=5.2 Hz, 1H), 6.48 (br s, 2H), 2.25 (br s, 3H).

Embodiment 3: Compound 3

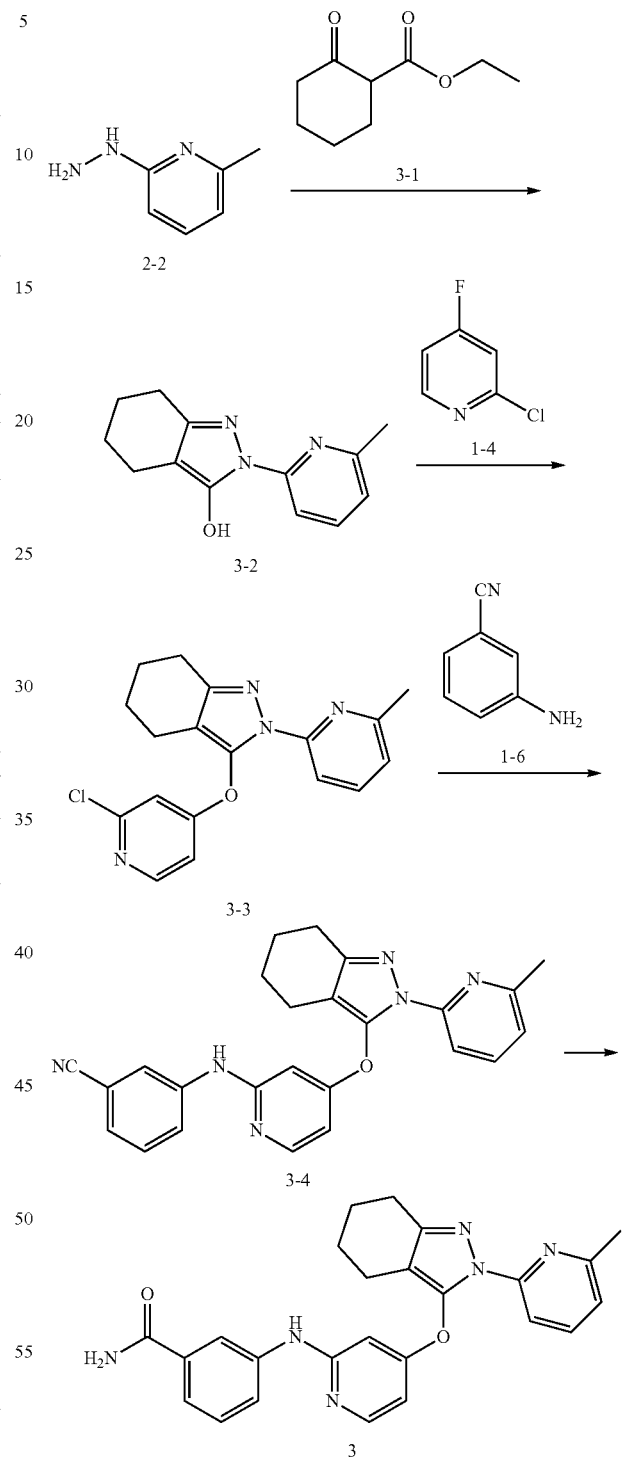

Step A: Compound 2-2 (3 g, 24.36 mmol, 1 eq) and 3-1 (4.15 g, 24.36 mmol, 3.91 mL, 1 eq) were dissolved in glacial acetic acid (30 mL) and reacted at 120° C. for 1 hour. The reaction solution was diluted with water (30 mL) and extracted with ethyl acetate (30 mL×2). The organic phases were combined, washed with saturated brine (10 mL×2), dried over anhydrous sodium sulfate, filtered, and concentrated to obtain compound 3-2. MS (ESI) m/z: 230.0 [M+H$^+$].

Step B: Compound 3-2 (1 g, 4.36 mmol, 1 eq) and 1-4 (860.54 mg, 6.54 mmol, 1.5 eq) were dissolved in N,N-dimethylformamide (10 mL), potassium carbonate (1.81 g, 13.08 mmol, 3 eq) was added under nitrogen atmosphere, and the reaction was carried out at 120° C. for 16 hours under nitrogen atmosphere. The reaction mixture was diluted with water (20 mL) and extracted with ethyl acetate (20 mL×2). The organic phases were combined, washed with saturated brine (60 mL), dried over anhydrous sodium sulfate, filtered, concentrated, and purified by column separation to obtain compound 3-3. MS (ESI) m/z: 341.1 [M+H$^+$].

Step C: Compound 3-3 (0.28 g, 821.58 μmol, 1 eq), 1-6 (97.06 mg, 821.58 μmol, 1 eq), 4,5-bis(diphenylphosphino)-9,9-dimethylxanthene (47.54 mg, 82.16 μmol, 0.1 eq), cesium carbonate (803.06 mg, 2.46 mmol, 3 eq) and palladium acetate (18.45 mg, 82.16 μmol, 0.1 eq) were dissolved in dioxane (3 mL) and reacted at 100° C. for 3 hours under nitrogen atmosphere. The reaction mixture was diluted with water (10 mL) and extracted with ethyl acetate (10 mL×2). The organic phases were combined, washed with saturated brine (30 mL), dried over anhydrous sodium sulfate, filtered, and concentrated to obtain compound 3-4. MS (ESI) m/z: 423.0 [M+H$^+$].

Step D: Compound 3-4 (0.13 g, 307.71 μmol, 1 eq), dimethyl sulfoxide (48.08 mg, 615.41 μmol, 48.08 μL, 2 eq) and sodium hydroxide (6.15 mg, 153.85 μmol, 0.5 eq) were dissolved in ethanol (2 mL), and hydrogen peroxide (52.33 mg, 461.56 μmol, 44.35 μL, 30% purity, 1.5 eq) was added dropwise, and reacted at 25° C. for 2 hours. The reaction solution was diluted with water (20 mL) and extracted with ethyl acetate (30 mL×2). The organic phases were combined, washed with saturated brine (60 mL), dried over anhydrous sodium sulfate, filtered, concentrated, and purified by preparative high performance liquid chromatography (formic acid condition) to obtain compound 3. MS (ESI) m/z: 441.2 [M+H$^+$].

$^1$H NMR (400 MHz, DMSO-d$_6$) δ ppm 1.68-1.76 (m, 2H) 1.78-1.86 (m, 2H) 2.22 (s, 3H) 2.35-2.41 (m, 2H) 2.65-2.70 (m, 3H) 6.26-6.32 (m, 1H) 6.46-6.53 (m, 1H) 7.06-7.12 (m, 1H) 7.22-7.32 (m, 2H) 7.33-7.38 (m, 1H) 7.45-7.50 (m, 1H) 7.72-7.87 (m, 3H) 8.00-8.04 (m, 1H) 8.06-8.12 (m, 1H) 9.11-9.16 (m, 1H).

Embodiment 4: Compound 4

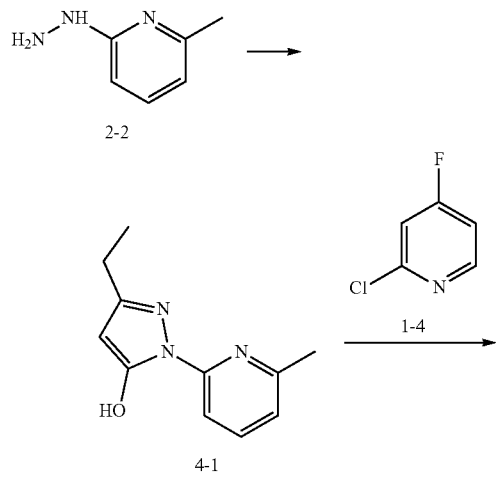

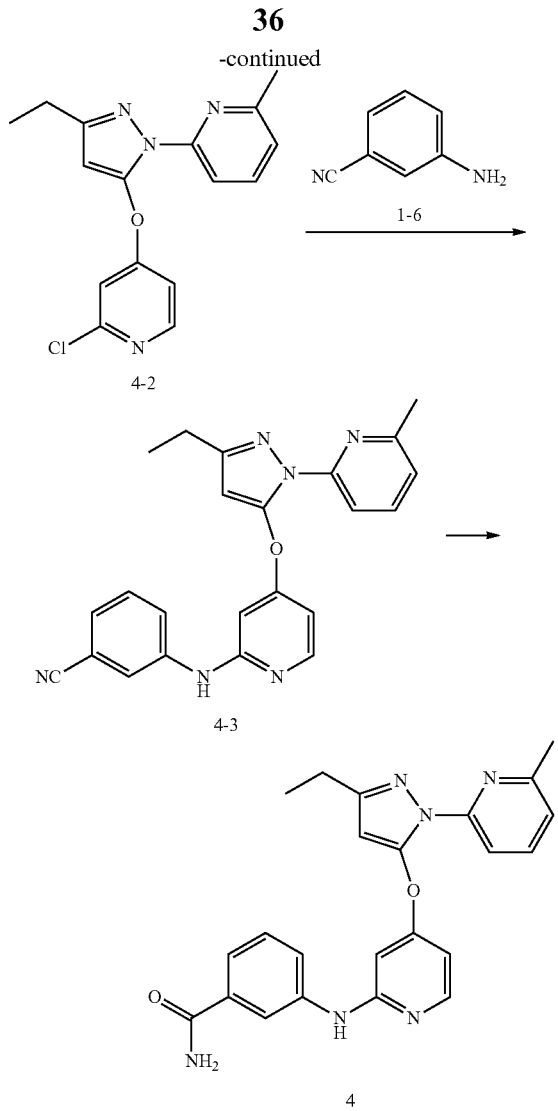

Step A: Compound 2-2 (10 g, 81.20 mmol, 1 eq) and ethyl propionyl acetate (12.29 g, 85.26 mmol, 1.05 eq) were dissolved in acetic acid (100 mL) and reacted at 80° C. for 12 hours. The solvent was removed in vacuum, then the reaction solution was diluted with water (100 mL). The pH value was adjusted to 7 with saturated sodium bicarbonate aqueous solution, and extracted with ethyl acetate (100 mL×2). The organic phases were combined, washed with saturated brine (100 mL), dried over anhydrous sodium sulfate, filtered, concentrated, and purified by column separation to obtain compound 4-1. MS (ESI) m/z: 204.1 [M+H$^+$].

Step B: 4-1 (1 g, 4.92 mmol, 1 eq) and 1-4 (711.91 mg, 5.41 mmol, 1.1 eq) were dissolved in N,N-dimethylformamide (10 mL), and potassium carbonate (2.04 g, 14.76 mmol, 3 eq) was added. The reaction was carried out at 120° C. for 6 hours. The reaction mixture was diluted with water (60 mL), extracted with ethyl acetate (70 mL×2). The organic phases were combined, washed with saturated brine (60 mL), dried over anhydrous sodium sulfate, filtered, concentrated, and purified by column separation to obtain compound 4-2. MS (ESI) m/z: 315.0 [M+H$^+$].

Step C: 4-2 (1.09 g, 3.46 mmol, 1 eq), 1-6 (450.00 mg, 3.81 mmol, 96.31 μL, 1.1 eq), 4,5-bis(diphenylphosphino)-9,9-dimethylxanthene (200.37 mg, 346.29 μmol, 0.1 eq), cesium carbonate (3.38 g, 10.39 mmol, 3 eq) and palladium acetate (77.74 mg, 346.29 μmol, 0.1 eq) were dissolved in dioxane (10 mL) and reacted at 100° C. for 3 hours under nitrogen atmosphere. The reaction mixture was diluted with water (40 mL) and extracted with ethyl acetate (70 mL×2). The organic phases were combined, washed with saturated brine (60 mL), dried over anhydrous sodium sulfate, filtered, and concentrated. The residue was dissolved in ethyl acetate (70 mL), mercapto silica gel (1 g) was added, and stirred at 25° C. for 1 hour, filtered and concentrated to obtain compound 4-3. MS (ESI) m/z: 397.2 [M+H$^+$].

Step D: Sodium hydroxide (181.61 mg, 4.54 mmol, 1 eq) was dissolved in water (2 mL) and methanol (20 mL), compound 4-3 (1.8 g, 4.54 mmol, 1 eq) and dimethyl sulfoxide (532.11 mg, 6.81 mmol, 532.11 μL, 1.5 eq) were added. Hydrogen peroxide (772.09 mg, 6.81 mmol, 654.31 μL, concentration 30%, 1.5 eq) was dissolved in water (0.6 mL), then added dropwise into the previous reaction solution and reacted at 25° C. for 2 hours. The reaction mixture was quenched by sodium sulfite (0.5 g), diluted with water (60 mL) and extracted with dichloromethane (80 mL×2). The organic phases were combined, washed with saturated brine (70 mL), dried over anhydrous sodium sulfate, filtered, concentrated, and purified by preparative high performance liquid chromatography (formic acid condition) to obtain compound 4. MS (ESI) m/z: 415.1 [M+H$^+$].

$^1$H NMR (400 MHz, DMSO-d$_6$) δ=9.15 (s, 1H), 8.08 (d, J=6.0 Hz, 1H), 8.03 (s, 1H), 7.88-7.73 (m, 3H), 7.50 (d, J=8.0 Hz, 1H), 7.39-7.32 (m, 1H), 7.32-7.21 (m, 2H), 7.12 (d, J=7.6 Hz, 1H), 6.51 (dd, J=2.0, 5.6 Hz, 1H), 6.34 (d, J=2.0 Hz, 1H), 6.27 (s, 1H), 2.65 (q, J=7.6 Hz, 2H), 2.24 (s, 3H), 1.26 (t, J=7.6 Hz, 3H).

Embodiment 5: Compound 5

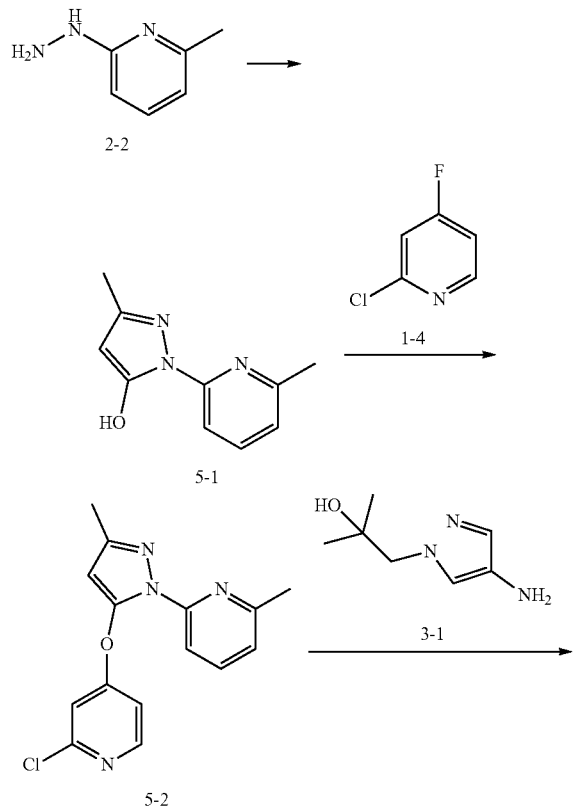

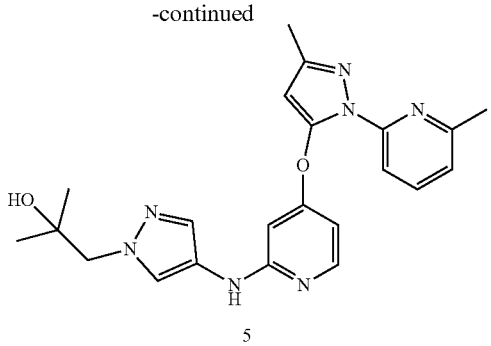

Step A: Ethyl acetoacetate (3.33 g, 25.58 mmol, 3.23 mL, 1.05 eq) was dissolved in glacial acetic acid (30 mL), compound 2-2 (3 g, 24.36 mmol, 1 eq) was added and reacted at 80° C. for 8 hours. The reaction solution was cooled to 25° C. and diluted with water (50 mL). The pH value was adjusted to 6 with sodium hydroxide aqueous solution (4 mol/L), cooled to 0-5° C., and stirred for 15 minutes. After filtration, the filter cake was washed with water (10 mL×3), and dried under reduced pressure to obtain compound 5-1. MS (ESI) m/z: 190.0 [M+H$^+$].

Step B: Compound 5-1 (1 g, 5.29 mmol, 1 eq) and compound 1-4 (834.20 mg, 6.34 mmol, 1.2 eq) were dissolved in N,N-dimethylformamide (20 mL), potassium carbonate (2.19 g, 15.86 mmol, 3 eq) was added, and reacted at 120° C. for 8 hours. The reaction solution was cooled to 25° C., diluted with water (50 mL) and extracted with ethyl acetate (30 mL×3). The organic phases were combined, washed with saturated brine (50 mL), dried over anhydrous sodium sulfate, filtered, concentrated, and purified by column chromatography to obtain compound 5-2. MS (ESI) m/z: 301.1 [M+H$^+$].

Step C: The compound 5-2 (200 mg, 665.02 μmol, 1 eq), compound 3-1 (154.81 mg, 997.53 μmol, 1.5 eq), tris (dibenzylideneacetone) dipalladium (60.90 mg, 66.50 μmol, 0.1 eq), 4,5-bis(diphenylphosphino)-9,9-dimethylxanthene (76.96 mg, 133.00 μmol, 0.2 eq) and cesium carbonate (650.03 mg, 2.00 mM, 3 eq) were added to dioxane (30 mL) successively. The reaction solution was heated to 100° C. and stirred for 12 hours after replacing with nitrogen 3 times. Temperature of the system was cooled to 25° C., mercapto silica gel (1 g) was added and stirred for 15 minutes, filtered, the pH value of filtrate was adjusted to 4 with hydrochloric acid (1 mol/L), diluted with water (20 mL) and washed with ethyl acetate (20 mL×3). The pH value of the aqueous phase was adjusted to 9 with sodium hydroxide aqueous solution (1 mol/L) and extracted with ethyl acetate (20 mL×3). The organic phases were combined and washed with saturated brine (20 mL), dried over anhydrous sodium sulfate, filtered, concentrated, and purified by preparative high performance liquid chromatography (formic acid condition) to obtain compound 5. MS (ESI) m/z: 420.4 [M+H$^+$];

$^1$H NMR (400 MHz, DMSO-d$_6$) δ=8.78 (s, 1H), 8.00 (d, J=5.6 Hz, 1H), 7.89 (s, 1H), 7.78 (t, J=8.0 Hz, 1H), 7.46 (d, J=8.0 Hz, 1H), 7.34 (s, 1H), 7.11 (d, J=7.6 Hz, 1H), 6.35 (dd, J=2.4, 6.4 Hz, 1H), 6.19 (s, 1H), 6.12 (d, J=2.4 Hz, 1H), 3.93 (s, 2H), 2.27 (s, 3H), 2.24 (s, 3H), 1.03 (s, 6H).

Embodiment 6: Compound 6

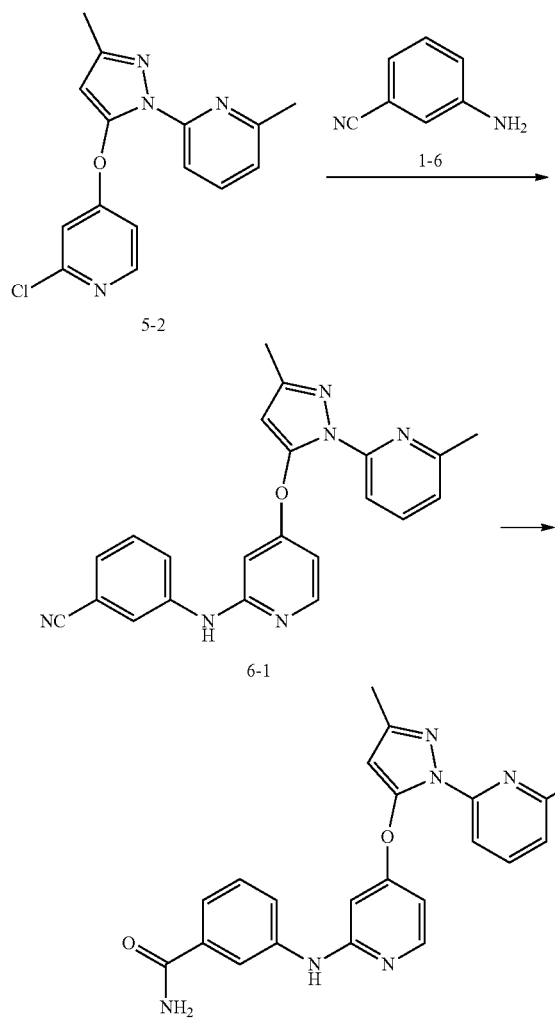

Step A: Compound 5-2 (3.09 g, 10.27 mmol, 1 eq), compound 1-6 (1.82 g, 15.40 mmol, 1.5 eq), tris(dibenzylideneacetone) dipalladium (940.25 mg, 1.03 mmol, 0.1 eq), 4,5-bis(diphenylphosphino)-9,9-dimethylxanthene (1.19 g, 2.05 mmol, 0.2 eq) and cesium carbonate (10.04 g, 30.80 mmol, 3 eq) were added to 1,4-dioxane (90 mL), and reacted at 100° C. for 8 hours under nitrogen atmosphere. The reaction solution was cooled to 25° C., diluted with water (100 mL), filtered, and the pH value of the filtrate was adjusted to 4 with hydrochloric acid (1 mol/L), and washed with ethyl acetate (30 mL×3). Then the pH value of the aqueous phase was adjusted to 9 with sodium hydroxide aqueous solution (1 mol/L), extracted with ethyl acetate (60 mL×3), the organic phases were combined, washed with saturated brine (60 mL), dried over anhydrous sodium sulfate, filtered and concentrated to obtain compound 6-1. MS (ESI) m/z: 383.4 [M+H⁺].

Step B: Sodium hydroxide aqueous solution (1 mol/L, 9.94 mL, 1 eq) was added to ethanol (40 mL), compound 6-1 (3.8 g, 9.94 mmol, 1 eq) and dimethyl sulfoxide (1.55 g, 19.87 mmol, 1.55 mL, 2 eq) were added. Hydrogen peroxide (2.25 g, 19.87 mmol, 1.91 mL, purity: 30%, 2 eq) was dissolved in water (2 mL), and added dropwise slowly to the reaction solution at 25-35° C. After the addition was completed, the reaction was carried out at 25° C. for 8 hours. Saturated sodium sulfite aqueous solution (5 mL) and water (20 mL) were added, the ethanol was removed in vacuum, and then extracted with ethyl acetate (20 mL×3). The organic phases were combined, washed with saturated brine (30 mL), dried over anhydrous sodium sulfate, filtered, concentrated, and purified by preparative high performance liquid chromatography (formic acid condition) to obtain compound 6. MS (ESI) m/z: 401.1 [M+H⁺].

¹H NMR (400 MHz, DMSO-d₆) δ=9.16 (s, 1H), 8.09 (d, J=6.0 Hz, 1H), 8.04 (s, 1H), 7.83-7.77 (m, 3H), 7.50 (d, J=8.0 Hz, 1H), 7.36 (d, J=7.6 Hz, 1H), 7.29 (t, J=8.0 Hz, 2H), 7.12 (d, J=7.6 Hz, 1H), 6.52 (dd, J=2.0, 5.6 Hz, 1H), 6.35 (d, J=2.0 Hz, 1H), 6.24 (s, 1H), 2.30 (s, 3H), 2.25 (s, 3H).

Embodiment 7: Compound 7

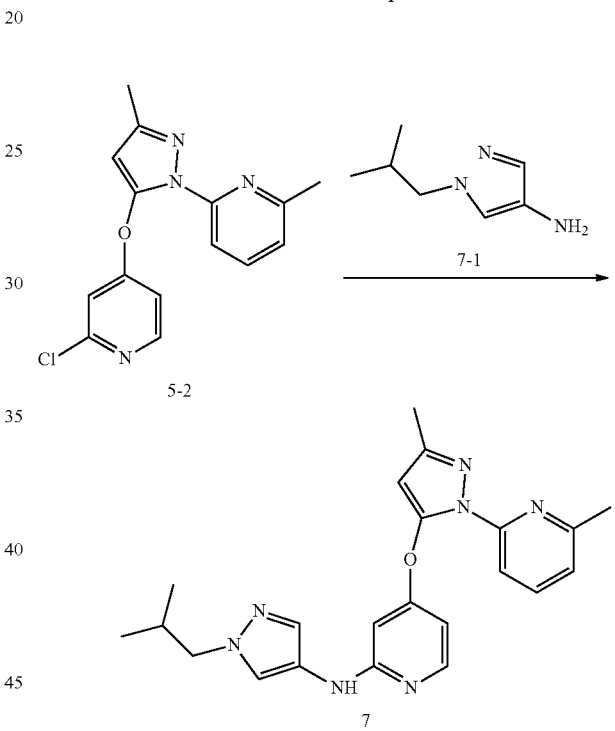

Compound 5-2 (200 mg, 665.02 μmol, 1 eq), compound 7-1 (138.85 mg, 997.53 μmol, 1.5 eq), tris(dibenzylideneacetone) dipalladium (60.90 mg, 66.50 μmol, 0.1 eq), 4,5-bis(diphenylphosphino)-9,9-dimethylxanthene (76.9 mg, 133.00 μmol, 0.2 eq) and cesium carbonate (650.03 mg, 2.00 mmol, 3 eq) were sequentially added to 1,4-dioxane (5 mL), and reacted at 100° C. for 8 hours under nitrogen atmosphere. The reaction solution was cooled to 25° C., mercapto silica gel (0.1 g) was added and stirred for 15 minutes, filtered, the pH value of the filtrate was adjusted to 4 with hydrochloric acid (1 mol/L), diluted with water (20 mL), and washed with ethyl acetate (20 mL×3). The pH value of the aqueous phase was adjusted to 9 with sodium hydroxide aqueous solution (1 mol/L), extracted with ethyl acetate (20 mL×3), the organic phases were combined, washed with saturated brine (20 mL), dried over anhydrous sodium sulfate, filtered, concentrated, and purified by preparative high performance liquid chromatography (formic acid condition) to obtain compound 7. MS (ESI) m/z: 404.2 [M+H⁺].

$^1$H NMR (400 MHz, DMSO-d$_6$) δ=8.76 (s, 1H), 8.00 (d, J=5.6 Hz, 1H), 7.85 (s, 1H), 7.77 (t, J=8.0 Hz, 1H), 7.46 (d, J=8.0 Hz, 1H), 7.33 (s, 1H), 7.11 (d, J=7.6 Hz, 1H), 6.35 (dd, J=2.0, 5.6 Hz, 1H), 6.18 (s, 1H), 6.12 (d, J=2.0 Hz, 1H), 3.82 (d, J=7.2 Hz, 2H), 2.27 (s, 3H), 2.25 (s, 3H), 2.10-2.00 (m, 1H), 0.81 (d, J=6.8 Hz, 6H).

Embodiment 8: Compound 8

Embodiment 9: Compound 9

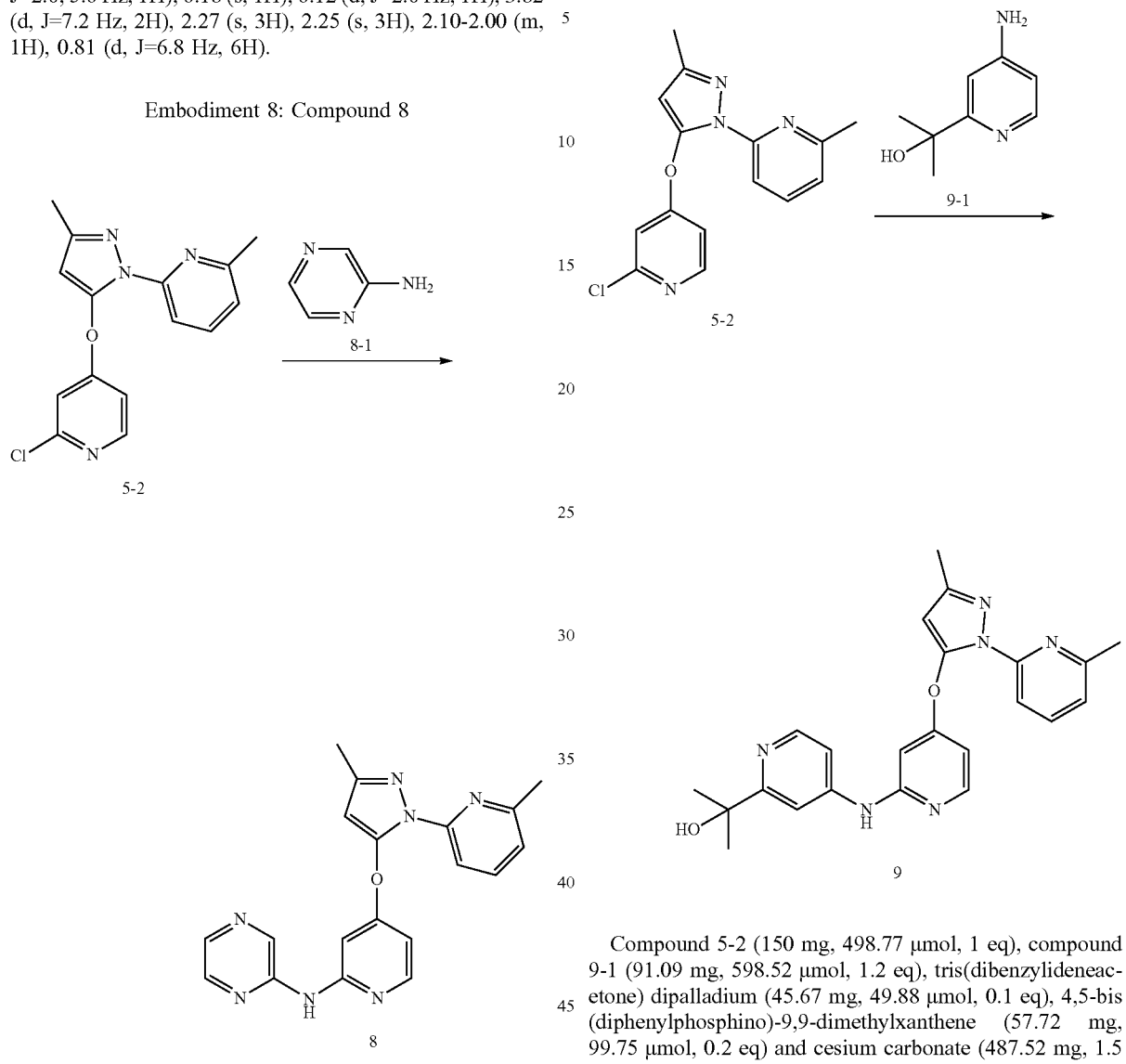

Compound 5-2 (0.15 g, 498.77 μmol, 1 eq), 8-1 (56.92 mg, 598.52 μmol, 1.2 eq), 4,5-bis(diphenylphosphino)-9,9-dimethylxanthene (28.86 mg, 49.88 μmol, 0.1 eq), palladium acetate (11.20 mg, 49.88 μmol, 0.1 eq) and cesium carbonate (487.52 mg, 1.50 mmol, 3 eq) were dissolved in 1,4-dioxane (2 mL), reacted at 100° C. for 16 hours under nitrogen atmosphere. The reaction solution was diluted with water (20 mL) and extracted with ethyl acetate (20 mL×2). The organic phases were combined, washed with saturated brine (60 mL), dried over anhydrous sodium sulfate, filtered, concentrated, and purified by preparative high performance liquid chromatography (formic acid condition) to obtain compound 8. MS (ESI) m/z: 360.1 [M+H$^+$].

$^1$H NMR (400 MHz, DMSO-d$_6$) δ=10.10-9.98 (m, 1H), 9.07-8.94 (m, 1H), 8.24-8.13 (m, 2H), 8.11-8.05 (m, 1H), 7.83-7.73 (m, 1H), 7.56-7.46 (m, 1H), 7.45-7.39 (m, 1H), 7.14-7.05 (m, 1H), 6.64-6.53 (m, 1H), 6.23 (s, 1H), 2.29 (s, 3H), 2.23-2.18 (m, 3H).

Compound 5-2 (150 mg, 498.77 μmol, 1 eq), compound 9-1 (91.09 mg, 598.52 μmol, 1.2 eq), tris(dibenzylideneacetone) dipalladium (45.67 mg, 49.88 μmol, 0.1 eq), 4,5-bis(diphenylphosphino)-9,9-dimethylxanthene (57.72 mg, 99.75 μmol, 0.2 eq) and cesium carbonate (487.52 mg, 1.5 mmol, 3 eq) were added to 1,4-dioxane (3 mL) sequentially, and reacted at 100° C. for 8 hours under nitrogen atmosphere. The reaction solution was cooled to 25° C., mercapto silica gel (0.1 g) was added and stirred for 15 minutes, filtered, the pH value of the filtrate was adjusted to 4 with hydrochloric acid (1 mol/L), diluted with water (20 mL), and washed with ethyl acetate (20 mL×3). The pH value of the aqueous phase was adjusted to 9 with aqueous sodium hydroxide solution (1 mol/L), extracted with ethyl acetate (20 mL×3), the organic phases were combined, washed with saturated brine (20 mL), dried over anhydrous sodium sulfate, filtered, concentrated, and purified by preparative high performance liquid chromatography (formic acid condition) to obtain compound 9. MS (ESI) m/z: 417.1 [M+H$^+$].

$^1$H NMR (400 MHz, DMSO-d$_6$) δ=9.52 (s, 1H), 8.20-8.16 (m, 3H), 7.78 (t, J=8.0 Hz, 1H), 7.71 (d, J=2.0 Hz, 1H), 7.66 (dd, J=2.0, 5.6 Hz, 1H), 7.50 (d, J=8.0 Hz, 1H), 7.10 (d, J=7.6 Hz, 1H), 6.61 (dd, J=2.0, 5.6 Hz, 1H), 6.43 (d, J=2.0 Hz, 1H), 6.25 (s, 1H), 2.29 (s, 3H), 2.20 (s, 3H), 1.40 (s, 6H).

Embodiment 10: Compound 10

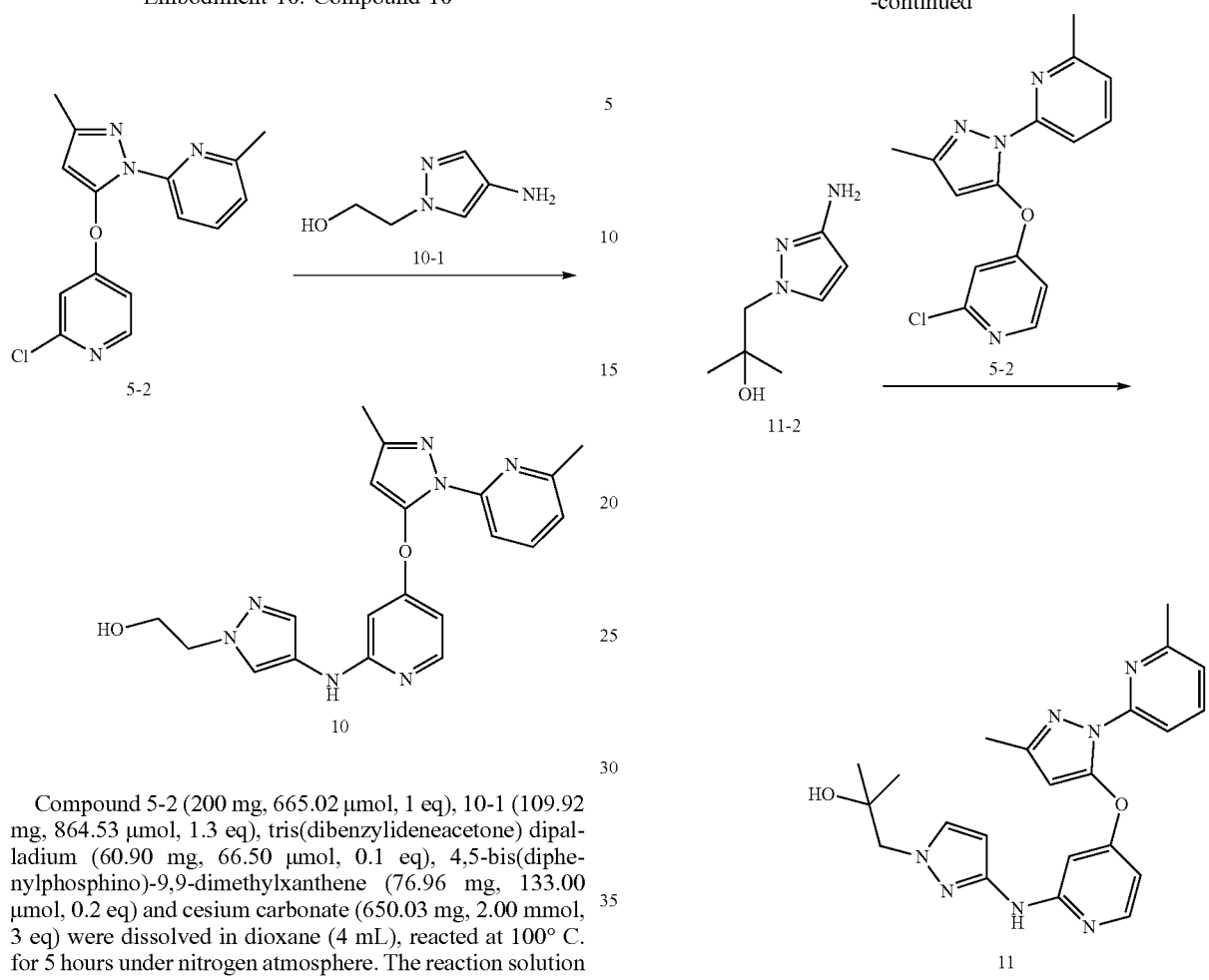

Compound 5-2 (200 mg, 665.02 μmol, 1 eq), 10-1 (109.92 mg, 864.53 μmol, 1.3 eq), tris(dibenzylideneacetone) dipalladium (60.90 mg, 66.50 μmol, 0.1 eq), 4,5-bis(diphenylphosphino)-9,9-dimethylxanthene (76.96 mg, 133.00 μmol, 0.2 eq) and cesium carbonate (650.03 mg, 2.00 mmol, 3 eq) were dissolved in dioxane (4 mL), reacted at 100° C. for 5 hours under nitrogen atmosphere. The reaction solution was cooled down, diluted with water (40 mL) and extracted with dichloromethane (70 mL×2). The organic phases were combined, washed with saturated brine (60 mL), dried over anhydrous sodium sulfate, filtered, concentrated, and purified by preparative high performance liquid chromatography (trifluoroacetate condition) to obtain compound 10. MS (ESI) m/z: 392.1 [M+H$^+$].

$^1$H NMR (400 MHz, DMSO-d$_6$) δ=9.92 (br s, 1H), 7.98 (d, J=6.8 Hz, 1H), 7.92 (s, 1H), 7.82 (t, J=7.6 Hz, 1H), 7.54 (d, J=8.0 Hz, 1H), 7.49 (s, 1H), 7.15 (d, J=7.6 Hz, 1H), 6.71 (dd, J=2.4, 6.8 Hz, 1H), 6.43 (d, J=2.4 Hz, 1H), 6.35 (s, 1H), 4.13 (t, J=5.6 Hz, 2H), 3.74 (t, J=5.6 Hz, 2H), 2.29 (s, 3H), 2.22 (s, 3H).

Embodiment 11: Compound 11

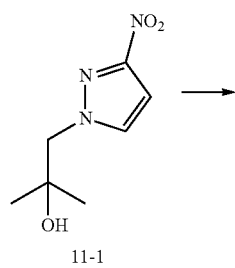

11-1

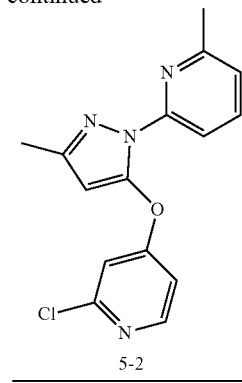

11-2

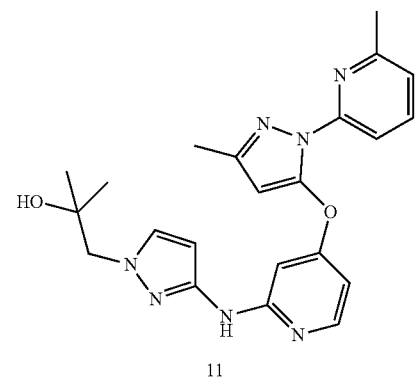

11

Step A: Compound 11-1 (1.1 g, 5.94 mmol, 1 eq) was dissolved in methanol (20 mL), wet palladium on carbon (400 mg, 10%) was added, replaced with hydrogen, and reacted at 25° C. for 2 hours under hydrogen atmosphere. The reaction solution was filtered and concentrated to obtain compound 11-2.

Step B: Compound 5-2 (300 mg, 997.53 μmol, 1 eq), 11-2 (170.30 mg, 1.10 mmol, 1.1 eq), 4,5-bis(diphenylphosphino)-9,9-dimethylxanthene (115.44 mg, 199.51 μmol, 0.2 eq), cesium carbonate (975.04 mg, 2.99 mmol, 3 eq) and tris(dibenzylideneacetone) dipalladium (91.35 mg, 99.75 μmol, 0.1 eq) were dissolved in 1,4-dioxane (10 mL) and reacted at 100° C. for 5 hours under nitrogen atmosphere. The reaction solution was diluted with water (50 mL) and extracted with ethyl acetate (50 mL×3). The organic phases were combined, washed with saturated brine (50 mL×3), dried over anhydrous sodium sulfate, filtered, concentrated, and purified by preparative high performance liquid chromatography (alkaline condition) to obtain compound 11. MS (ESI) m/z: 420.2 [M+H$^+$].

$^1$H NMR (400 MHz, DMSO-d$_6$) δ=9.22 (s, 1H), 8.00 (d, J=5.6 Hz, 1H), 7.77 (t, J=8.0 Hz, 1H), 7.47 (d, J=2.4 Hz, 2H), 7.11 (d, J=7.6 Hz, 1H), 7.06 (d, J=2.0 Hz, 1H), 6.41-6.37 (m, 1H), 6.18-6.13 (m, 2H), 4.65-4.60 (m, 1H), 3.84 (s, 2H), 3.32 (s, 2H), 2.28 (s, 3H), 2.24 (s, 3H), 1.03 (s, 6H).

Embodiment 12: Compound 12

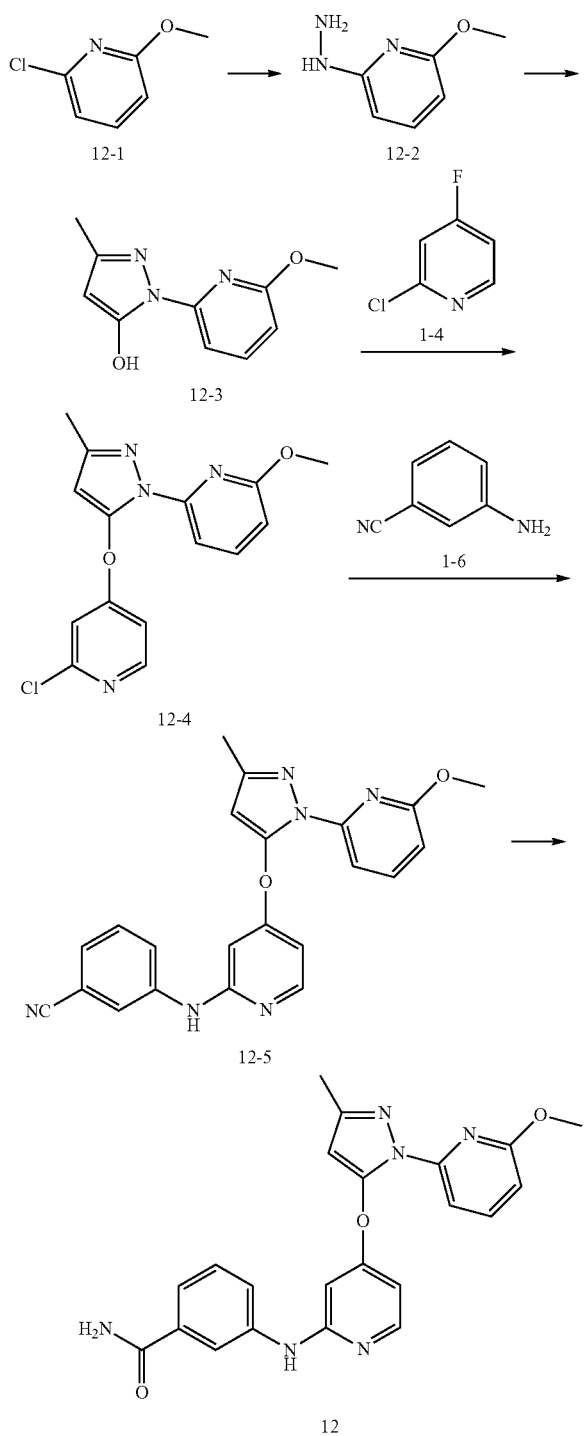

Step A: A solution of compound 12-1 (10 g, 69.65 mmol, 8.26 mL, 1 eq) in hydrazine hydrate (35.58 g, 696.52 mmol, 34.54 mL, 10 eq) was reacted at 120° C. for 12 hours and concentrated to obtain compound 12-2.

Step B: The compound ethyl acetoacetate (17.96 g, 137.98 mmol, 17.43 mL, 1.2 eq) was added to a solution of compound 12-2 (16 g, 114.98 mmol, 1 eq) in acetic acid (160 mL), and reacted at 80° C. for 12 hours. The reaction solution was cooled, the pH value was adjusted to 9 with saturated sodium carbonate solution, and extracted with ethyl acetate (100 mL×3). The organic phases were combined, washed with saturated sodium chloride, dried over anhydrous sodium sulfate, filtered, and concentrated to obtain compound 12-3. MS (ESI) m/z: 206.1 [M+H$^+$].

Step C: 1-4 (769.16 mg, 5.85 mmol, 1.2 eq) and potassium carbonate (2.02 g, 14.62 mmol, 3 eq) were added to a solution of compound 12-3 (1 g, 4.87 mmol, 1 eq) in N,N-dimethylformamide (15 mL), and reacted at 80° C. for 12 hours. The reaction solution was diluted with ethyl acetate (50 mL), washed with saturated brine (50 mL×3), dried over anhydrous sodium sulfate, filtered, concentrated, and purified by preparative high performance liquid chromatography (formic acid system) to obtain compound 12-4. MS (ESI) m/z: 317.0 [M+H$^+$].

Step D: Cesium carbonate (308.60 mg, 947.14 μmol, 3 eq), 4,5-bis(diphenylphosphino)-9,9-dimethylxanthene (18.27 mg, 31.57 μmol, 0.1 eq) and tris(dibenzylideneacetone) dipalladium (28.91 mg, 31.57 μmol, 0.1 eq) were added to a solution of compound 12-4 (100 mg, 315.71 μmol, 1 eq) and 1-6 (55.95 mg, 473.57 μmol, 1.5 eq) in 1,4-dioxane (10 mL), and reacted at 100° C. for 12 hours under nitrogen atmosphere. Ethyl acetate (30 mL) was added, filtered, and the filtrate was washed with saturated sodium chloride solution (30 mL×3). The organic phase was added to hydrochloric acid (20 mL, 1 mol/L), the aqueous phase obtained by separation was washed with ethyl acetate (20 mL), and then pH value was adjusted to 9 with saturated sodium carbonate solution, extracted with ethyl acetate (20 mL×2). The organic phases were combined, washed with saturated brine (30 mL×3), dried over anhydrous sodium sulfate, filtered, and concentrated to obtain compound 12-5. MS (ESI) m/z: 399.1 [M+H$^+$].

Step E: Dimethyl sulfoxide (23.53 mg, 301.19 μmol, 23.53 μL, 2 eq), sodium hydroxide (12.05 mg, 301.19 μmol, 2 eq) and hydrogen peroxide (34.15 mg, 301.19 μmol, 28.94 μL, purity 30%, 2 eq) were added to a solution of compound 12-5 (60 mg, 150.60 μmol, 1 eq) in ethanol (2 mL) and water (1 mL), and reacted at 25° C. for 12 hours. The reaction solution was diluted with ethyl acetate (20 mL), washed with saturated sodium sulfite solution, dried over anhydrous sodium sulfate, filtered, concentrated, and purified by preparative high performance liquid chromatography (formic acid system) to obtain compound 12. MS (ESI) m/z: 417.2 [M+H$^+$].

$^1$H NMR (400 MHz, DMSO-d$_6$) δ=9.19 (br s, 1H), 8.10-8.00 (m, 2H), 7.87-7.72 (m, 3H), 7.40-7.15 (m, 4H), 6.69 (br s, 1H), 6.56 (br s, 1H), 6.39 (br s, 1H), 6.21 (br s, 1H), 3.48 (s, 3H), 2.28 (s, 3H).

Embodiment 13: Compound 13

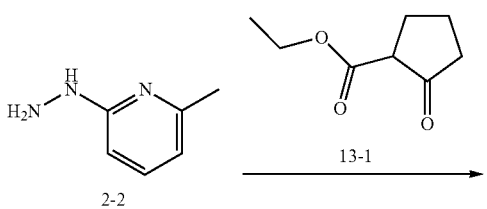

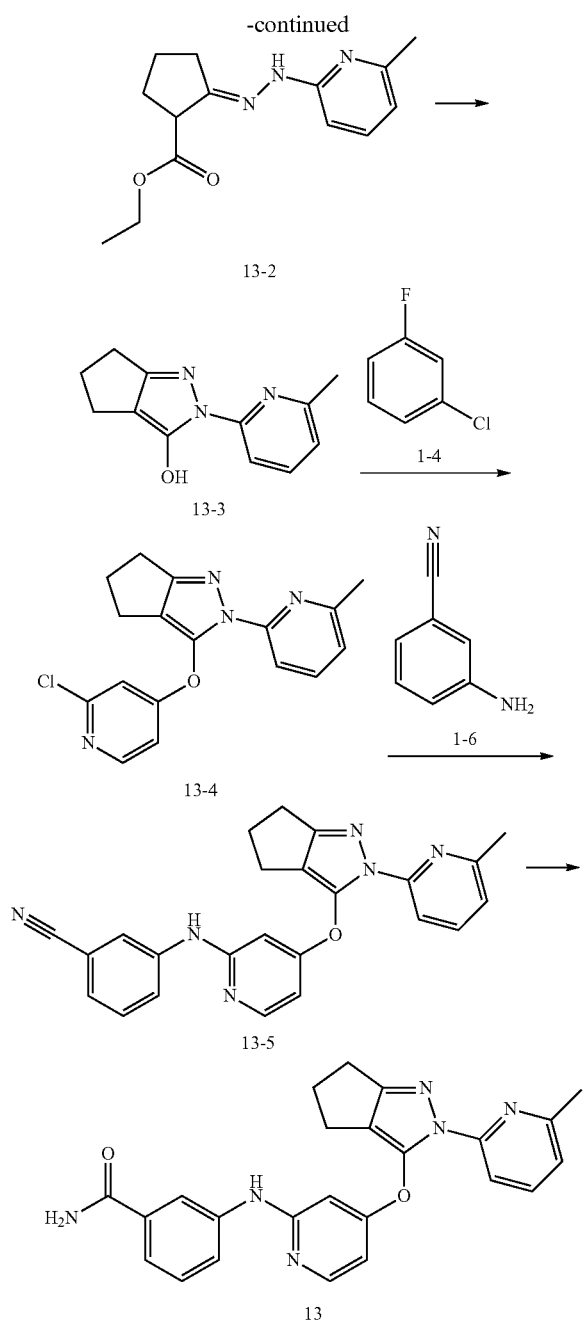

dimethylformamide (20 mL), potassium carbonate (3.35 g, 24.25 mmol, 3 eq) was added under nitrogen atmosphere, and reacted at 120° C. for 16 hours under nitrogen atmosphere. The reaction solution was diluted with water (20 mL) and extracted with ethyl acetate (20 mL×2). The organic phases were combined, washed with saturated brine (60 mL), dried over anhydrous sodium sulfate, filtered, concentrated, and purified by column chromatography to obtain compound 13-4. MS (ESI) m/z: 327.1 [M+H$^+$].

Step D: Compound 13-4 (1.1 g, 3.37 μmol, 1 eq), 1-6 (437.43 mg, 3.70 mmol, 1.1 eq), palladium acetate (75.57 mg, 336.62 μmol, 0.1 eq), 4,5-bis(diphenylphosphino)-9,9-dimethylxanthene (194.77 mg, 336.62 μmol, 0.1 eq) and cesium carbonate (3.29 g, 10.10 mmol, 3 eq) were dissolved in dioxane (15 mL) and reacted at 100° C. for 3 hours under nitrogen atmosphere. The reaction solution was diluted with water (10 mL) and extracted with ethyl acetate (10 mL×2). The organic phases were combined, washed with saturated brine (30 mL), dried over anhydrous sodium sulfate, filtered, and concentrated to obtain compound 13-5. MS (ESI) m/z: 409.1 [M+H$^+$].

Step E: Compound 13-5 (1.2 g, 2.94 mmol, 1 eq), dimethyl sulfoxide (459.10 mg, 5.88 mmol, 459.10 μL, 2 eq) and sodium hydroxide (58.75 mg, 1.47 μmol, 0.5 eq) were dissolved in ethanol (15 mL), and hydrogen peroxide (499.66 mg, 4.41 mmol, 423.44 μL, 30% purity, 1.5 eq) was added dropwise under nitrogen atmosphere, and reacted at 25° C. for 2 hours. The reaction solution was diluted with water (30 mL) and extracted with ethyl acetate (30 mL×2). The organic phases were combined, washed with saturated brine (60 mL), dried over anhydrous sodium sulfate, filtered, concentrated, and purified by preparative high performance liquid chromatography (formic acid condition) to obtain compound 13. MS (ESI) m/z: 427.3 [M+H+].

$^1$H NMR (400 MHz, DMSO-d$_6$) δ=9.19-9.11 (m, 1H), 8.11-8.06 (m, 1H), 8.03-8.00 (m, 1H), 7.86-7.73 (m, 3H), 7.47-7.41 (m, 1H), 7.38-7.22 (m, 3H), 7.11-7.06 (m, 1H), 6.53-6.48 (m, 1H), 6.37-6.30 (m, 1H), 2.73 (s, 2H), 2.60-2.57 (m, 2H), 2.42-2.37 (m, 2H), 2.25-2.22 (m, 3H).

Embodiment 14: Compound 14

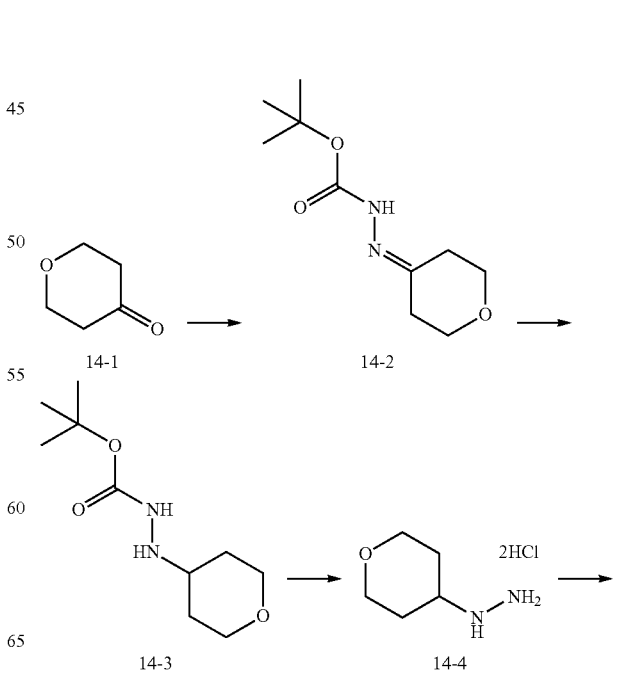

Step A: Compound 2-2 (2 g, 16.24 mmol, 1 eq) and compound 13-1 (2.54 g, 16.24 mmol, 2.42 mL, 1 eq) were dissolved in ethanol (20 mL) and reacted at 25° C. for 0.5 hours. The reaction solution was concentrated to obtain compound 13-2. MS (ESI) m/z: 262.1 [M+H$^+$].

Step B: Compound 13-2 (4 g, 15.31 mmol, 1 eq) and sodium methoxide (1.65 g, 30.61 mmol, 2 eq) were dissolved in methanol (40 mL) and reacted at 80° C. for 1 hour. The reaction solution was diluted with water (30 mL) and extracted with ethyl acetate (30 mL×2). The organic phases were combined, washed with saturated brine (10 mL×2), dried over anhydrous sodium sulfate, filtered, and concentrated to obtain compound 13-3. MS (ESI) m/z: 216.1 [M+H$^+$].

Step C: Compound 13-3 (1.74 g, 8.08 mmol, 1 eq) and 1-4 (1.59 g, 12.13 mmol, 1.5 eq) were dissolved in N,N-

-continued

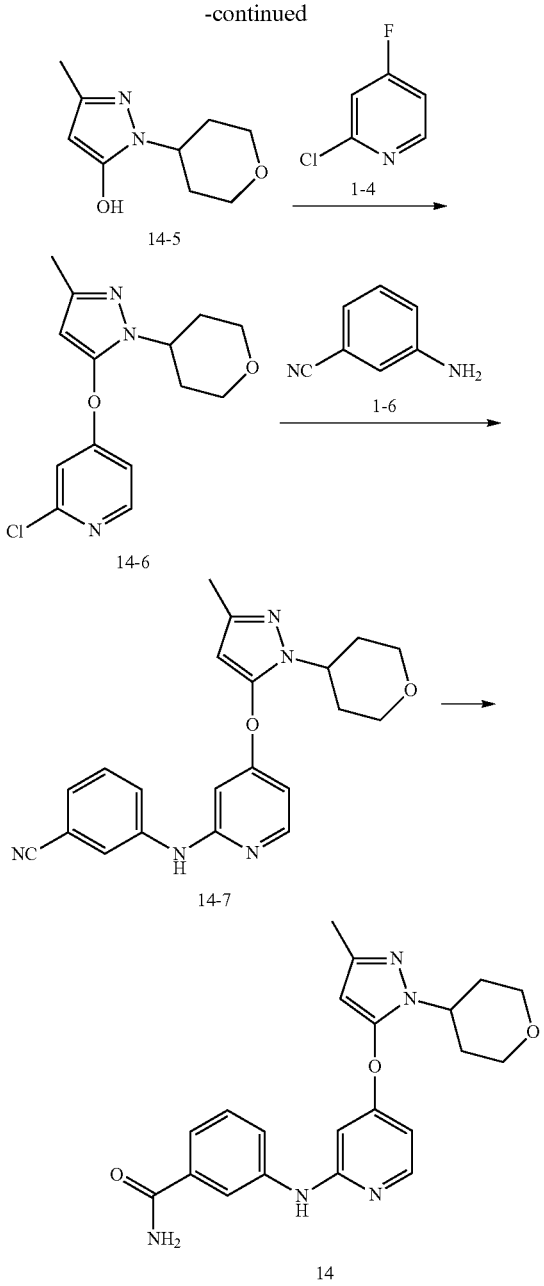

Step A: Compound 14-1 (10 g, 99.88 mmol, 1 eq) was dissolved in methanol (150 mL), tert-butyl carbazate (13.20 g, 99.88 mmol, 1 eq) was added, and reacted at 25° C. for 10 hours. The reaction solution was concentrated to obtain compound 14-2.

Step B: Compound 14-2 (8 g, 37.34 mmol, 1 eq) was dissolved in a mixed solvent of acetic acid (50 mL) and water (50 mL), stirred for 1 hour at 25° C., and sodium cyanoborohydride (2.58 g, 41.07 mmol, 1.1 eq) was added in batches, and reacted at 20° C. for 2 hours. The pH value was adjusted to 7 with sodium hydroxide aqueous solution (1 mol/L), extracted with dichloromethane (100 mL×3), washed with saturated sodium bicarbonate aqueous solution (100 mL×2), dried over anhydrous sodium sulfate, filtered, and concentrated to obtain compound 14-3.

Step C: Compound 14-3 (7.2 g, 33.29 mmol, 1 eq) was dissolved in methanol (10 mL), hydrochloric acid methanol (4 mol/L, 40 mL) was added, and reacted at 20° C. for 4 hours. The reaction solution was concentrated to obtain compound 14-4.

Step D: Compound 14-4 (4.1 g, 35.30 mmol, 1 eq, dihydrochloride) and ethyl acetoacetate (9.19 g, 70.59 mmol, 2 eq) were dissolved in acetic acid (40 mL), and reacted at 90° C. for 10 hours under nitrogen atmosphere. The reaction solution was cooled down, concentrated, and purified by preparative high performance liquid chromatography (trifluoroacetic acid condition) to obtain compound 14-5. MS (ESI) m/z: 183.1 [M+H$^+$].

Step E: Compound 14-5 (1.1 g, 6.04 mmol, 1 eq) and compound 1-4 (873.44 mg, 6.64 mmol, 1.1 eq) were dissolved in N,N-dimethylformamide (20 mL), potassium carbonate (2.5 g, 18.11 mmol, 3 eq) was added, and reacted at 90° C. for 12 hours. The reaction solution was diluted with water (50 mL) and extracted with ethyl acetate (100 mL×3). The organic phases were combined, washed with saturated brine (100 mL×3), dried over anhydrous sodium sulfate, filtered, concentrated, and purified by column separation to obtain compound 14-6. MS (ESI) m/z: 294.1 [M+H$^+$].

Step F: Compound 14-6 (300 mg, 1.02 mmol, 1 eq), 1-6 (144.78 mg, 1.23 mmol, 1.2 eq), 4,5-bis(diphenylphosphino)-9,9-dimethylxanthene (118.19 mg, 204.26 μmol, 0.2 eq), cesium carbonate (998.26 mg, 3.06 mmol, 3 eq) and tris(dibenzylideneacetone) dipalladium (187.04 mg, 204.26 μmol, 0.2 eq) were dissolved in dioxane (10 mL), and reacted at 100° C. for 12 hours under nitrogen atmosphere. The reaction solution was diluted with water (20 mL), and extracted with ethyl acetate (20 mL×3). The organic phases were combined, washed with saturated brine (20 mL×3), dried over anhydrous sodium sulfate, filtered, concentrated, and purified by column separation to obtain compound 14-7. MS (ESI) m/z: 376.1 [M+H$^+$].

Step G: Compound 14-7 (270 mg, 718.19 μmol, 1 eq), sodium hydroxide (719.19 μL, 2 mol/L, 2 eq) and dimethyl sulfoxide (112.39 mg, 1.44 mmol, 2 eq) were dissolved in ethanol (5 mL). At room temperature, hydrogen peroxide (163.09 mg, 1.44 mmol, 138.21 μL, purity 30%, 2 eq) was slowly added to the reaction solution, and reacted at 25° C. for 2 hours. The reaction solution was diluted with water (10 mL) and extracted with ethyl acetate (10 mL×3). The organic phases were combined, washed with saturated brine (10 mL×3), dried over anhydrous sodium sulfate, filtered, concentrated, and purified by preparative high performance liquid chromatography (formic acid condition) to obtain compound 14. MS (ESI) m/z: 394.2 [M+H$^+$].

$^1$H NMR (400 MHz, DMSO-d$_6$) δ=9.26 (s, 1H), 8.13 (d, J=6.0 Hz, 1H), 8.04 (t, J=2.0 Hz, 1H), 7.89-7.79 (m, 2H), 7.39-7.35 (m, 1H), 7.33-7.24 (m, 2H), 6.57 (dd, J=2.4, 6.0 Hz, 1H), 6.42 (d, J=2.4 Hz, 1H), 5.84 (s, 1H), 4.20 (tt, J=4.0, 11.6 Hz, 1H), 3.90 (br dd, J=4.0, 11.6 Hz, 2H), 3.35 (br s, 2H), 2.17 (s, 3H), 1.99 (dq, J=4.4, 12.3 Hz, 2H), 1.76-1.67 (m, 2H).

Embodiment 15: Compound 15

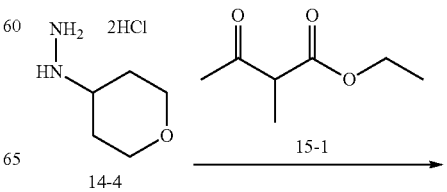

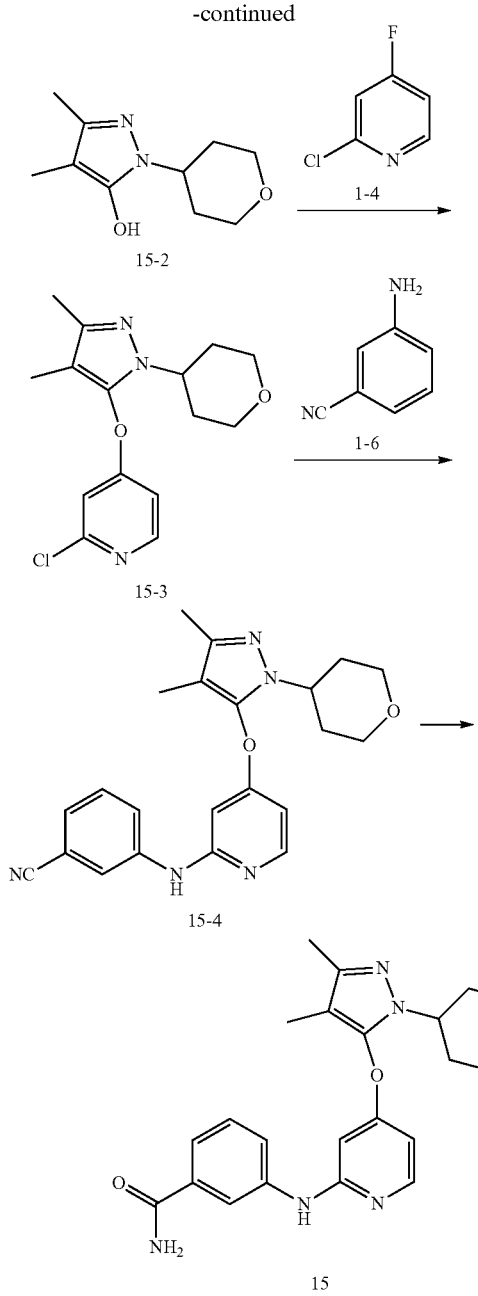

acetate (30 mL×3). The organic phases were combined, washed with saturated brine (30 mL), dried over anhydrous sodium sulfate, filtered, concentrated, and purified by column separation to obtain compound 15-3. MS (ESI) m/z: 308.1 [M+H⁺].

Step C: Compound 15-3 (200 mg, 649.83 μmol, 1 eq) and compound 1-6 (92.12 mg, 779.79 μmol, 1.2 eq), tris(dibenzylideneacetone) dipalladium (59.51 mg, 64.98 μmol, 0.1 eq), 4,5-bis(diphenylphosphino)-9,9-dimethylxanthene (75.20 mg, 129.97 μmol, 0.2 eq) and cesium carbonate (635.18 mg, 1.95 mmol, 3 eq) were added to dioxane (3 mL) and reacted at 100° C. for 12 hours under nitrogen atmosphere. The reaction was cooled down, mercapto silica gel (0.1 g) was added, stirred for 15 minutes, and filtered. The pH value of the filtrate was adjusted to 4 with hydrochloric acid (1 mol/L), diluted with water (20 mL), and washed with ethyl acetate (20 mL×3). The pH value of the aqueous phase was adjusted to 9 with sodium hydroxide aqueous solution (1 mol/L), and extracted with ethyl acetate (20 mL×3). The organic phases were combined, washed with saturated brine (20 mL), dried over anhydrous sodium sulfate, filtered and concentrated to obtain compound 15-4. MS (ESI) m/z: 390.3 [M+H⁺].

Step D: Compound 15-4 (252 mg, 647.07 μmol, 1 eq) was dissolved in ethanol (5 mL), sodium hydroxide aqueous solution (1 mol/L, 647.07 μL, 1 eq), dimethyl sulfoxide (101.12 mg, 1.29 mmol, 101.12 μL, 2 eq) and hydrogen peroxide (146.73 mg, 1.29 mmol, 124.35 μL, purity 30%, 2 eq) were added and reacted at 25° C. for 4 hours. Saturated sodium sulfite aqueous solution (1 mL) and water (20 mL) were added, ethanol was removed under reduced pressure, and extracted with ethyl acetate (20 mL×3). The organic phases were combined, washed with saturated brine (30 mL), dried over anhydrous sodium sulfate, filtered, concentrated, and purified by preparative high performance liquid chromatography (formic acid condition) to obtain compound 15. MS (ESI) m/z: 408.4 [M+H⁺].

$^1$H NMR (400 MHz, DMSO-$d_6$) δ=9.25 (s, 1H), 8.12 (d, J=6.0 Hz, 1H), 8.04 (s, 1H), 7.85 (d, J=5.6 Hz, 2H), 7.38-7.36 (m, 1H), 7.32-7.27 (m, 2H), 6.51 (dd, J=2.4, 6.0 Hz, 1H), 6.26 (d, J=2.4 Hz, 1H), 4.16-4.08 (m, 1H), 3.88 (dd, J=3.2, 11.2 Hz, 2H), 3.35 (t, J=11.2 Hz, 2H), 2.12 (s, 3H), 2.02-1.92 (m, 2H), 1.72-1.67 (m, 5H).

Embodiment 16: Compound 16

Step A: Compound 14-4 (1 g, 5.29 mmol, 1.0 eq) was dissolved in glacial acetic acid (10 mL), compound 15-1 (991.84 mg, 6.88 mmol, 972.39 μL, 1.30 eq) was added, and reacted at 80° C. for 8 hours. The reaction solution was cooled down, diluted with water (20 mL), the pH value was adjusted to 7 with sodium hydroxide aqueous solution (4 mol/L), extracted with dichloromethane/isopropanol mixed solvent (volume ratio 3:1, 30 mL×3), dried over anhydrous sodium sulfate, filtered, and concentrated to obtain compound 15-2. MS (ESI) m/z: 197.1 [M+H⁺].

Step B: Compound 15-2 (0.8 g, 4.08 mmol, 1 eq) and compound 1-4 (589.83 mg, 4.48 mmol, 1.1 eq) were dissolved in N,N-dimethylformamide (10 mL) and potassium carbonate (1.69 g, 12.23 mmol, 3 eq) was added, and reacted at 90° C. for 8 hours. The reaction solution was cooled down, diluted with water (30 mL), and extracted with ethyl

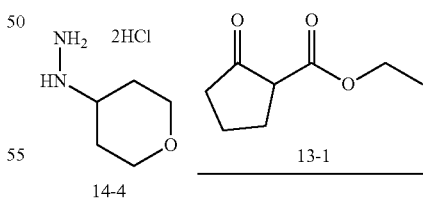

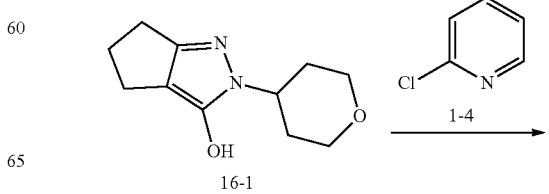

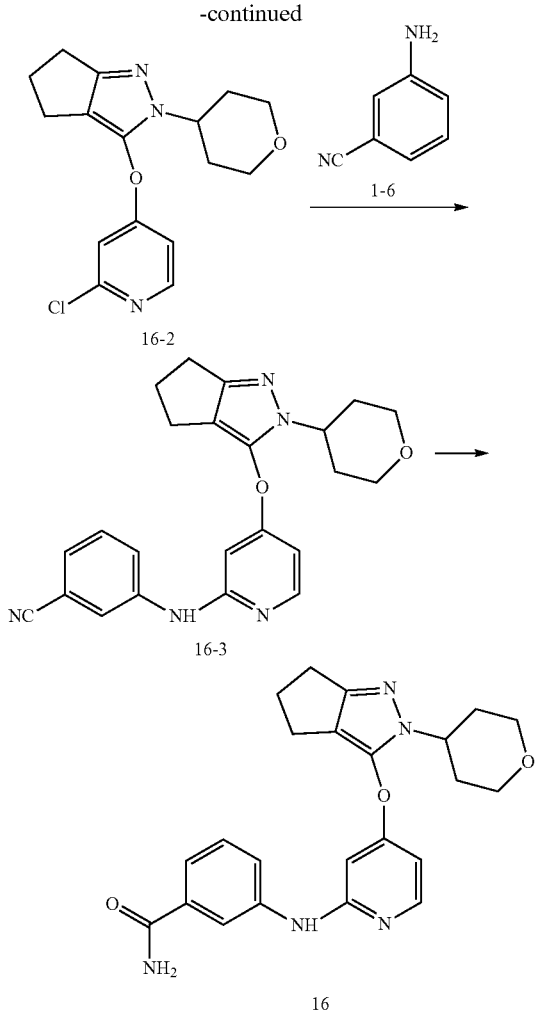

Step A: Compound 13-1 (1.02 g, 6.53 mmol, 971.43 μL, 1.23 eq) was dissolved in methanol (10 mL), compound 14-4 (1 g, 5.29 mmol, 1.0 eq) was added, and reacted at 25° C. for 2 hours. Sodium methoxide (1.06 g, 19.62 mmol, 3.7 eq) was added and reacted at 70° C. for 1 hour. The reaction solution was cooled down, diluted with water (20 mL), the pH value was adjusted to 7 with sodium hydroxide aqueous solution (4 mol/L), methanol was removed under reduced pressure, extracted with dichloromethane/isopropanol mixed solvent (volume ratio 3:1, 30 mL×3), dried over anhydrous sodium sulfate, filtered, and concentrated to obtain compound 16-1. MS (ESI) m/z: 209.6 [M+H⁺].

Step B: Compound 16-1 (1.13 g, 5.43 mmol, 1 eq) and compound 1-4 (785.08 mg, 5.97 mmol, 1.1 eq) were dissolved in N,N-dimethylformamide (10 mL) and potassium carbonate (2.25 g, 16.28 mmol, 3 eq) was added, and reacted at 90° C. for 8 hours. The reaction solution was cooled down, diluted with water (30 mL), and extracted with ethyl acetate (30 mL×3). The organic phases were combined, washed with saturated brine (30 mL), dried over anhydrous sodium sulfate, filtered, and purified by column separation to obtain compound 16-2. MS (ESI) m/z: 320.0 [M+H⁺].

Step C: Compound 16-2 (200 mg, 625.42 μmol, 1 eq) and compound 1-6 (88.66 mg, 750.50 μmol, 1.2 eq), tris(dibenzylideneacetone) dipalladium (57.27 mg, 62.54 μmol, 0.1 eq), 4,5-bis(diphenylphosphino)-9,9-dimethylxanthene (72.38 mg, 125.08 μmol, 0.2 eq) and cesium carbonate (611.32 mg, 1.88 mmol, 3 eq) were added to 1,4-dioxane (3 mL) and reacted at 100° C. for 12 hours under nitrogen atmosphere. The reaction solution was cooled down, mercapto silica gel (0.1 g) was added and stirred for 15 minutes, and filtered. The pH value of the filtrate was adjusted to 4 with hydrochloric acid (1 mol/L), diluted with water (20 mL), and washed with ethyl acetate (20 mL×3). The pH value of the aqueous phase was adjusted to 9 with sodium hydroxide aqueous solution (1 mol/L), and extracted with ethyl acetate (20 mL×3). The organic phases were combined, washed with saturated brine (20 mL), dried over anhydrous sodium sulfate, filtered and concentrated to obtain compound 16-3. MS (ESI) m/z: 402.3 [M+H⁺].

Step D: Compound 16-3 (177 mg, 440.89 μmol, 1 eq) was dissolved in ethanol (5 mL), sodium hydroxide aqueous solution (1 mol/L, 440.89 μL, 1 eq), dimethyl sulfoxide (68.90 mg, 881.78 μmol, 68.90 μL, 2 eq) and hydrogen peroxide (99.98 mg, 881.78 μmol, 84.73 μL, purity 30%, 2 eq) were added and reacted at 25° C. for 4 hours. Saturated aqueous sodium sulfite (1 mL) and water (20 mL) were added, ethanol was removed under reduced pressure, and extracted with ethyl acetate (20 mL×3). The organic phases were combined, washed with saturated brine (30 mL), dried over anhydrous sodium sulfate, filtered, concentrated, and purified by preparative high performance liquid chromatography (formic acid condition) to obtain compound 16. MS (ESI) m/z: 420.1 [M+H⁺].

¹H NMR (400 MHz, DMSO-d₆) δ=9.25 (s, 1H), 8.13 (d, J=5.6 Hz, 1H), 8.03 (s, 1H), 7.87-7.85 (m, 2H), 7.38-7.37 (m, 1H), 7.33-7.23 (m, 2H), 6.56 (dd, J=2.0, 6.0 Hz, 1H), 6.39 (d, J=2.0 Hz, 1H), 4.24-4.16 (m, 1H), 3.92-3.88 (m, 2H), 2.62 (t, J=7.2 Hz, 2H), 2.43-2.39 (m, 2H), 2.35-2.30 (m, 2H), 2.04-1.94 (m, 2H), 1.75-1.71 (m, 2H).

Embodiment 17: Compound 17

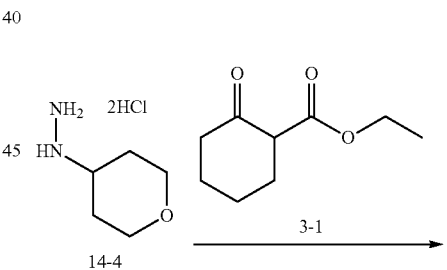

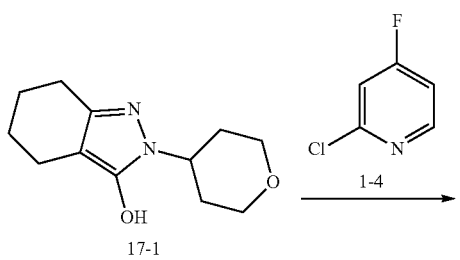

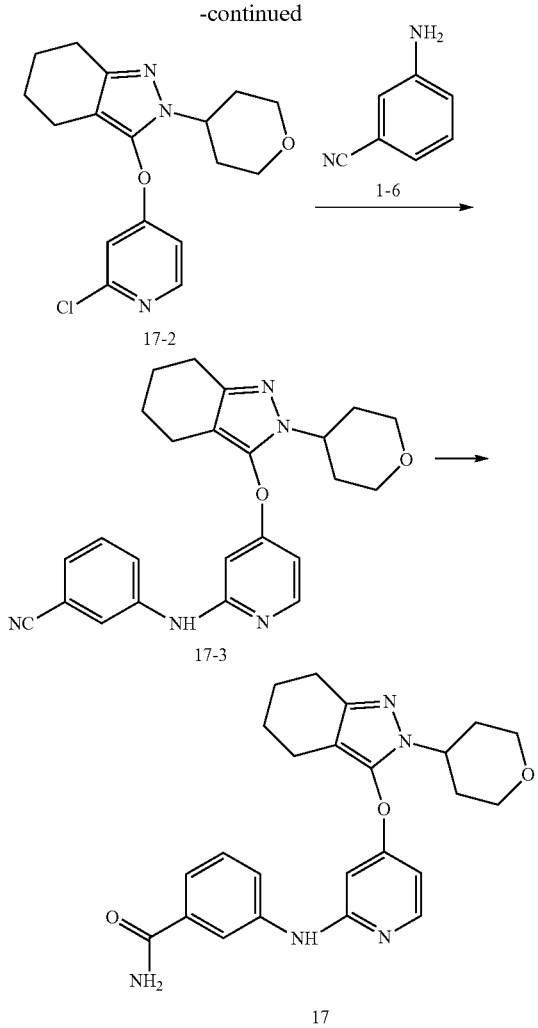

Step A: Compound 14-4 (520 mg, 2.75 mmol, 1.0 eq) was dissolved in methanol (6 mL), compound 3-1 (761.93 mg, 4.48 mmol, 718.80 μL, 1.63 eq) was added, and reacted at 25° C. for 2 hours. Sodium methoxide (724.74 mg, 13.42 mmol, 4.88 eq) was added and reacted at 70° C. for 1 hour. Cooled down, methanol was removed in vacuum, and the reaction mixture was diluted with water (20 mL). The pH value was adjusted to 6 with hydrochloric acid (1 mol/L), extracted with dichloromethane/isopropanol mixed solvent (volume ratio 3:1, 20 mL×3). The organic phases were combined, washed with saturated brine (20 mL), dried over anhydrous sodium sulfate, filtered, and concentrated to obtain compound 17-1. MS (ESI) m/z: 223.2 [M+H$^+$].

Step B: Compound 17-1 (400 mg, 1.80 mmol, 1 eq) was dissolved in N,N-dimethylformamide (5 mL), and compound 1-4 (260.37 mg, 1.98 mmol, 1.1 eq) and potassium carbonate (746.11 mg, 5.40 mmol, 3 eq) were added, and reacted at 100° C. for 8 hours. The reaction solution was cooled down, the reaction mixture was diluted with water (30 mL), and extracted with ethyl acetate (20 mL×3). The organic phases were combined, washed with saturated brine (20 mL), dried over anhydrous sodium sulfate, filtered, and purified by column separation to obtain compound 17-2. MS (ESI) m/z: 334.1 [M+H$^+$].

Step C: Compound 17-2 (273 mg, 817.83 μmol, 1 eq) and compound 1-6 (107.16 mg, 899.61 μmol, 1.1 eq), tris (dibenzylideneacetone) dipalladium (74.89 mg, 81.78 μmol, 0.1 eq), 4,5-bis(diphenylphosphino)-9,9-dimethylxanthene (94.64 mg, 163.57 μmol, 0.2 eq) and cesium carbonate (799.39 mg, 2.45 mmol, 3 eq) were added to 1,4-dioxane (10 mL) successively and reacted at 100° C. for 12 hours under nitrogen atmosphere. The reaction was cooled down, mercapto silica gel (0.1 g) was added and stirred for 15 minutes, and filtered. The pH value of the filtrate was adjusted to 4 with hydrochloric acid (1 mol/L), diluted with water (20 mL), and washed with ethyl acetate (20 mL×3). The pH value of the aqueous phase was adjusted to 9 with sodium hydroxide aqueous solution (1 mol/L), and extracted with ethyl acetate (20 mL×3). The organic phases were combined, washed with saturated brine (20 mL), dried over anhydrous sodium sulfate, filtered and concentrated to obtain compound 17-3. MS (ESI) m/z: 416.1 [M+H$^+$].

Step D: Sodium hydroxide aqueous solution (1 mol/L, 324.92 μL, 1 eq) was added to ethanol (5 mL), and then compound 17-3 (135 mg, 324.92 μmol, 1 eq), dimethyl sulfoxide (50.77 mg, 649.84 μmol, 50.77 μL, 2 eq) and hydrogen peroxide (73.68 mg, 649.84 μmol, 62.44 μL, purity 30%, 2 eq) were added and reacted at 25° C. for 2 hours. Saturated sodium sulfite aqueous solution (1 mL) and water (20 mL) were added to the reaction solution, ethanol was removed in vacuum, and extracted with ethyl acetate (20 mL×3). The organic phases were combined, washed with saturated brine (20 mL), dried over anhydrous sodium sulfate, filtered, concentrated, and purified by preparative high performance liquid chromatography (formic acid condition) to obtain compound 17. MS (ESI) m/z: 434.3 [M+H$^+$].

$^1$H NMR (400 MHz, DMSO-d$_6$) δ=9.26 (s, 1H), 8.12 (d, J=5.6 Hz, 1H), 8.03 (s, 1H), 7.86-7.84 (m, 2H), 7.38-7.36 (m, 1H), 7.30 (t, J=8.0 Hz, 1H), 7.27 (s, 1H), 6.53 (dd, J=2.0, 6.0 Hz, 1H), 6.30 (d, J=2.0 Hz, 1H), 4.21-4.13 (m, 1H), 3.89 (dd, J=3.6, 11.2 Hz, 2H), 3.34 (s, 2H), 2.55 (t, J=6.0 Hz, 2H), 2.17 (t, J=6.0 Hz, 2H), 2.03-1.92 (m, 2H), 1.74-1.63 (m, 6H).

Embodiment 18: Trifluoroacetate of Compound 18

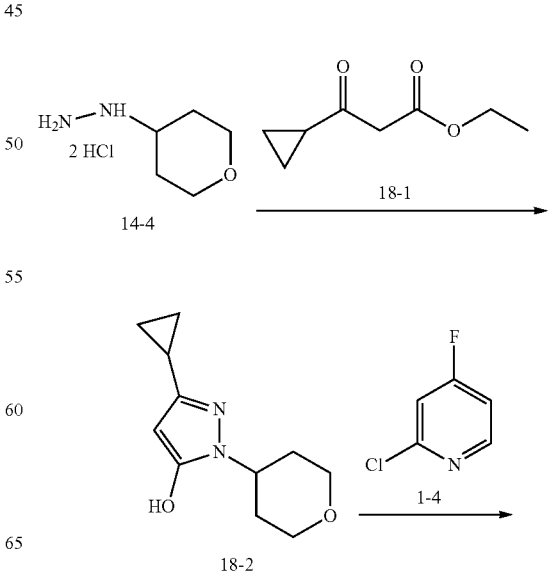

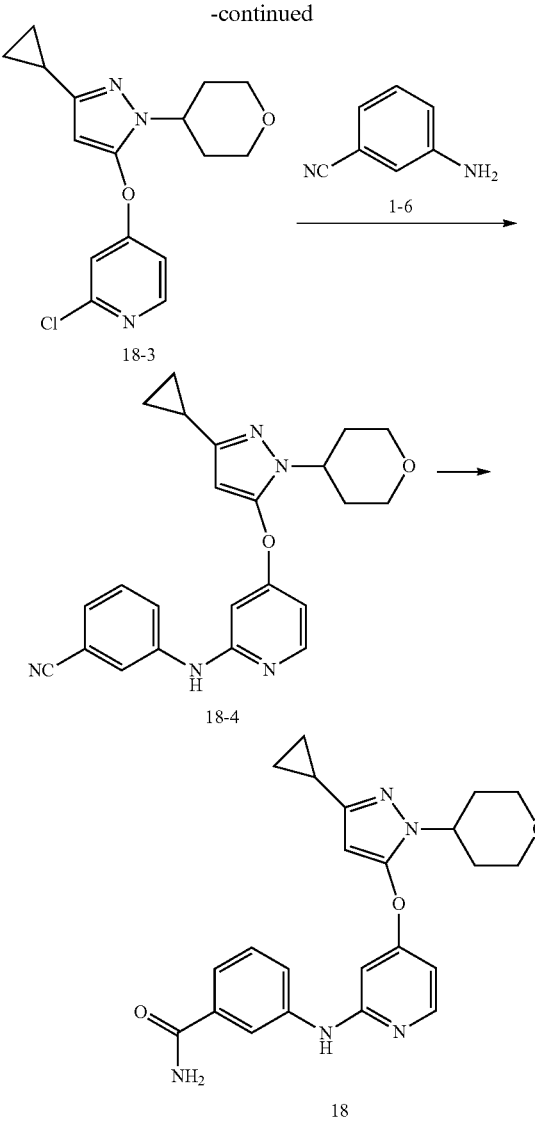

Step A: 14-4 (3 g, 15.87 mmol, 1 eq) and 18-1 (2.60 g, 16.66 mmol, 89.55 μL, 1.05 eq) were dissolved in acetic acid (20 mL), and reacted at 80° C. for 12 hours under nitrogen atmosphere. Cooled down, the reaction solution was concentrated, diluted with water (100 mL), and the pH value was adjusted to 7 with saturated sodium bicarbonate aqueous solution. Dichloromethane (100 mL×2) was added for extraction. The organic phases were combined, washed with water (100 mL), dried over anhydrous sodium sulfate, filtered, concentrated, and purified by column separation to obtain compound 18-2. MS (ESI) m/z: 209.0 [M+H$^+$].

Step B: Compound 18-2 (1 g, 4.8 mmol, 1 eq) and 1-4 (694.76 mg, 5.28 mmol, 1.1 eq) were dissolved in N,N-dimethylformamide (10 mL), and potassium carbonate (2.65 g, 19.21 mmol, 4 eq) was added, reacted at 100° C. for 4 hours. The reaction solution was diluted with water (100 mL), and extracted with ethyl acetate (90 mL×2). The organic phases were combined, washed with saturated brine (90 mL), dried over anhydrous sodium sulfate, filtered, concentrated, and purified by column separation to obtain compound 18-3. MS (ESI) m/z: 320.1 [M+H+].

Step C: Compound 18-3 (300 mg, 938.13 μmol, 1 eq) and 1-6 (121.91 mg, 1.03 μmol, 1.1 eq), 4,5-bis(diphenylphosphino)-9,9-dimethylxanthene (54.28 mg, 93.81 mol, 0.1 eq), cesium carbonate (916.98 mg, 2.81 mmol, 3 eq) and palladium acetate (21.06 mg, 93.81 μmol, 0.1 eq) were dissolved in dioxane (4 mL) and reacted at 100° C. for 3 hours under nitrogen atmosphere. The reaction solution was diluted with water (40 mL), and extracted with ethyl acetate (70 mL×2). The organic phases were combined, washed with saturated brine (60 mL), dried over anhydrous sodium sulfate, filtered and concentrated to obtain compound 18-4. MS (ESI) m/z: 402.3 [M+H$^+$].

Step D: Sodium hydroxide (39.85 mg, 996.36 μmol, 1 eq) was dissolved in water (0.5 mL), methanol (5 mL) was added, then compound 18-4 (400 mg, 996.36 μmol, 1 eq) and dimethyl sulfoxide (116.77 mg, 1.49 mmol, 116.77 μL, 1.5 eq) were added. Hydrogen peroxide (169.43 mg, 1.49 mmol, 143.59 μL, 30% purity, 1.5 eq) was dissolved in water (0.15 mL), then added dropwise to the above reaction solution, and reacted at 25° C. for 2 hours. The reaction solution was diluted with water (80 mL) and extracted with dichloromethane (80 mL×2). The organic phases were combined, washed with water (80 mL), dried over anhydrous sodium sulfate, filtered, concentrated, and purified by preparative high performance liquid chromatography (trifluoroacetic acid condition) to obtain trifluoroacetate of compound 18. MS (ESI) m/z: 420.2 [M+H$^+$].

$^1$H NMR (400 MHz, DMSO-d$_6$) δ=9.85 (br s, 1H), 8.70 (br s, 1H), 8.12 (d, J=6.4 Hz, 1H), 8.05-7.86 (m, 2H), 7.73 (dd, J=1.6, 8.0 Hz, 1H), 7.56 (d, J=7.6 Hz, 1H), 7.46-7.29 (m, 2H), 6.71 (dd, J=2.4, 6.4 Hz, 1H), 6.50 (d, J=2.4 Hz, 1H), 5.79 (s, 1H), 4.21 (tt, J=4, 11.6 Hz, 1H), 3.91 (br dd, J=3.6, 11.2 Hz, 2H), 3.46-3.33 (m, 2H), 2.00 (dq, J=4.4, 12.4 Hz, 2H), 1.87 (tt, J=5.2, 8.4 Hz, 1H), 1.72 (br dd, J=2.4, 12.4 Hz, 2H), 0.93-0.82 (m, 2H), 0.70-0.61 (m, 2H).

Embodiment 19: Compound 19

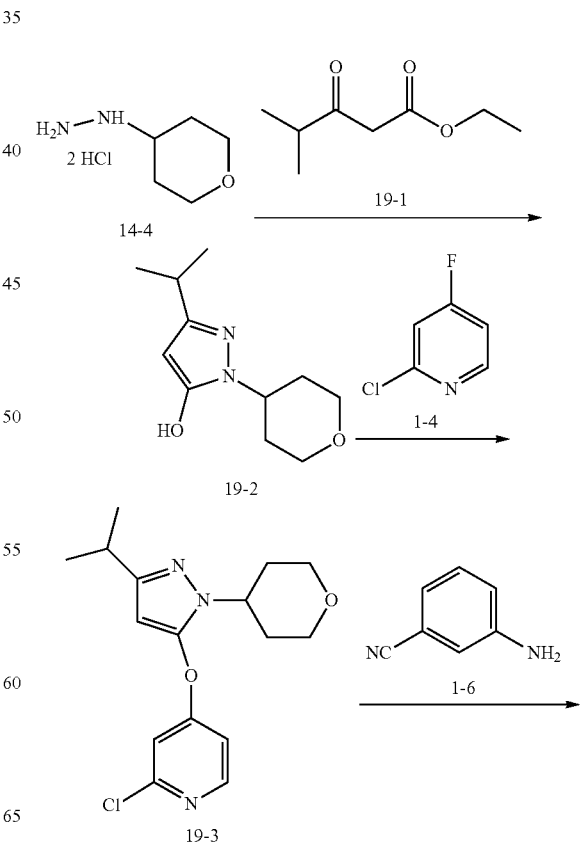

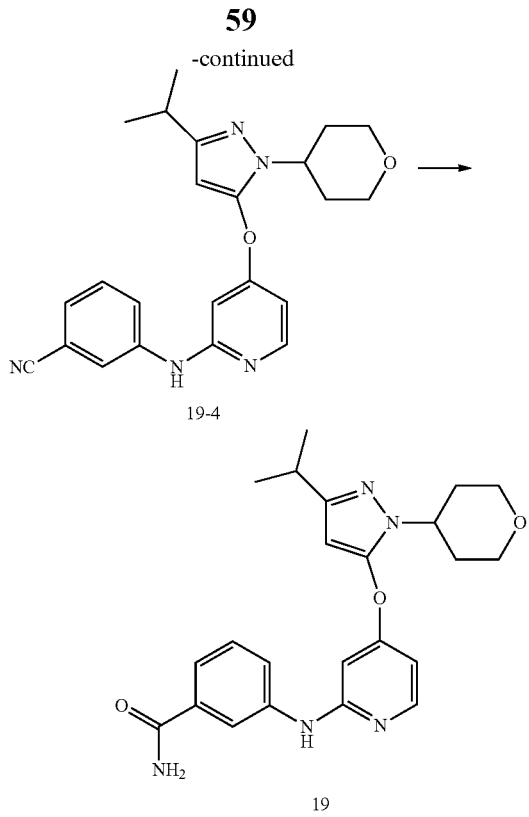

Step A: 14-4 (3 g, 15.87 mmol, 1 eq, dihydrochloride) and 19-1 (2.64 g, 16.66 mmol, 2.69 mL, 1.05 eq) were dissolved in acetic acid (20 mL), and reacted at 80° C. for 12 hours under nitrogen atmosphere. Cooled down, the reaction solution was concentrated, diluted with water (100 mL), and the pH value of the solution was adjusted to 7 with saturated sodium bicarbonate aqueous solution. Dichloromethane (100 mL×2) was added for extraction. The organic phases were combined, washed with water (100 mL), dried over anhydrous sodium sulfate, filtered, concentrated, and purified by column separation to obtain compound 19-2. MS (ESI) m/z: 211.0 [M+H$^+$].

Step D: Compound 19-2 (0.872 g, 4.15 mmol, 1 eq) and 1-4 (600.03 mg, 4.56 mmol, 1.1 eq) were dissolved in N,N-dimethylformamide (10 mL). Potassium carbonate (2.29 g, 16.59 mmol, 4 eq) was added, and reacted at 100° C. for 2 hours. The reaction solution was diluted with water (100 mL) and extracted with ethyl acetate (100 mL×2). The organic phases were combined, washed with saturated brine (100 mL), dried over anhydrous sodium sulfate, filtered, concentrated, and purified by column separation to obtain compound 19-3. MS (ESI) m/z: 322.1 [M+H$^+$].

Step E: Compound 19-3 (300 mg, 932.25 μmol, 1 eq), 1-6 (121.15 mg, 1.03 mmol, 96.31 μL, 1.1 eq), 4,5-bis(diphenylphosphino)-9,9-dimethylxanthene (53.94 mg, 93.23 μmol, 0.1 eq), cesium carbonate (911.24 mg, 2.80 mmol, 3 eq) and palladium acetate (20.93 mg, 93.23 μmol, 0.1 eq) were dissolved in dioxane (4 mL) and reacted at 100° C. for 3 hours under nitrogen atmosphere. The reaction solution was diluted with water (40 mL) and extracted with ethyl acetate (70 mL×2). The organic phases were combined, washed with saturated brine (60 mL), dried over anhydrous sodium sulfate, filtered, and concentrated to obtain compound 19-4. MS (ESI) m/z: 404.3 [M+H$^+$].

Step F: Sodium hydroxide (39.66 mg, 991.38 μmol, 1 eq) was dissolved in water (0.5 mL), methanol (5 mL) was added, then compound 19-4 (0.4 g, 991.38 μmol, 1 eq) and dimethyl sulfoxide (116.19 mg, 1.49 mmol, 116.19 μL, 1.5 eq) were added. Hydrogen peroxide (168.58 mg, 1.49 mmol, 142.87 μL, purity 30%, 1.5 eq) was dissolved in water (0.15 mL), then added dropwise to the above reaction solution, and reacted at 25° C. for 2 hours. The reaction solution was diluted with water (80 mL) and extracted with dichloromethane (80 mL×2). The organic phases were combined, washed with water (80 mL), dried over anhydrous sodium sulfate, filtered, concentrated, and purified by preparative high performance liquid chromatography (trifluoroacetic acid condition) to obtain compound 19. MS (ESI) m/z: 422.2 [M+H$^+$].

$^1$H NMR (400 MHz, DMSO-d$_6$) δ=9.78 (br s, 1H), 8.17-8.08 (m, 1H), 7.97 (t, J=2.0 Hz, 1H), 7.92 (br s, 1H), 7.77-7.69 (m, 1H), 7.54 (br d, J=8 Hz, 1H), 7.42-7.33 (m, 2H), 6.68 (dd, J=2.4, 6.4 Hz, 1H), 6.48 (d, J=2.4 Hz, 1H), 5.92 (s, 1H), 4.23 (tt, J=4.4, 11.6 Hz, 1H), 3.91 (br dd, J=4.0, 11.2 Hz, 2H), 3.46-3.31 (m, 2H), 2.84 (J=7.2 Hz, 1H), 2.09-1.91 (m, 2H), 1.78-1.66 (m, 2H), 1.20 (s, 3H), 1.18 (s, 3H).

Activity Test

Experimental Embodiment 1: Inhibitory Activity Assay on Smad Phosphorylation

Experimental Materials:
Both HEK-Blue-TGFβ cells and Quanti-Blue reagent were purchased from Invivogen Company. TGFβ was purchased from PeproTech.

Experimental Method:
The compounds to be tested were diluted 5 times with a row gun to the 8th concentration, that is, diluted from 1 mmol/L to 12.8 nmol/L, the final concentration of dimethyl sulfoxide was 100%, and a double hole experiment was set up. 2 μL of inhibitors of each concentration gradient, 18 μL of TGFβ (20 ng/mL), and 180 μL of cell suspension (140,000 cells/mL) were added to the microplate. At this time, the final concentration gradient of the compound was 10 mol/L diluted to 0.13 nmol/L. The cell plate was placed at 37° C. in a 5% CO$_2$ incubator for 24 hours. After the reaction was completed, 40 μL of cell culture supernatant was taken out from each well to a new transparent microtiter plate, 160 μL of Quanti-Blue reagent was added to each well, and then the reaction was carried out at 37° C. for 60 minutes. After the reaction was completed, the PerkinElmer Envision multilabel analyzer was used to read the absorption light at 630 nm.

Data Analysis:
The original data was converted into the inhibition rate, and the IC$_{50}$ value can be obtained by curve fitting with four parameters. The inhibitory activity of the compounds of the present disclosure on Smad phosphorylation is shown in Table 1.

Experimental Results: See Table 1:

TABLE 1

| Compound | pSmad inhibition IC$_{50}$ (nmol/L) |
|---|---|
| Compound 1 | 65.45 |
| Compound 2 | 246.8 |
| Compound 3 | 54.27 |
| Compound 4 | 53.83 |
| Compound 5 | 440.8 |
| Compound 6 | 79.15 |
| Compound 7 | 354.1 |
| Compound 8 | 683.9 |
| Compound 9 | 267.7 |

TABLE 1-continued

| Compound | pSmad inhibition IC$_{50}$ (nmol/L) |
|---|---|
| Compound 10 | 354.7 |
| Compound 11 | 191 |
| Compound 12 | 432.3 |
| Compound 13 | 59.58 |
| Compound 14 | 335.5 |
| Compound 15 | 415.9 |
| Compound 16 | 165.7 |
| Compound 17 | 620.9 |
| Trifluoroacetate of compound 18 | 282.9 |
| Compound 19 | 587 |

Conclusion: The compounds of the present disclosure have excellent inhibitory activity on pSmad, which proves that the compounds of the present disclosure can inhibit the TGF-β/SMAD signal pathway.

Experimental Embodiment 2: Pharmacokinetics Study of Cassette Drug Administration in Vivo Experimental Purpose:

The purpose of this experiment is to evaluate the pharmacokinetic behavior of the compound after a single intravenous injection and intragastric administration, and to investigate the bioavailability after intragastric administration.

Experimental Operation:

CD-1 male mice aged from 7 to 10 weeks were selected, and the doses for intravenous and oral administration were 1 mg/kg and 1.5 mg/kg, respectively. The mice were fasted for at least 12 hours before the administration, and resumed feeding 4 hours after the administration. The mice were free to drink during the entire experiment.

On the day of the experiment, animals in the intravenous group were given a single injection of the corresponding compound through the tail vein with a volume of 5 mL/kg; the oral group was given the corresponding compound by a single gavage with a volume of 5 mL/kg. The animals were weighed before administration, and the administration volume was calculated according to the body weight. Sample collection time: 0.083 hours, 0.25 hours, 0.5 hours, 1 hour, 2 hours, 4 hours, 8 hours, 24 hours in the injection group; 0.25 hours, 0.5 hours, 1 hour, 2 hours, 4 hours, 6 hours, 8 hours, 24 hours in the gavage group. Approximately 30 μL of whole blood was collected through the saphenous vein at each time point to prepare plasma for high-performance liquid chromatography-tandem mass spectrometry (LC-MS/MS) for concentration determination. All animals were euthanized by $CO_2$ anesthesia after collecting PK samples at the last time point. The non-compartmental model of WinNonlin™ Version 6.3 (Pharsight, Mountain View, CA) pharmacokinetic software was used to process the plasma concentration, and the pharmacokinetic parameters were calculated using the linear and logarithmic trapezoidal method.

Experiment Results: Evaluation results of PK properties are shown in Table 2.

Experimental Conclusion:

Compared with compound A reported in the literature, the compounds of the present disclosure have longer half-life, wider tissue distribution, and significantly improved bioavailability, which show significantly better pharmacokinetic properties than compound A.

TABLE 2

Evaluation results of the pharmacokinetics properties of cassette drug administration in vivo

| | Drug administration | | | | | | | | |
|---|---|---|---|---|---|---|---|---|---|
| | injection (1 mg/kg) | | | | Oral (1.5 mg/kg) | | | | |
| Parameter | $T_{1/2}$ (h) | $Vd_{ss}$ (L/kg) | Cl (mL/min/kg) | $AUC_{0-last}$ (nM·h) | $C_{max}$ (nM) | $T_{max}$ (h) | $T_{1/2}$ (h) | $AUC_{0-last}$ (nM·h) | F (%) |
| Compound A | 0.477 | 0.679 | 37.3 | 1151 | 712 | 0.25 | 1.45 | 586 | 34.9 |
| Compound 6 | 1.32 | 1.05 | 24.9 | 1807 | 804 | 0.25 | 2.84 | 1452 | 54.6 |
| Compound 14 | 1.37 | 2.39 | 37 | 1064 | 567 | 0.25 | 1.61 | 1156 | 75.9 |

$T_{1/2}$: half-life;
$Vd_{ss}$: volume of distribution;
Cl: clearance rate;
$AUC_{0-last}$: area under the curve;
$C_{max}$: maximum concentration;
$T_{max}$: time to peak concentration;
F: bioavailability.

Experimental Embodiment 3: Anti-Tumor Drug Efficacy Study of Mouse Colon Cancer CT-26 Cell BALB/c Mouse Subcutaneous Allograft Tumor Model In Vivo Experimental Purpose:

The main purpose of this study is to study the anti-tumor drug efficacy of the tested compounds on the CT26 mouse allograft tumor model.

Experimental Operation:

Cell culture: mouse colon cancer CT-26 cells were cultured in monolayer in vitro, and the culture conditions were RPMI-1640 medium with 10% fetal bovine serum, 37° C.

and 5% carbon dioxide incubator. Trypsin-ethylenediaminetetraacetic acid (EDTA) was used for routine digestion and passage twice a week. When the cell saturation was 80%-90% and the number reached the requirement, the cells were collected, counted, and inoculated.

Animals: BALB/c mice, female, 6-8 weeks old.

Tumor inoculation: 0.1 mL of DPBS cell suspension containing 3×10$^5$ CT26 cells was subcutaneously inoculated into the right groin of each mouse, and administration was started on the day of inoculation.

Experimental index: The experimental index was to investigate whether the tumor growth was inhibited, delayed or cured. The tumor diameter was measured with a vernier caliper twice a week. The calculation formula for tumor volume is: V=0.5 L×W$^2$, where L and W refer to the long diameter and short diameter of the tumor, respectively.

Experimental Results: The tumor inhibitory effects of the compounds are shown in Table 3.

Experimental Conclusion: The compounds of the present disclosure have significant anti-tumor efficacy in vivo in a mouse colon cancer CT-26 cell BALB/c mouse subcutaneous allograft tumor model, which show a significantly better tumor suppressive effect than compound A with the same dose (50 mg/kg, twice a day).

2 hours, 4 hours, 8 hours, 24 hours in the injection group, 0.25 hours, 0.5 hours, 1 hour, 2 hours, 4 hours, 6 hours, 8 hours, 24 hours in the gavage group. Approximately 30 μL of whole blood was collected through the saphenous vein at each time point to prepare plasma for high-performance liquid chromatography-tandem mass spectrometry (LC-MS/MS) for concentration determination. All animals were euthanized by $CO_2$ anesthesia after collecting PK samples at the last time point. The non-compartmental model of WinNonlin™ Version 6.3 (Pharsight, Mountain View, CA) pharmacokinetic software was used to process the plasma concentration, and the pharmacokinetic parameters were calculated using the linear and logarithmic trapezoidal method.

Experiment results: Evaluation results of PK properties are shown in Table 4.

Experimental Conclusion:

Compared with compound A reported in the literature, the compounds of the present disclosure have longer half-life, and significantly improved bioavailability, which show significantly better pharmacokinetic properties than compound A.

TABLE 3

Experimental results of CT26 heterotopic transplantation

| Compound | Dose (mg/kg) | Administration frequency | Administration way | Mean tumor volume (mm$^3$) Day 29 | % Inhibitory rate on Day 29 | Drug concentration in tumor tissue (nmol/kg) 1 hour after administration | Drug concentration in tumor tissue (nmol/kg) 12 hours after administration | Plasma AUC (nmol/L · h) |
|---|---|---|---|---|---|---|---|---|
| Solvent | 0 | Twice a day | oral | 2261.3 (Euthanasia) | — | — | — | — |
| Compound A | 50 | Twice a day | oral | 758.19 | 66% | 988 | 180 | 6172 |
| Compound 6 | 50 | Twice a way | oral | 601.7 | 73% | — | — | — |
| Compound 14 | 50 | Twice a day | oral | 424.78 | 81% | 11318 | 820 | 30113 |

Experiment 4: Pharmacokinetic Studies In Vivo

Experimental Purpose:

The purpose of this experiment is to evaluate the pharmacokinetic behavior of the compounds after a single intravenous injection and intragastric administration, and to investigate the bioavailability after intragastric administration.

Experimental Operation:

CD-1 male mice aged from 7 to 10 weeks were selected, and the doses for intravenous and oral administration were 1 mg/kg and 2.5 mg/kg, respectively. The mice were fasted for at least 12 hours before the administration, and resumed feeding 4 hours after the administration. The mice were free to drink during the entire experiment.

On the day of the experiment, animals in the intravenous group were given a single injection of the corresponding compound through the tail vein with a volume of 5 mL/kg; the oral group was given the corresponding compound by a single gavage with a volume of 10 mL/kg. The animals were weighed before administration, and the administration volume was calculated according to the body weight. Sample collection time: 0.083 hours, 0.25 hours, 0.5 hours, 1 hour,

TABLE 4

Evaluation results of PK properties in vivo

| Administration | Parameters | Compound A | Compound 14 |
|---|---|---|---|
| Injection | Dose (mg/kg) | 1 | 1 |
| | $T_{1/2}$ (h) | 0.45 | 1.17 |
| | Vdss (L/Kg) | 1.31 | 1.64 |
| | Cl (mL/min/Kg) | 56.0 | 31.5 |
| | $AUC_{0-last}$ (nm/h) | 814 | 1339 |
| Oral | Dosage (mg/kg) | 5 | 2.5 |
| | $C_{max}$ (nM) | 1837 | 1560 |
| | $T_{max}$ (h) | 0.25 | 0.500 |
| | $T_{1/2}$ (h) | 1.10 | 1.15 |
| | $AUC_{0-last}$ (nM/h) | 1368 | 2696 |
| | F (%) | 33.5 | 80.9 |

What is claimed is:

1. A compound represented by formula (I), a pharmaceutically acceptable salt thereof or a stereoisomer thereof, (I)

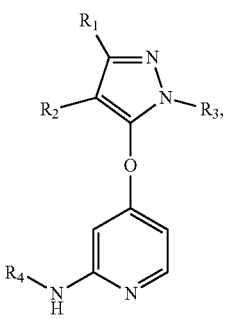

wherein, $R_1$ and $R_2$ are each independently H, F, Cl, Br, —CN,

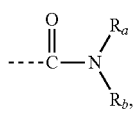

$C_{1-3}$ alkoxy, $C_{1-3}$ alkyl or $C_{3-6}$ cycloalkyl, wherein the $C_{1-3}$ alkoxy, $C_{1-3}$ alkyl and $C_{3-6}$ cycloalkyl are optionally substituted by 1, 2 or 3 substituents independently selected from F or Cl;

or $R_1$ and $R_2$ together with the carbon atom to which they are attached to come together, so that

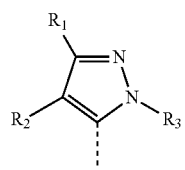

is selected from

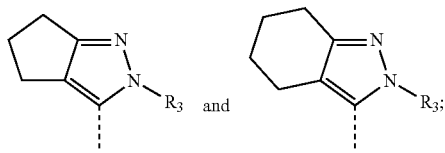

$R_3$ is $C_{1-6}$ alkyl, 5-6 membered heteroaryl, phenyl or 5-6 membered heterocycloalkyl, wherein the $C_{1-6}$ alkyl, 5-6 membered heteroaryl, phenyl and 5-6 membered heterocycloalkyl are optionally substituted by 1, 2 or 3 $R_c$;

each $R_c$ is independently H, F, Cl, Br, I, —CN, —OH, $C_{1-3}$ alkoxy or $C_{1-3}$ alkyl;

$R_4$ is 5-6 membered heteroaryl or phenyl, wherein the 5-6 membered heteroaryl and phenyl are optionally substituted by 1, 2 or 3 $R_d$;

each $R_d$ is independently H, —CN,

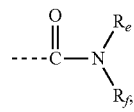

$C_{1-6}$ alkoxy or $C_{1-6}$ alkyl optionally substituted by 1, 2 or 3 substitutes independently selected from F, Cl, Br, I, —OH, —OCH$_3$, —CN and NH$_2$;

$R_a$, $R_b$, $R_e$ and $R_f$ are each independently H, —CH$_3$, —CH$_2$CH$_3$, —CH$_2$CH$_2$CH$_3$ or —CH(CH$_3$)$_2$;

the 5-6 membered heteroaryl and 5-6 membered heterocycloalkyl respectively contain 1, 2, 3 or 4 heteroatoms independently selected from N, —O— and —S—.

2. The compound, the pharmaceutically acceptable salt thereof or the stereoisomer thereof according to claim 1, wherein the $R_1$ and $R_2$ are each independently H, F, Cl, Br, —CN,

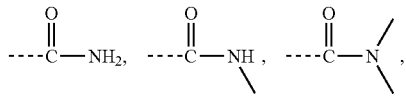

—OCH$_3$, —OCH$_2$CH$_3$, —CH$_3$, —CH$_2$CH$_3$, —CH(CH$_3$)$_2$,

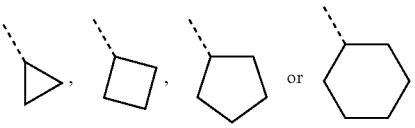

wherein the —OCH$_3$, —OCH$_2$CH$_3$, —CH$_3$, —CH$_2$CH$_3$, —CH(CH$_3$)$_2$,

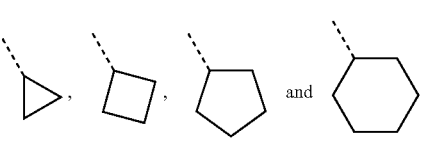

are optionally substituted by 1, 2 or 3 substitutes independently selected from F or Cl.

3. The compound, the pharmaceutically acceptable salt thereof or the stereoisomer thereof according to claim 2, wherein the $R_1$ and $R_2$ are each independently H, F, Cl, Br, —CN,

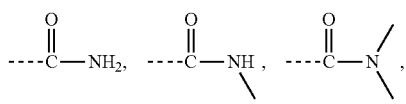

—OCH$_3$, —OCF$_3$, —OCH$_2$CH$_3$, —CH$_3$, —CF$_3$, —CH$_2$CH$_3$, —CH(CH$_3$)$_2$, —CH$_2$CH$_2$Cl,

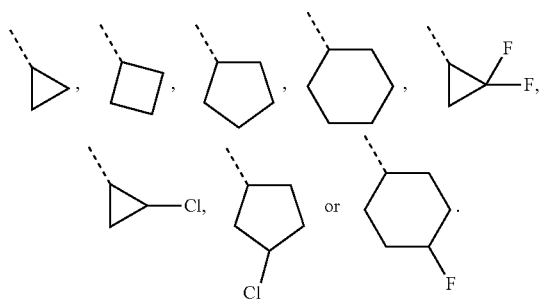

4. The compound, the pharmaceutically acceptable salt thereof or the stereoisomer thereof according to claim 1, which has the structure represented by formula (I-A), (I-B) or (I-C):

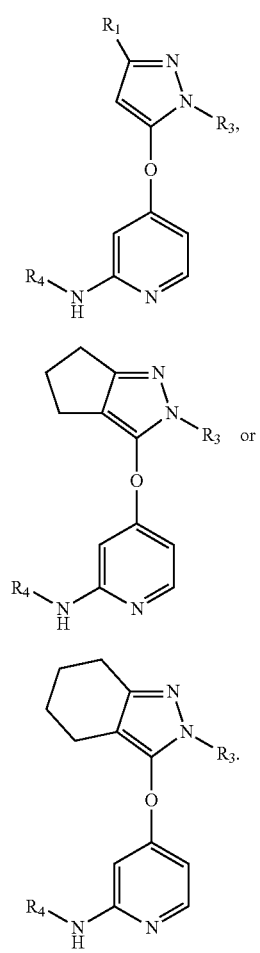

5. The compound, the pharmaceutically acceptable salt thereof or the stereoisomer thereof according to claim 1, wherein each $R_c$ is independently H, F, Cl, Br, I, —CN, —OH, —OCH$_3$, —CH$_3$ or —CH$_2$CH$_3$.

6. The compound, the pharmaceutically acceptable salt thereof or the stereoisomer thereof according to claim 1, wherein the $R_3$ is C$_{1-3}$ alkyl, pyridyl, phenyl or tetrahydro-2H-pyranyl, wherein the C$_{1-3}$ alkyl, pyridyl, phenyl and tetrahydro-2H-pyranyl are optionally substituted by 1, 2 or 3 $R_c$.

7. The compound, the pharmaceutically acceptable salt thereof or the stereoisomer thereof according to claim 6, wherein the $R_3$ is —C(R$_c$)$_3$, —CH$_2$CH$_2$R$_c$,

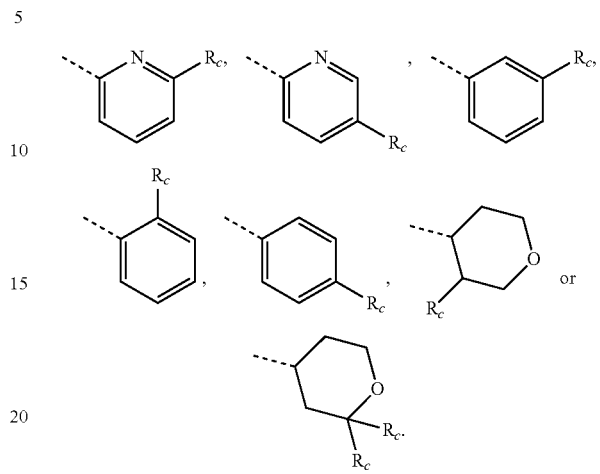

8. The compound, the pharmaceutically acceptable salt thereof or the stereoisomer thereof according to claim 7, wherein the $R_3$ is —CH$_3$, —CF$_3$, —CH$_2$CH$_3$, —CH$_2$CH$_2$F,

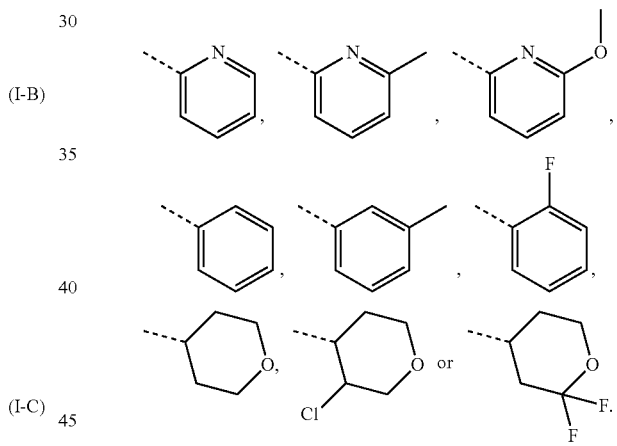

9. The compound, the pharmaceutically acceptable salt thereof or the stereoisomer thereof according to claim 1, which has the structure represented by formula (I-A1)-(I-A3), (I-B1)-(I-B3) or (I-C1)-(I-C3):

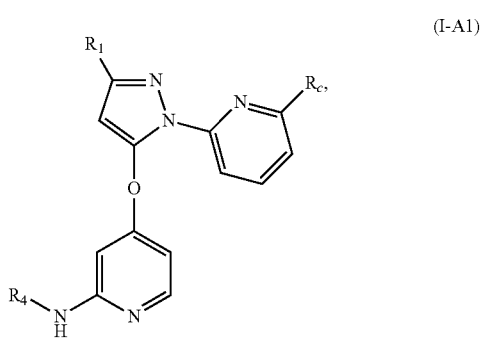

(I-A2)
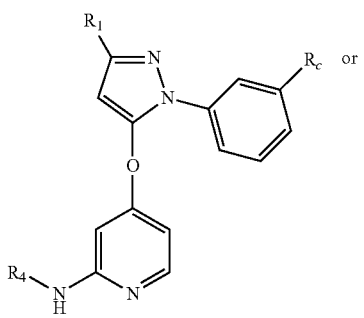

(I-A3)
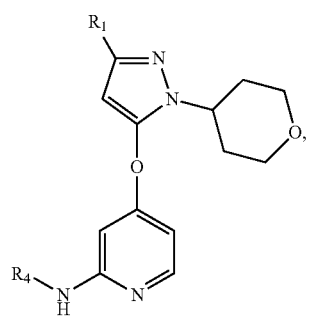

(I-B1)
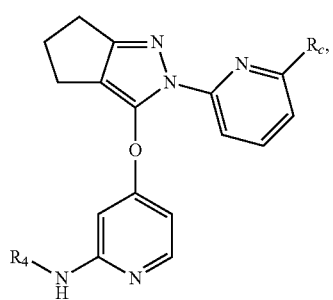

(I-B2)
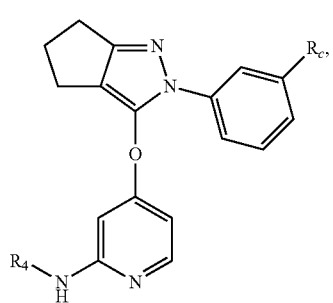

(I-B3)
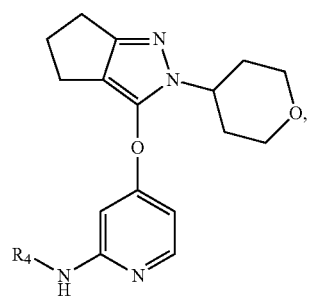

(I-C1)
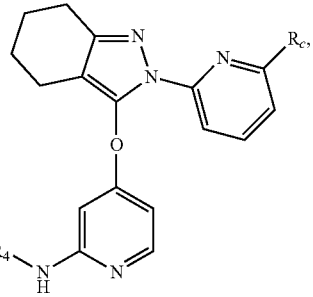

(I-C2)
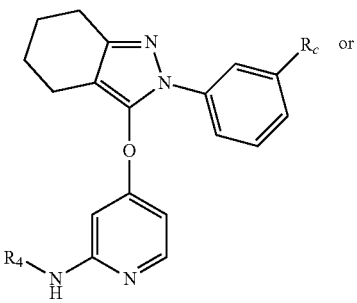

(I-C3)
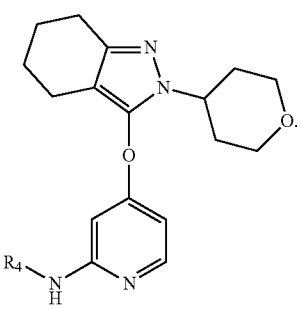

10. The compound, the pharmaceutically acceptable salt thereof or the stereoisomer thereof according to claim 1, wherein each $R_a$ is independently H, —CN,

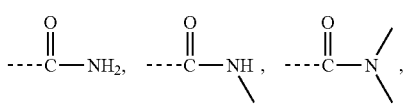

$C_{1-3}$ alkoxy or $C_{1-4}$ alkyl optionally substituted by 1, 2 or 3 substituents independently selected from F, Cl, Br, I, —OH, —OCH$_3$, —CN and NH$_2$.

11. The compound, the pharmaceutically acceptable salt thereof or the stereoisomer thereof according to claim 10, wherein each $R_d$ is independently H, —CN,

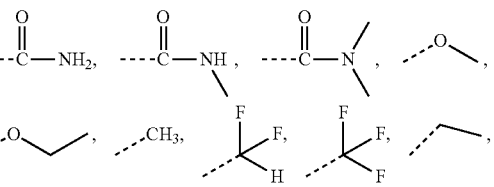

-continued

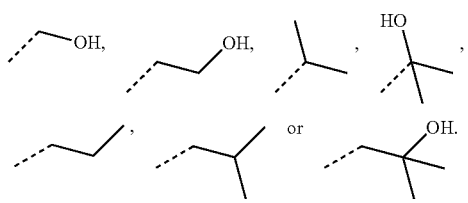

12. The compound, the pharmaceutically acceptable salt thereof or the stereoisomer thereof according to claim 1, wherein the $R_4$ is pyrrolyl, pyrazolyl, pyridyl, pyrazinyl, pyrimidinyl or phenyl, wherein the pyrrolyl, pyrazolyl, pyridyl, pyrazinyl, pyrimidinyl and phenyl are optionally substituted by 1, 2 or 3 $R_d$.

13. The compound, the pharmaceutically acceptable salt thereof or the stereoisomer thereof according to claim 12, wherein the $R_4$ is

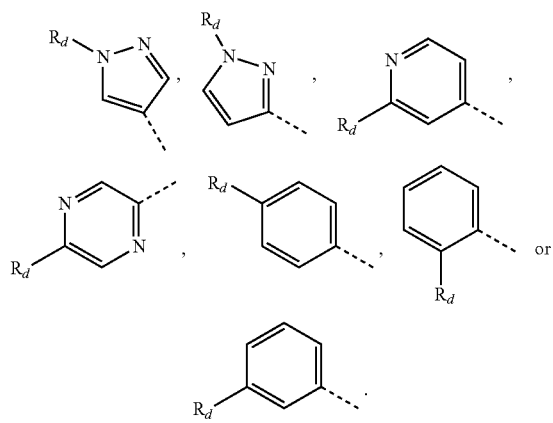

14. The compound, the pharmaceutically acceptable salt thereof or the stereoisomer thereof according to claim 13, wherein the $R_4$ is

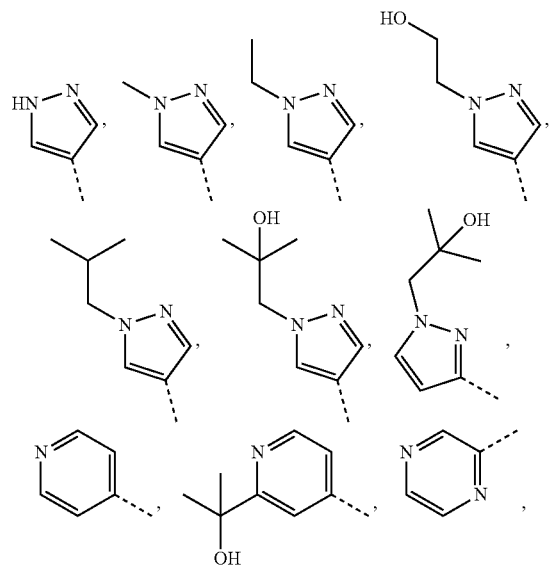

-continued

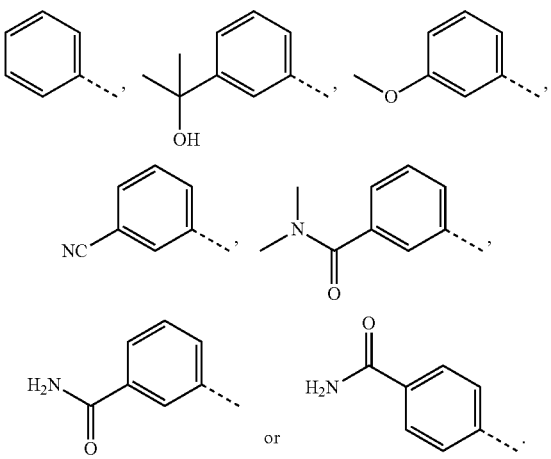

15. The compound, the pharmaceutically acceptable salt thereof or the stereoisomer thereof according to claim 1, which has the structure represented by formula (I-A4)-(I-A15):

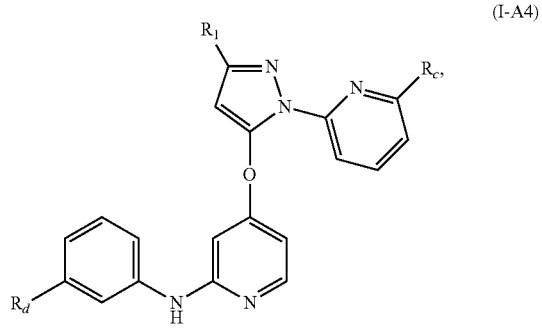

(I-A4)

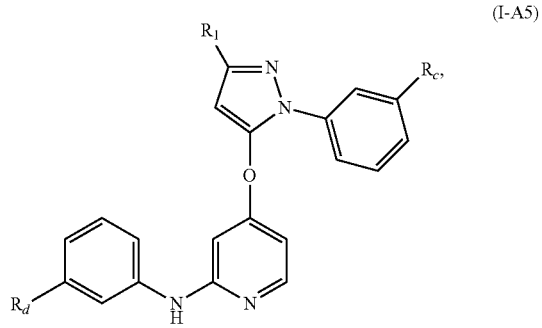

(I-A5)

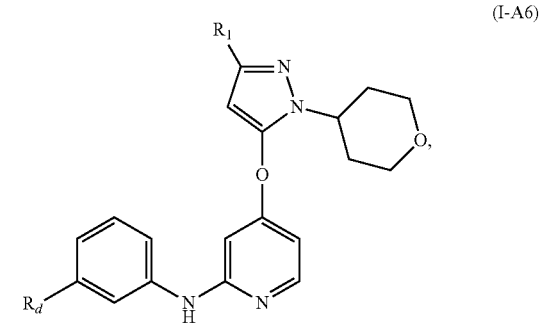

(I-A6)

(I-A7) 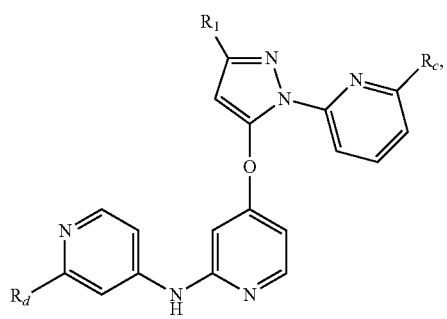
(I-A8) 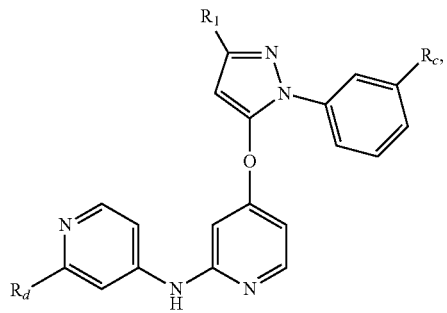
(I-A9) 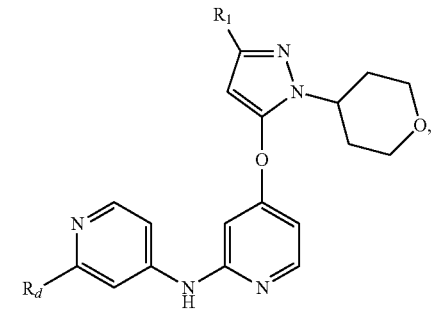
(I-A10) 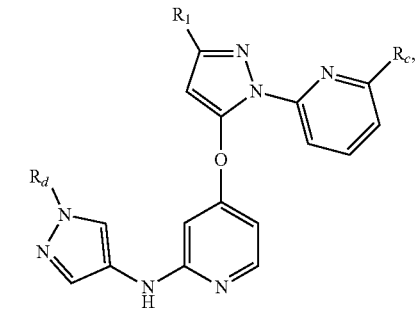
(I-A11) 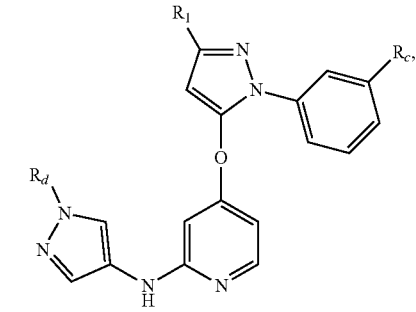
(I-A12) 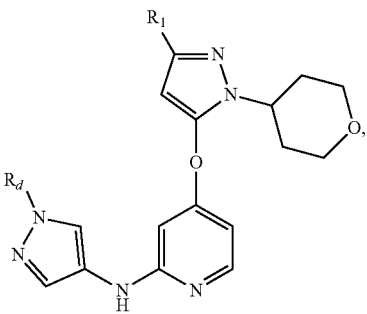
(I-A13) 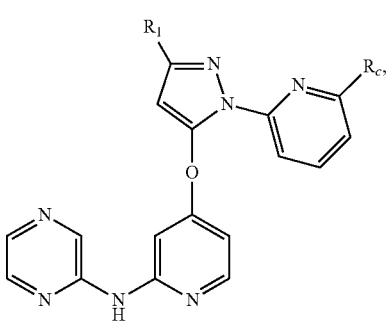
(I-A14) 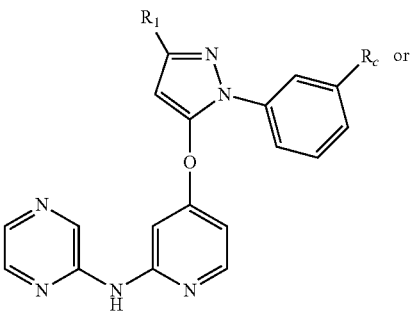
or
(I-A15) 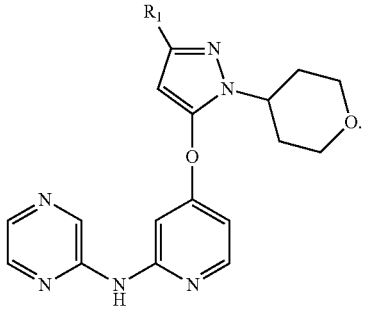
16. The compound, the pharmaceutically acceptable salt thereof or the stereoisomer thereof according to claim 1, which has the structure represented by formula (I-B4)-(I-B6) or (I-C4)-(I-C6):

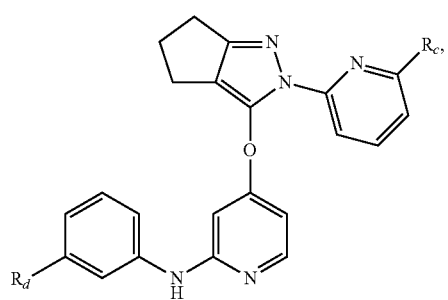 (I-B4)

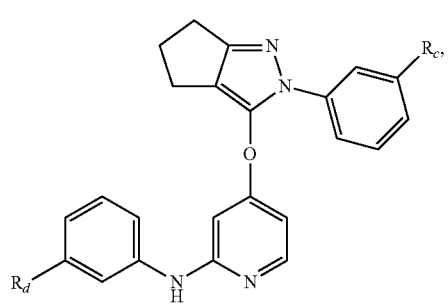 (I-B5)

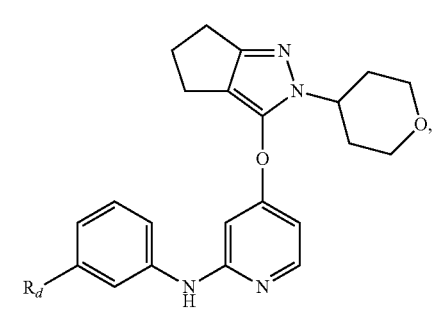 (I-B6)

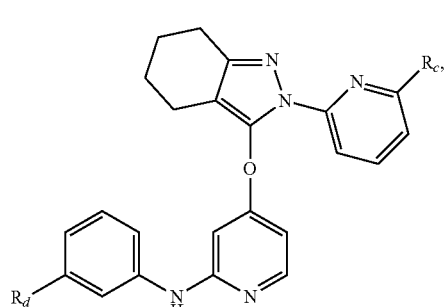 (I-C4)

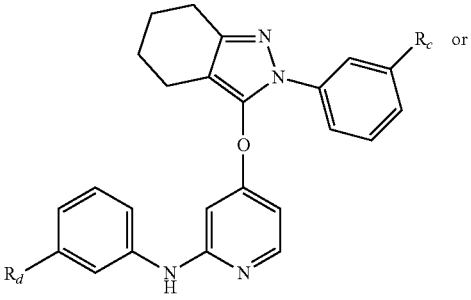 (I-C5) or

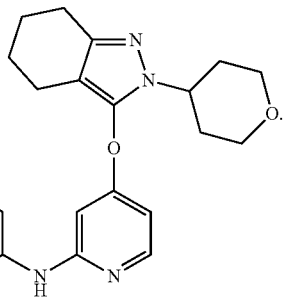 (I-C6)

17. A pharmaceutical composition containing a therapeutically effective amount of the compound, the pharmaceutically acceptable salt thereof or the stereoisomer thereof according to claim 1, and a pharmaceutically acceptable carrier.

18. A method of treating colon cancer in a subject in need thereof, comprising administering the compound, the pharmaceutically acceptable salt thereof or the stereoisomer thereof according to claim 1 to the subject.

19. A compound represented by the following formula, a pharmaceutically acceptable salt thereof or a stereoisomer thereof:

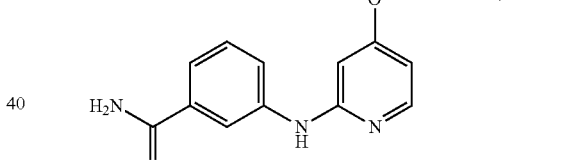

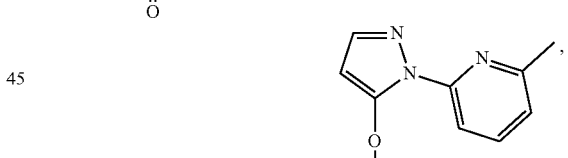

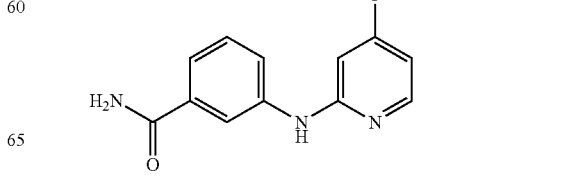

77
-continued
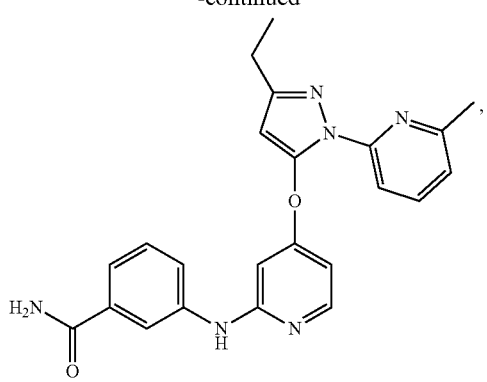
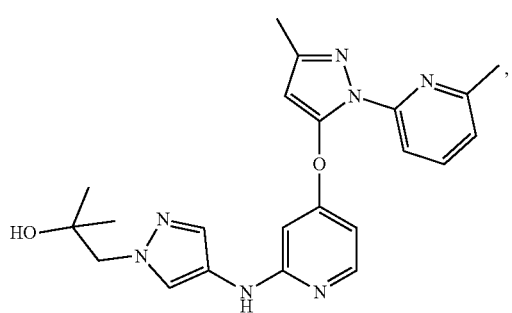
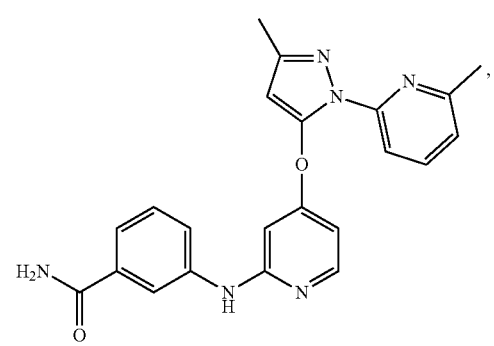
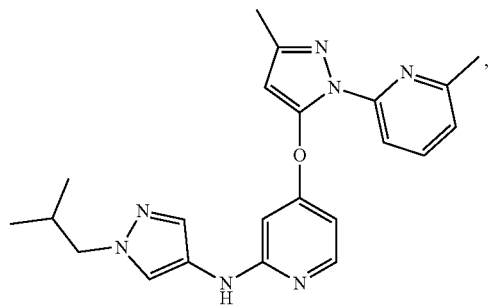
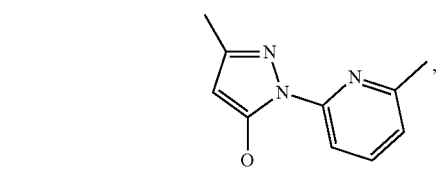
78
-continued
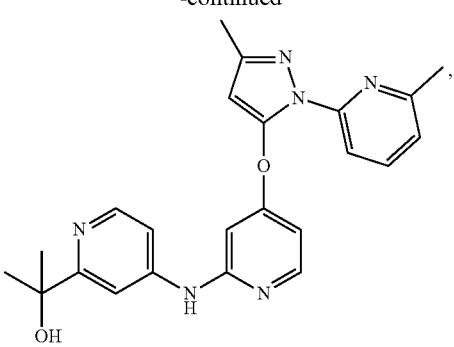
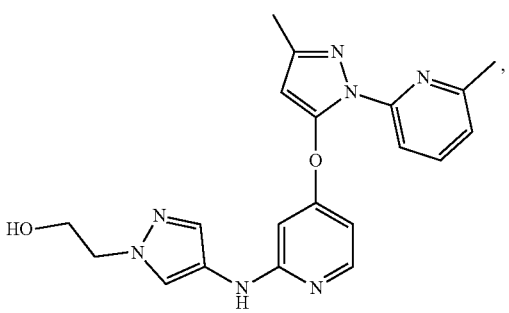
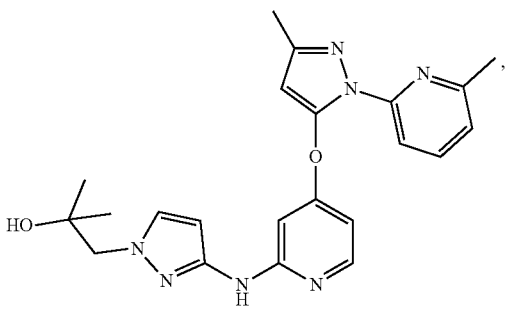
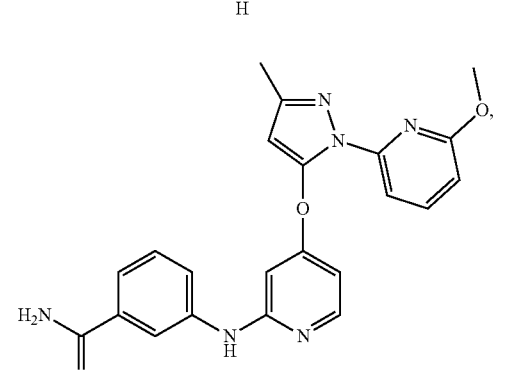
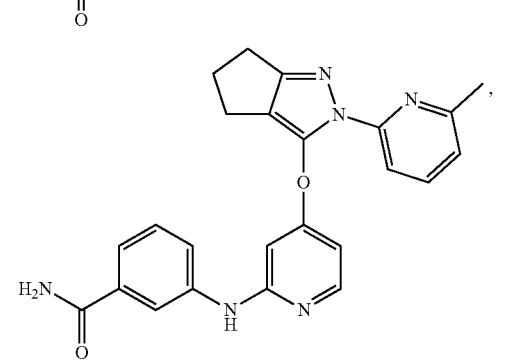

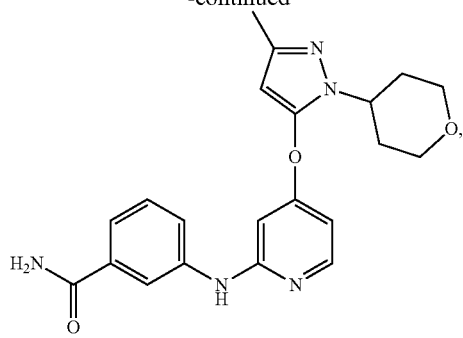
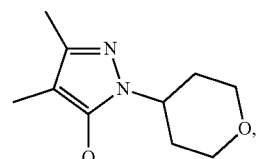
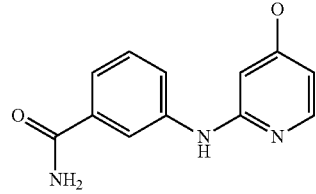
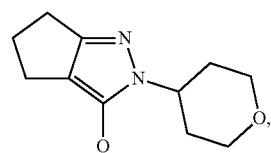
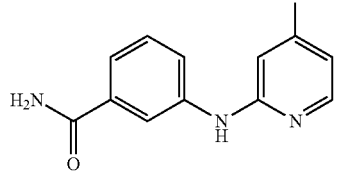
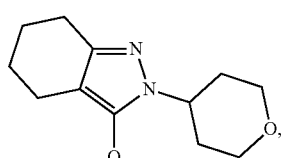
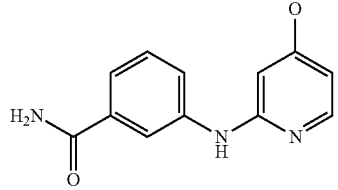
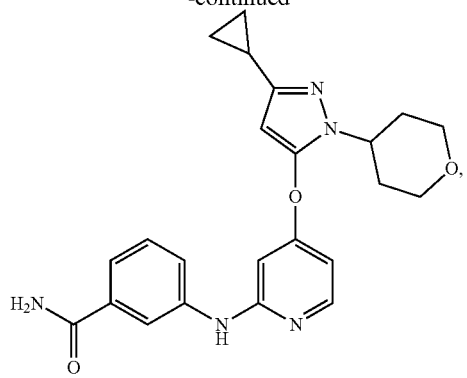
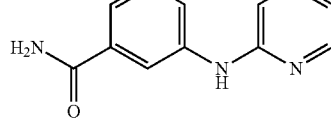
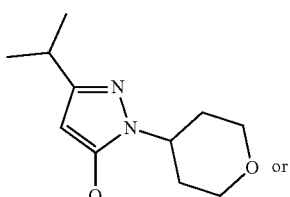
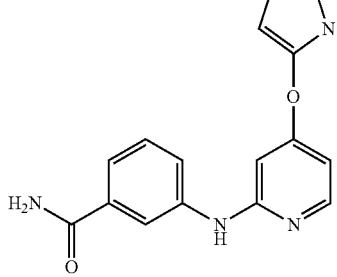 or
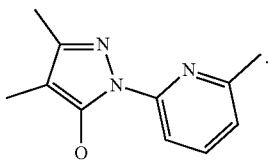
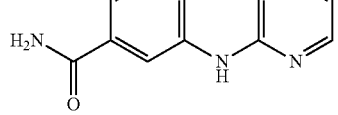
* * * * *